US012433631B2

(12) United States Patent
Weisenburgh, II et al.

(10) Patent No.: US 12,433,631 B2
(45) Date of Patent: Oct. 7, 2025

(54) ULTRASONIC SURGICAL INSTRUMENT WITH MOVABLE RIGIDIZING MEMBER

(71) Applicant: Cilag GmbH International, Zug (CH)

(72) Inventors: William B. Weisenburgh, II, Maineville, OH (US); Barry C. Worrell, Maineville, OH (US); Jeffrey D. Messerly, Cincinnati, OH (US); Kristen L D'Uva, Cincinnati, OH (US); Craig N. Faller, Batavia, OH (US); John B. Schulte, West Chester, OH (US); Kristen G. Denzinger, Cincinnati, OH (US); Joseph E. Hollo, Liberty Township, OH (US); Jason R. Sullivan, Morrow, OH (US); Brian D. Black, Loveland, OH (US); Frederick L. Estera, Cincinnati, OH (US); Stephen M. Leuck, Milford, OH (US); Tylor C. Muhlenkamp, Cincinnati, OH (US); Gregory A. Trees, Loveland, OH (US); Gregory W. Johnson, Minneapolis, MN (US)

(73) Assignee: Cilag GmbH International, Zug (CH)

( * ) Notice: Subject to any disclaimer, the term of this patent is extended or adjusted under 35 U.S.C. 154(b) by 287 days.

(21) Appl. No.: 18/171,043

(22) Filed: Feb. 17, 2023

(65) Prior Publication Data

US 2023/0225754 A1 Jul. 20, 2023

Related U.S. Application Data

(63) Continuation of application No. 16/890,209, filed on Jun. 2, 2020, now Pat. No. 11,684,385, which is a
(Continued)

(51) Int. Cl.
*A61B 17/32* (2006.01)
*A61B 17/295* (2006.01)
(Continued)

(52) U.S. Cl.
CPC .... *A61B 17/320092* (2013.01); *A61B 17/295* (2013.01); *A61B 17/320068* (2013.01);
(Continued)

(58) Field of Classification Search
CPC .. A61B 17/320068; A61B 2017/00314; A61B 2017/00336; A61B 2017/320069
See application file for complete search history.

(56) References Cited

U.S. PATENT DOCUMENTS

| | | |
|---|---|---|
| 5,322,055 A | 6/1994 | Davison et al. |
| 5,873,873 A | 2/1999 | Smith et al. |

(Continued)

FOREIGN PATENT DOCUMENTS

| | | |
|---|---|---|
| JP | 2015-519149 A | 7/2015 |

OTHER PUBLICATIONS

Chinese Search Report dated Nov. 1, 2019, for Application No. 2016800219533, 2 pages.

(Continued)

*Primary Examiner* — Alexander J Orkin
(74) *Attorney, Agent, or Firm* — Frost Brown Todd LLP

(57) ABSTRACT

A surgical apparatus includes a body assembly, a shaft, an acoustic waveguide, an articulation section, an end effector, and a rigidizing member. The shaft extends distally from the body assembly and defines a longitudinal axis. The acoustic waveguide includes a flexible portion. The articulation section is coupled with the shaft. A portion of the articulation section encompasses the flexible portion of the waveguide. The articulation section includes a first member and a second member. The second member is longitudinally trans-
(Continued)

latable relative to the first member. The end effector includes an ultrasonic blade in acoustic communication with the waveguide. The rigidizing member is configured to selectively engage at least a portion of the articulation section to thereby selectively provide rigidity to the articulation section.

19 Claims, 44 Drawing Sheets

Related U.S. Application Data continuation of application No. 14/688,497, filed on Apr. 16, 2015, now abandoned.

(51) Int. Cl.
*A61B 17/00* (2006.01)
*A61B 17/29* (2006.01)

(52) U.S. Cl.
CPC .................. *A61B 2017/003* (2013.01); *A61B 2017/00305* (2013.01); *A61B 2017/00309* (2013.01); *A61B 2017/00314* (2013.01); *A61B 2017/00327* (2013.01); *A61B 2017/00336* (2013.01); *A61B 2017/00424* (2013.01); *A61B 2017/0046* (2013.01); *A61B 2017/2927* (2013.01); *A61B 2017/2946* (2013.01); *A61B 2017/320069* (2017.08); *A61B 2017/320071* (2017.08); *A61B 2017/320089* (2017.08); *A61B 2017/320093* (2017.08); *A61B 2017/320094* (2017.08); *A61B 2017/320095* (2017.08)

(56) References Cited

U.S. PATENT DOCUMENTS 5,897,523 A 4/1999 Wright et al.
5,919,199 A 7/1999 Mers et al.
5,980,510 A 11/1999 Tsonton et al.
5,989,264 A 11/1999 Wright
6,063,098 A 5/2000 Houser et al.
6,090,120 A 7/2000 Wright et al.
6,325,811 B1 12/2001 Messerly
6,454,782 B1 9/2002 Schwemberger
6,589,200 B1 7/2003 Schwemberger et al.
6,752,815 B2 6/2004 Beaupre
6,773,444 B2 8/2004 Messerly
6,783,524 B2 8/2004 Anderson et al.
7,135,030 B2 11/2006 Schwemberger et al.
7,621,930 B2 11/2009 Houser
8,461,744 B2 6/2013 Wiener et al.
8,591,536 B2 11/2013 Robertson
8,623,027 B2 1/2014 Price et al.
8,986,302 B2 3/2015 Aldridge et al.
9,023,071 B2 5/2015 Miller et al.
9,095,367 B2 8/2015 Olson et al.
11,684,385 B2 6/2023 Weisenburgh, II et al.
2002/0165565 A1* 11/2002 Danitz ................ A61B 17/122 606/151
2004/0054322 A1* 3/2004 Vargas ................ A61B 5/1076 604/95.04
2006/0079874 A1 4/2006 Faller et al.
2007/0191713 A1 8/2007 Eichmann et al.
2007/0250113 A1 10/2007 Hegeman et al.
2007/0282333 A1 12/2007 Fortson et al.
2008/0065110 A1* 3/2008 Duval ..................... A61B 1/04 606/130
2008/0200940 A1 8/2008 Eichmann et al.
2008/0234708 A1 9/2008 Houser et al.
2010/0249497 A1 9/2010 Peine et al.
2012/0078247 A1 3/2012 Worrell et al.
2012/0078248 A1 3/2012 Worrell et al.
2012/0112687 A1 5/2012 Houser et al.
2012/0116265 A1 5/2012 Houser et al.
2013/0023923 A1 1/2013 Mueller
2013/0289592 A1 10/2013 Stulen et al.
2013/0331825 A1 12/2013 Mitchell et al.
2014/0005701 A1 1/2014 Olson et al.
2014/0005703 A1 1/2014 Stulen et al.
2014/0236120 A1 8/2014 Tsai et al.
2015/0073224 A1 3/2015 Sartor et al.
2015/0080924 A1 3/2015 Stulen et al.
2016/0302818 A1 10/2016 Weisenburgh, II et al.

OTHER PUBLICATIONS

Chinese Office Action dated Nov. 11, 2019, for Application No. 201680021953.3, 6 pages.
Chinese Search Report dated May 13, 2020, for Application No. 2016800219533, 1 page.
Japanese Search Report dated Feb. 28, 2020, for Application No. 2017-553982, 28 pages.
Japanese Notification of Reasons for refusal dated Feb. 25, 2020, for Application No. 2017-553982, 4 pages.
International Search Report and Written Opinion dated Oct. 20, 2016, for International Application No. PCT/US2016/027684, 10 pages.
U.S. Appl. No. 14/258,179, filed Apr. 22, 2014.
U.S. Appl. No. 61/410,603, entitled "Energy-Based Surgical Instruments," filed Nov. 5, 2010.

* cited by examiner

ULTRASONIC SURGICAL INSTRUMENT WITH MOVABLE RIGIDIZING MEMBER

This application is a continuation of U.S. patent application Ser. No. 16/890,209, entitled "Ultrasonic Surgical Instrument with Movable Rigidizing Member," filed Jun. 2, 2020, and published as U.S. Pub. No. 2020/0360045 on Nov. 19, 2020, issued as U.S. Pat. No. 11,684,385 on Jun. 27, 2023, which is a continuation of U.S. patent application Ser. No. 14/688,497, entitled "Ultrasonic Surgical Instrument with Movable Rigidizing Member," filed Apr. 16, 2015, and published as U.S. Pub. No. 2016/0302818 on Oct. 20, 2016, now abandoned.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, now abandoned, the disclosure of which is incorporated by reference herein; U.S. Pub. No. 2007/0191713, entitled "Ultrasonic Device for Cutting and Coagulating," published Aug. 16, 2007, now abandoned, the disclosure of which is incorporated by reference herein; U.S. Pub. No. 2007/0282333, entitled "Ultrasonic Waveguide and Blade," published Dec. 6, 2007, now abandoned, the disclosure of which is incorporated by reference herein; U.S. Pub. No. 2008/0200940, entitled "Ultrasonic Device for Cutting and Coagulating," published Aug. 21, 2008, now abandoned, the disclosure of which is incorporated by reference herein; U.S. Pub. No. 2009/0105750, entitled "Ergonomic Surgical Instruments," published Apr. 23, 2009, issued as U.S. Pat. No. 8,623,027 on Jan. 7, 2014, the disclosure of which is incorporated by reference herein; U.S. Pub. No. 2010/0069940, entitled "Ultrasonic Device for Fingertip Control," published Mar. 18, 2010, issued as U.S. Pat. No. 9,023,071 on May 5, 2015, the disclosure of which is incorporated by reference herein; and U.S. Pub. No. 2011/0015660, entitled "Rotating Transducer Mount for Ultrasonic Surgical Instruments," published Jan. 20, 2011, issued as U.S. Pat. No. 8,461,744 on Jun. 11, 2013, the disclosure of which is incorporated by reference herein; and U.S. Pub. No. 2012/0029546, entitled "Ultrasonic Surgical Instrument Blades," published Feb. 2, 2012, issued as U.S. Pat. No. 8,591,536 on Nov. 26, 2013, the disclosure of which is incorporated by reference herein.

Some ultrasonic surgical instruments may include a cordless transducer such as that disclosed in U.S. Pub. No. 2012/0112687, entitled "Recharge System for Medical Devices," published May 10, 2012, issued as U.S. Pat. No. 9,381,058 on Jul. 5, 2016, the disclosure of which is incorporated by reference herein; U.S. Pub. No. 2012/0116265, entitled "Surgical Instrument with Charging Devices," published May 10, 2012, now abandoned, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section and/or a bendable ultrasonic waveguide. Examples of such ultrasonic surgical instruments are disclosed in U.S. Pat. No. 5,897,523, entitled "Articulating Ultrasonic Surgical Instrument," issued Apr. 27, 1999, the disclosure of which is incorporated by reference herein; U.S. Pat. No. 5,989,264, entitled "Ultrasonic Polyp Snare," issued Nov. 23, 1999, the disclosure of which is incorporated by reference herein; U.S. Pat. No. 6,063,098, entitled "Articulable Ultrasonic Surgical Apparatus," issued May 16, 2000, the disclosure of which is incorporated by reference herein; U.S. Pat. No. 6,090,120, entitled "Articulating Ultrasonic Surgical Instrument," issued Jul. 18, 2000, the disclosure of which is incorporated by reference herein; U.S. Pat. No. 6,454,782, entitled "Actuation Mechanism for Surgical Instruments," issued Sep. 24, 2002, the disclosure of which is incorporated by reference herein; U.S. Pat. No. 6,589,200, entitled "Articulating Ultrasonic Surgical Shears," issued Jul. 8, 2003, the disclosure of which is incorporated by reference herein; U.S. Pat. No. 6,752,815, entitled "Method and Waveguides for Changing the Direction of Longitudinal Vibrations," issued Jun. 22, 2004, the disclosure of which is incorporated by reference herein; U.S. Pat. No. 7,135,030, entitled "Articulating Ultrasonic Surgical Shears," issued Nov. 14, 2006; U.S. Pat. No. 7,621,930, entitled "Ultrasound Medical Instrument Having a Medical Ultrasonic Blade," issued Nov. 24, 2009, the disclosure of which is incorporated by reference herein; U.S. Pub. No. 2014/0005701, published Jan. 2, 2014, issued as U.S. Pat. No. 9,393,037 on Jul. 19, 2016, entitled "Surgical Instruments with Articulating Shafts," the disclosure of which is incorporated by reference herein; U.S. Pub. No. 2014/005703, entitled "Surgical Instruments with Articulating Shafts," published Jan. 2, 2014, issued as U.S. Pat. No. 9,408,622 on Aug. 9, 2016, the disclosure of which is incorporated by reference herein; U.S. Pub. No. 2014/0114334, entitled "Flexible Harmonic Waveguides/Blades for Surgical Instruments," published Apr. 24, 2014, issued as U.S. Pat. No. 9,095,367 on Aug. 4, 2015, the disclosure of which is incorporated by reference herein; U.S. Pub. No. 2015/0080924, entitled "Articulation Features for Ultrasonic Surgical Instrument," published Mar. 19, 2015, issued as U.S. Pat. No. 10,172,636 on Jan. 8, 2019, the disclosure of which is incorporated by reference herein; and U.S. patent application Ser. No. 14/258,179, entitled Ultrasonic Surgical Device with Articulating End Effector," filed Apr. 22, 2014, converted to U.S. Provisional App. No. 62/176,800 on Apr. 8, 2015, the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
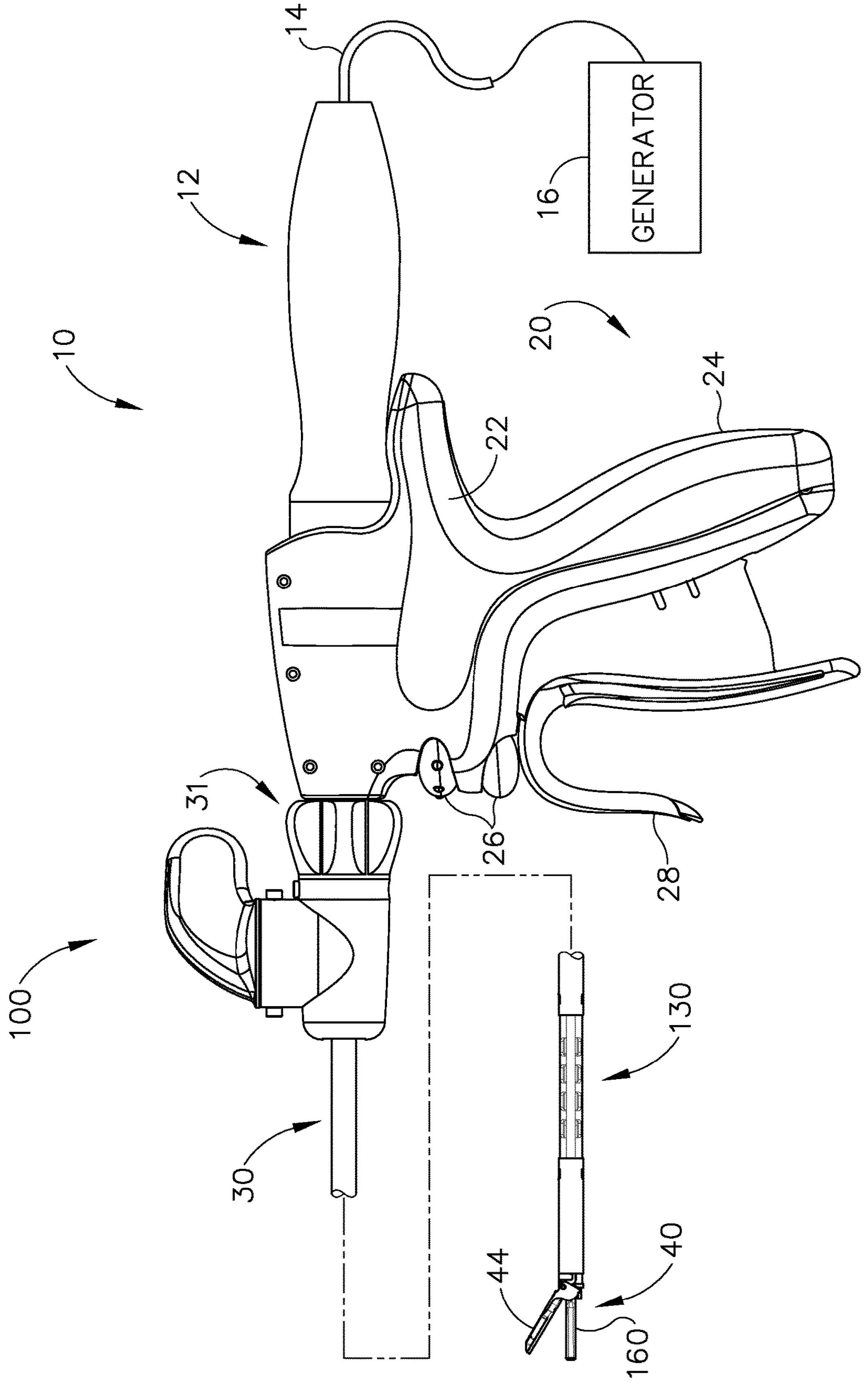
FIG. 1 depicts a side elevational view of an exemplary ultrasonic surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIG. 1 shows an exemplary ultrasonic surgical instrument (10). At least part of instrument (10) may be constructed and operable in accordance with at least some of the teachings of any of the various patents, patent application publications, and patent applications that are cited herein. As described therein and as will be described in greater detail below, instrument (10) is operable to cut tissue and seal or weld tissue (e.g., a blood vessel, etc.) substantially simultaneously. It should also be understood that instrument (10) may have various structural and functional similarities with the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (10) may have various structural and functional similarities with the devices taught in any of the other references that are cited and incorporated by reference herein.

To the extent that there is some degree of overlap between the teachings of the references cited herein, the HARMONIC ACE® Ultrasonic Shears, the HARMONIC WAVE® Ultrasonic Shears, the HARMONIC FOCUS® Ultrasonic Shears, and/or the HARMONIC SYNERGY® Ultrasonic Blades, and the following teachings relating to instrument (10), there is no intent for any of the description herein to be presumed as admitted prior art. Several teachings herein will in fact go beyond the scope of the teachings of the references cited herein and the HARMONIC ACE® Ultrasonic Shears, the HARMONIC WAVE® Ultrasonic Shears, the HARMONIC FOCUS® Ultrasonic Shears, and the HARMONIC SYNERGY® Ultrasonic Blades.

Instrument (10) of the present example comprises a handle assembly (20), a shaft assembly (30), and an end effector (40). Handle assembly (20) comprises a body (22) including a pistol grip (24) and a pair of buttons (26). Handle assembly (20) also includes a trigger (28) that is pivotable toward and away from pistol grip (24). It should be understood, however, that various other suitable configurations may be used, including but not limited to a scissor grip configuration. End effector (40) includes an ultrasonic blade (160) and a pivoting clamp arm (44). Clamp arm (44) is coupled with trigger (28) such that clamp arm (44) is pivotable toward ultrasonic blade (160) in response to pivoting of trigger (28) toward pistol grip (24); and such that clamp arm (44) is pivotable away from ultrasonic blade (160) in response to pivoting of trigger (28) away from pistol grip (24). Various suitable ways in which clamp arm (44) may be coupled with trigger (28) will be apparent to those of ordinary skill in the art in view of the teachings herein. In some versions, one or more resilient members are used to bias clamp arm (44) and/or trigger (28) to the open position shown in FIG. 1.

An ultrasonic transducer assembly (12) extends proximally from body (22) of handle assembly (20). Transducer assembly (12) is coupled with a generator (16) via a cable (14), such that transducer assembly (12) receives electrical power from generator (16). Piezoelectric elements in transducer assembly (12) convert that electrical power into ultrasonic vibrations. Generator (16) may include a power source and control module that is configured to provide a power profile to transducer assembly (12) that is particularly suited for the generation of ultrasonic vibrations through transducer assembly (12). By way of example only, generator (16) may comprise a GEN 300 sold by Ethicon Endo-Surgery, Inc. of Cincinnati, Ohio. In addition or in the alternative, generator (16) may be constructed in accordance with at least some of the teachings of U.S. Pub. No. 2011/0087212, entitled "Surgical Generator for Ultrasonic and Electrosurgical Devices," published Apr. 14, 2011, issued as U.S. Pat. No. 8,986,302 on Mar. 24, 2015, the disclosure of which is incorporated by reference herein. It should also be understood that at least some of the functionality of generator (16) may be integrated into handle assembly (20), and that handle assembly (20) may even include a battery or other on-board power source such that cable (14) is omitted. Still other suitable forms that generator (16) may take, as well as various features and operabilities that generator (16) may provide, will be apparent to those of ordinary skill in the art in view of the teachings herein.

A. Exemplary End Effector and Acoustic Drivetrain

Figure 2:
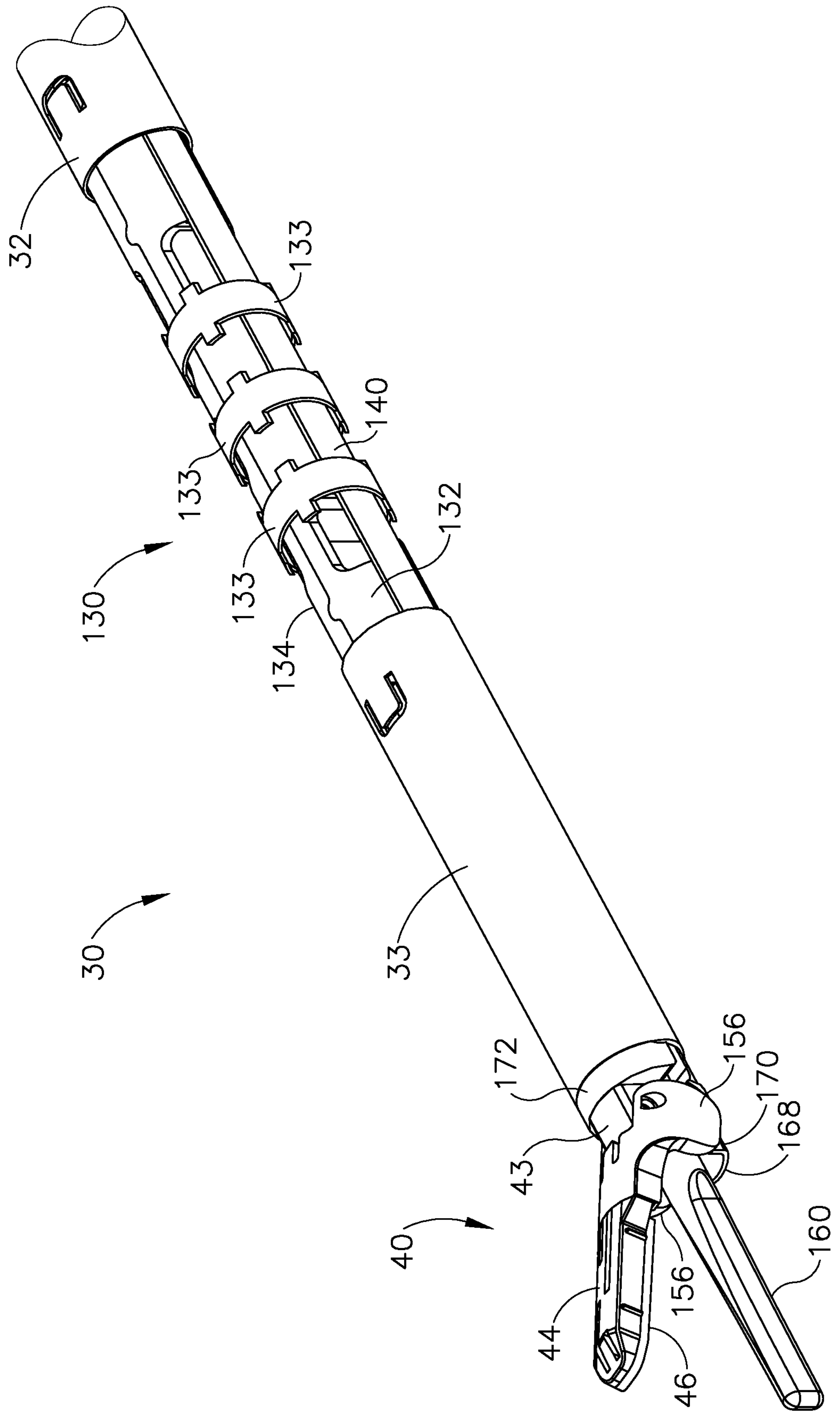
FIG. 2 depicts a perspective view of an articulation section of a shaft assembly and an end effector of the surgical instrument of FIG. 1.
Figure 3:
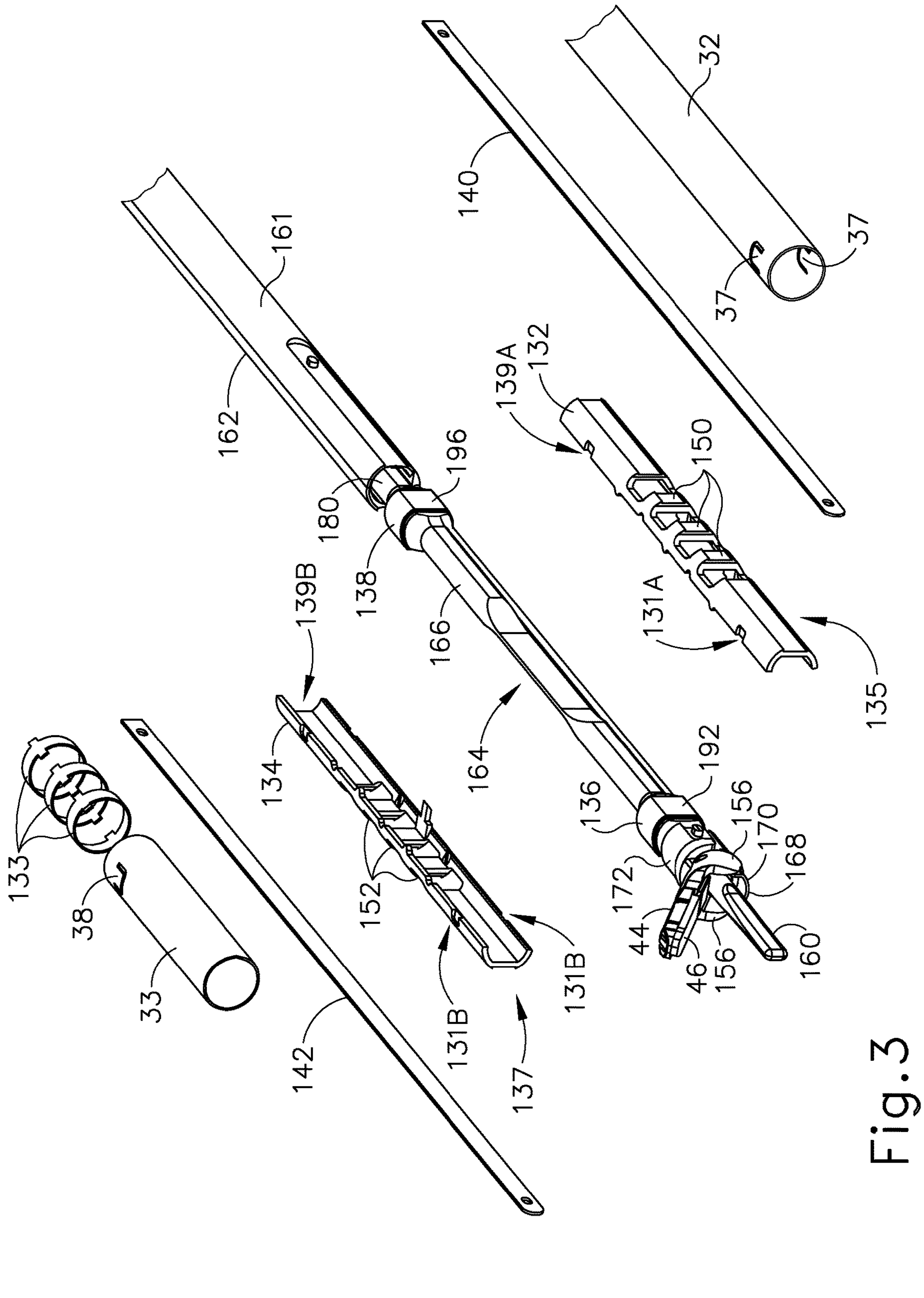
FIG. 3 depicts an exploded perspective view of an articulation section of the shaft assembly of FIG. 2.
Figure 4:
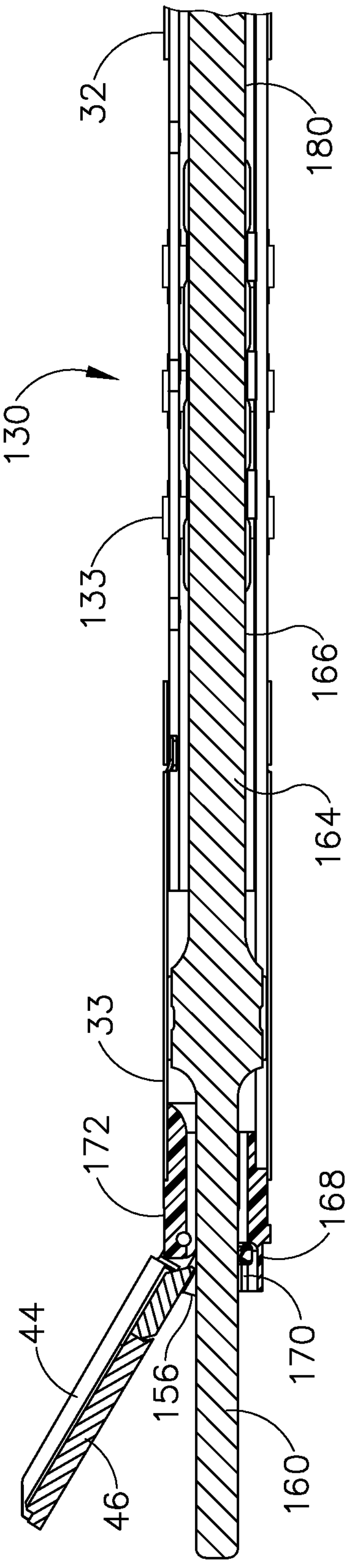
FIG. 4 depicts a cross-sectional side view of the shaft assembly and end effector of FIG. 2.

As best seen in FIGS. 2-4, end effector (40) of the present example comprises clamp arm (44) and ultrasonic blade (160). Clamp arm (44) includes a clamp pad (46) that is secured to the underside of clamp arm (44), facing blade (160). Clamp pad (46) may comprise polytetrafluoroethylene (PTFE) and/or any other suitable material(s). Clamp arm (44) is pivotally secured to a distally projecting tongue (43) of an upper distal shaft element (172), which is fixedly secured within a distal portion of a distal outer sheath (33). Clamp arm (44) is operable to selectively pivot toward and away from blade (160) to selectively clamp tissue between clamp arm (44) and blade (160). A pair of arms (156) extend transversely from clamp arm (44) and are pivotally secured to a lower distal shaft element (170), which is slidably disposed within the distal portion of distal outer sheath (33).

In some examples a cable (not shown) may be secured to lower distal shaft element (170). Such a cable may be operable to translate longitudinally relative to an articulation section (130) of shaft assembly (30) to selectively pivot clamp arm (44) toward and away from blade (160). In further examples, the cable is coupled with trigger (28) such that the cable translates proximally in response to pivoting of trigger (28) toward pistol grip (24), and such that clamp arm (44) thereby pivots toward blade (160) in response to pivoting of trigger (28) toward pistol grip (24). In addition, the cable may translate distally in response to pivoting of trigger (28) away from pistol grip (24), such that clamp arm (44) pivots away from blade (160) in response to pivoting of trigger (28) away from pistol grip (24). Clamp arm (44) may be biased toward the open position, such that (at least in some instances) the operator may effectively open clamp arm (44) by releasing a grip on trigger (28).

Blade (160) of the present example is operable to vibrate at ultrasonic frequencies in order to effectively cut through and seal tissue, particularly when the tissue is being compressed between clamp pad (46) and blade (160). Blade (160) is positioned at the distal end of an acoustic drivetrain. This acoustic drivetrain includes transducer assembly (12) and an acoustic waveguide (180). Acoustic waveguide (180) comprises a flexible portion (166). Transducer assembly (12) includes a set of piezoelectric discs (not shown) located proximal to a horn (not shown) of waveguide (180). The piezoelectric discs are operable to convert electrical power into ultrasonic vibrations, which are then transmitted along waveguide (180), including flexible portion (166) of waveguide (180) to blade (160) in accordance with known configurations and techniques. By way of example only, this portion of the acoustic drivetrain may be configured in accordance with various teachings of various references that are cited herein.

As best seen in FIG. 3, flexible portion (166) of waveguide (180) includes a distal flange (136), a proximal flange (138), and a narrowed section (164) located between flanges (136, 138). In the present example, flanges (136, 138) are located at positions corresponding to nodes associated with resonant ultrasonic vibrations communicated through flexible portion (166) of waveguide (180). Narrowed section (164) is configured to allow flexible portion (166) of waveguide (180) to flex without significantly affecting the ability of flexible portion (166) of waveguide (180) to transmit ultrasonic vibrations. By way of example only, narrowed section (164) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. It should be understood that waveguide (180) may be configured to amplify mechanical vibrations transmitted through waveguide (180). Furthermore, waveguide (180) may include features operable to control the gain of the longitudinal vibrations along waveguide (180) and/or features to tune waveguide (180) to the resonant frequency of the system. Various suitable ways in which waveguide (180) may be mechanically and acoustically coupled with transducer assembly (12) will be apparent to those of ordinary skill in the art in view of the teachings herein.

In the present example, the distal end of blade (160) is located at a position corresponding to an anti-node associated with resonant ultrasonic vibrations communicated through flexible portion (166) of waveguide (180), in order to tune the acoustic assembly to a preferred resonant frequency $f_o$ when the acoustic assembly is not loaded by tissue. When transducer assembly (12) is energized, the distal end of blade (160) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (12) of the present example is activated, these mechanical oscillations are transmitted through waveguide (180) to reach blade (160), thereby providing oscillation of blade (160) at the resonant ultrasonic frequency. Thus, when tissue is secured between blade (160) and clamp pad (46), the ultrasonic oscillation of blade (160) may simultaneously sever the tissue and denature the proteins in adjacent tissue cells, thereby providing a coagulative effect with relatively little thermal spread. In some versions, an electrical current may also be provided through blade (160) and clamp arm (44) to also cauterize the tissue. While some configurations for an acoustic transmission assembly and transducer assembly (12) have been described, still other suitable configurations for an acoustic transmission assembly and transducer assembly (12) will be apparent to one or ordinary skill in the art in view of the teachings herein. Similarly, other suitable configurations for end effector (40) will be apparent to those of ordinary skill in the art in view of the teachings herein.

B. Exemplary Shaft Assembly and Articulation Section

Shaft assembly (30) of the present example extends distally from handle assembly (20). As shown in FIGS. 2-6B, shaft assembly (30) includes distal outer sheath (33) and a proximal outer sheath (32) that enclose clamp arm (44) drive features and the above-described acoustic transmission features. Shaft assembly (30) further includes an articulation section (130), which is located at a distal portion of shaft assembly (30), with end effector (40) being located distal to articulation section (130). As shown in FIG. 1, a knob (31) is secured to a proximal portion of proximal outer sheath (32). Knob (31) is rotatable relative to body (22), such that shaft assembly (30) is rotatable about the longitudinal axis defined by outer sheath (32), relative to handle assembly (20). Such rotation may provide rotation of end effector (40), articulation section (130), and shaft assembly (30) unitarily. Of course, rotatable features may simply be omitted if desired.

Articulation section (130) is operable to selectively position end effector (40) at various lateral deflection angles relative to a longitudinal axis defined by outer sheath (32). Articulation section (130) may take a variety of forms. By way of example only, articulation section (130) may be configured in accordance with one or more teachings of U.S. Pub. No. 2012/0078247, issued as U.S. Pat. No. 9,402,682 on Aug. 2, 2016, the disclosure of which is incorporated by reference herein. As another merely illustrative example, articulation section (130) may be configured in accordance with one or more teachings of U.S. Pub. No. 2014/0005701, issued as U.S. Pat. No. 9,393,037 on Jul. 19, 2016, and/or U.S. Pub. No. 2014/0114334, issued as U.S. Pat. No. 9,095,367 on Aug. 4, 2015, the disclosures of which are incorporated by reference herein. Various other suitable forms that articulation section (130) may take will be apparent to those of ordinary skill in the art in view of the teachings herein.

As best seen in FIGS. 2-6B articulation section (130) of this example comprises a set of three retention collars (133) and a pair of ribbed body portions (132, 134), with a pair of articulation bands (140, 142) extending along respective channels (135, 137) defined between interior surfaces of retention collars (133) and exterior surfaces of ribbed body portions (132, 134). Ribbed body portions (132, 134) are longitudinally positioned between flanges (136, 138) of flexible portion (166) of waveguide (180). In some versions, ribbed body portions (132, 134) snap together about flexible portion (166) of waveguide (180). Ribbed body portions (132, 134) are configured to flex with flexible portion (166) of waveguide (180) when articulation section (130) bends to achieve an articulated state.

FIG. 3 shows ribbed body portions (132, 134) in greater detail. In the present example, ribbed body portions (132, 134) are formed of a flexible plastic material, though it should be understood that any other suitable material may be used. Ribbed body portion (132) comprises a set of three ribs (150) that are configured to promote lateral flexing of ribbed body portion (132). Of course, any other suitable number of ribs (150) may be provided. Ribbed body portion (132) also defines a channel (135) that is configured to receive articulation band (140) while allowing articulation band (140) to slide relative to ribbed body portion (132). Similarly, ribbed body portion (134) comprises a set of three ribs (152) that are configured to promote lateral flexing of ribbed body portion (134). Of course, any other suitable number of ribs (152) may be provided. Ribbed body portion (134) also defines a channel (137) that is configured to receive articulation band (142) while allowing articulation band (142) to slide relative to ribbed body portion (137).

Figure 5:
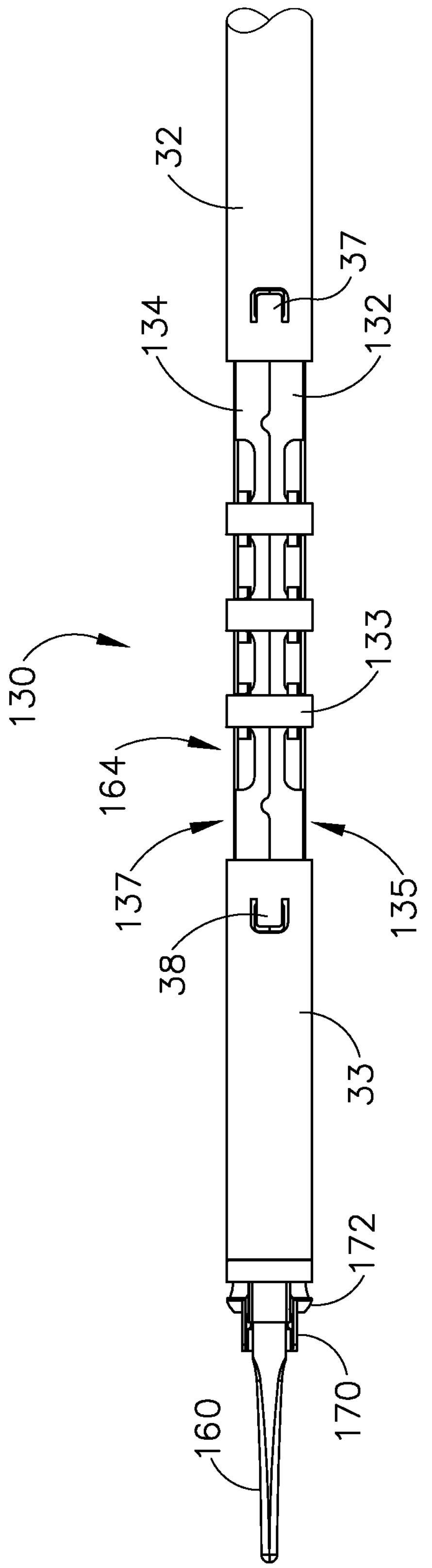
FIG. 5 depicts a top plan view of the shaft assembly and end effector of FIG. 2.

As best seen in FIG. 5, ribbed body portions (132, 134) are laterally interposed between articulation bands (140, 142) and flexible portion (166) of waveguide (180). Ribbed body portions (132, 134) mate with each other such that they together define an internal passage sized to accommodate flexible portion (166) of waveguide (180) without contacting waveguide (180). In addition, when ribbed body portions (132, 134) are coupled together, a pair of complementary distal notches (131A, 131B) formed in ribbed body portions (132, 134) align to receive a pair of inwardly projecting resilient tabs (38) of distal outer sheath (33). This engagement between tabs (38) and notches (131A, 131B) longitudinally secures ribbed body portions (132, 134) relative to distal outer sheath (33). Similarly, when ribbed body portions (132, 134) are coupled together, a pair of complementary proximal notches (139A, 139B) formed in ribbed body portions (132, 134) align to receive a pair of inwardly projecting resilient tabs (37) of proximal outer sheath (32). This engagement between tabs (37) and notches (139A, 139B) longitudinally secures ribbed body portions (132, 134) relative to proximal outer sheath (32). Of course, any other suitable kinds of features may be used to couple ribbed body portions (132, 134) with proximal outer sheath (32) and/or distal outer sheath (33).

Figure 6A:
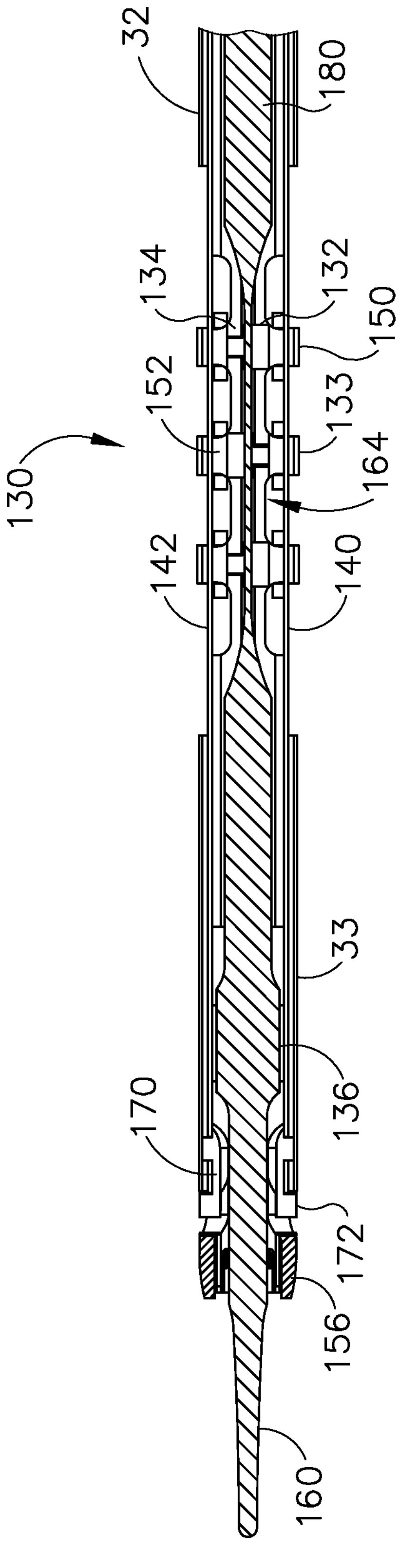
FIG. 6A depicts a cross-sectional top view of the shaft assembly and end effector of FIG. 2 in a straight configuration.
Figure 6B:
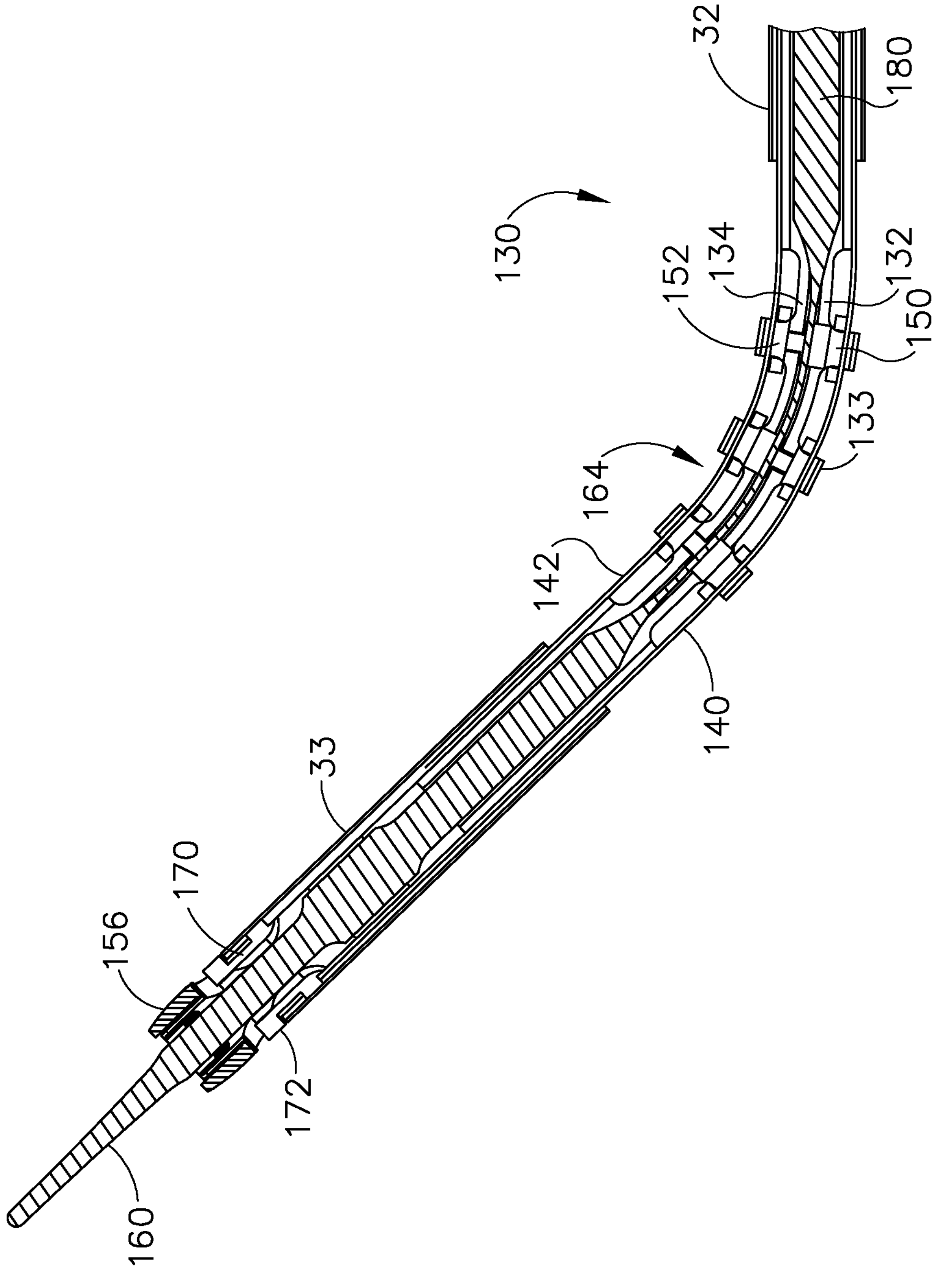
FIG. 6B depicts a cross-sectional top view of the shaft assembly and end effector of FIG. 2 in an articulated configuration.

The distal ends of articulation bands (140, 142) are unitarily secured to upper distal shaft element (172). When articulation bands (140, 142) translate longitudinally in an opposing fashion, this will cause articulation section (130) to bend, thereby laterally deflecting end effector (40) away from the longitudinal axis of shaft assembly (30) from a straight configuration as shown in FIG. 6A to an articulated configuration as shown in FIG. 6B. In particular, end effector (40) will be articulated toward the articulation band (140, 142) that is being pulled proximally. During such articulation, the other articulation band (140, 142) may be pulled distally by upper distal shaft element (172). Alternatively, the other articulation band (140, 142) may be driven distally by an articulation control. Ribbed body portions (132, 134) and narrowed section (164) are all sufficiently flexible to accommodate the above-described articulation of end effector (40). Furthermore, flexible acoustic waveguide (166) is configured to effectively communicate ultrasonic vibrations from waveguide (180) to blade (160) even when articulation section (130) is in an articulated state as shown in FIG. 6B.

As best seen in FIG. 3, each flange (136, 138) of waveguide (180) includes a respective pair of opposing flats (192, 196). Flats (192, 196) are oriented along vertical planes that are parallel to a vertical plane extending through narrowed section (164) of flexible portion (166). Flats (192, 196) are configured to provide clearance for articulation bands (140, 142). In particular, flats (196) of proximal flange (138) accommodate articulation bands (140, 142) between proximal flange (138) and the inner diameter of proximal outer sheath (32); while flats (192) of distal flange (136) accommodate articulation bands (140, 142) between distal flange (136) and the inner diameter of distal outer sheath (33). Of course, flats (192, 196) could be substituted with a variety of features, including but not limited to slots, channels, etc., with any suitable kind of profile (e.g., square, flat, round, etc.). In the present example, flats (192, 196) are formed in a milling process, though it should be understood that any other suitable process(es) may be used. Various suitable alternative configurations and methods of forming flats (192, 196) will be apparent to those of ordinary skill in the art in view of the teachings herein. It should also be understood that waveguide (180) may include flats formed in accordance with at least some of the teachings of U.S. Pub. No. 2013/0289592, entitled "Ultrasonic Device for Cutting and Coagulating," published Oct. 31, 2013, issued as U.S. Pat. No. 10,238,416 on Mar. 26, 2019, the disclosure of which is incorporated by reference herein.

In the present example, outer rings (133) are located at longitudinal positions corresponding to ribs (150, 152), such that three rings (133) are provided for three ribs (150, 152). Articulation band (140) is laterally interposed within channel (135) between rings (133) and ribbed body portion (132); while articulation band (142) is laterally interposed within channel (137) between rings (133) and ribbed body portion (134). Rings (133) are configured to keep articulation bands (140, 142) in a parallel relationship, particularly when articulation section (130) is in a bent configuration (e.g., similar to the configuration shown in FIG. 6B). In other words, when articulation band (140) is on the inner diameter of a curved configuration presented by a bent articulation section (130), rings (133) may retain articulation band (140) such that articulation band (140) follows a curved path that complements the curved path followed by articulation band (142). It should be understood that channels (135, 137) are sized to accommodate respective articulation bands (140, 142) in such a way that articulation bands (140, 142) may still freely slide through articulation section (130), even with rings (133) being secured to ribbed body portions (150, 152). It should also be understood that rings (133) may be secured to ribbed body portions (132, 134) in various ways, including but not limited to interference fitting, adhesives, welding, etc.

When articulation bands (140, 142) are translated longitudinally in an opposing fashion, a moment is created and applied to a distal end of distal outer sheath (33) via upper distal shaft element (172). This causes articulation section (130) and narrowed section (164) of flexible portion (166) of waveguide (180) to articulate, without transferring axial forces in articulation bands (140, 142) to waveguide (180). It should be understood that one articulation band (140, 142) may be actively driven distally while the other articulation band (140, 142) is passively permitted to retract proximally. As another merely illustrative example, one articulation band (140, 142) may be actively driven proximally while the other articulation band (140, 142) is passively permitted to advance distally. As yet another merely illustrative example, one articulation band (140, 142) may be actively driven distally while the other articulation band (140, 142) is actively driven proximally. Various suitable ways in which articulation bands (140, 142) may be driven will be apparent to those of ordinary skill in the art in view of the teachings herein.

Figure 7:
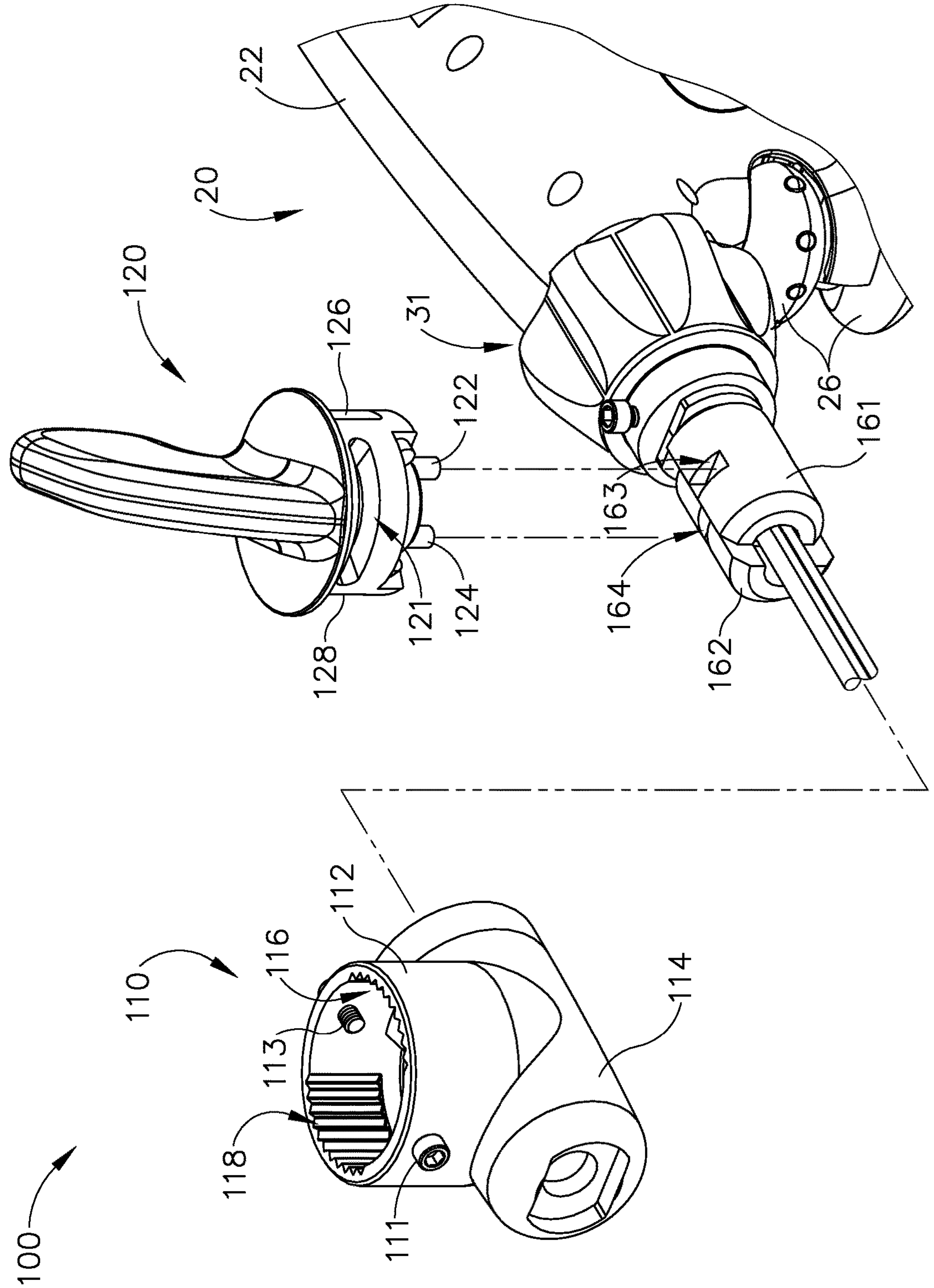
FIG. 7 depicts a partially exploded perspective view of an articulation control assembly of the instrument of FIG. 1.

As best seen in FIG. 7, an articulation control assembly (100) is secured to a proximal portion of outer sheath (32). Articulation control assembly (100) comprises a housing (110) and a rotatable knob (120). Housing (110) comprises a pair of perpendicularly intersecting cylindrical portions (112, 114). Knob (120) is rotatably disposed within a first hollow cylindrical portion (112) of housing (110) such that knob (120) is operable to rotate within cylindrical portion (112) of housing (110). Shaft assembly (30) is slidably and rotatably disposed within a second cylindrical portion (114). Shaft assembly (30) comprises a pair of translatable members (161, 162), both of which extend slidably and longitudinally through the proximal portion of outer sheath (32). Translatable members (161, 162) are longitudinally translatable within second cylindrical portion (114) between a distal position and a proximal position. Translatable members (161, 162) are mechanically coupled with respective articulation bands (140, 142) such that longitudinal translation of translatable member (161) causes longitudinal translation of articulation band (140), and such that longitudinal translation of translatable member (162) causes longitudinal translation of articulation band (142).

Knob (120) comprises a pair of pins (122, 124) extending downwardly from a bottom surface of knob (120). Pins (122, 124) extend into second cylindrical portion (114) of housing (110) and are rotatably and slidably disposed within a respective pair of channels (163, 164) formed in top surfaces of translatable members (161, 162). Channels (163, 164) are positioned on opposite sides of an axis of rotation of knob (120), such that rotation of knob (120) about that axis causes opposing longitudinal translation of translatable members (161, 162). For instance, rotation of knob (120) in a first direction causes distal longitudinal translation of translatable member (161) and articulation band (140), and proximal longitudinal translation of translatable member (162) and articulation band (142); and rotation of knob (120) in a second direction causes proximal longitudinal translation of translatable member (161) and articulation band (140), and distal longitudinal translation of translatable member (162) and articulation band (142). Thus, it should be understood that rotation of rotation knob (120) causes articulation of articulation section Housing (110) of articulation control assembly (100) comprises a pair of set screws (111, 113) extending inwardly from an interior surface of first cylindrical portion (112). With knob (120) rotatably disposed within first cylindrical portion (112) of housing (110), set screws (111, 113) are slidably disposed within a pair of arcuate channels (121, 123) formed in knob (120). Thus, it should be understood that rotation of knob (120) will be limited by movement of set screws (111, 113) within channels (121, 123). Set screws (111, 113) also retain knob (120) in housing (110), preventing knob (120) from traveling vertically within first cylindrical portion (112) of housing (110).

An interior surface of first cylindrical portion (112) of housing (110) comprises a first angular array of teeth (116) and a second angular array of teeth (118) formed in an interior surface of first cylindrical portion (112). Rotation knob (120) comprises a pair of outwardly extending engagement members (126, 128) that are configured to engage teeth (116, 118) of first cylindrical portion (112) in a detent relationship to thereby selectively lock knob (120) in a particular rotational position. The engagement of engagement members (126, 128) with teeth (116, 118) may be overcome by a user applying sufficient rotational force to knob (120); but absent such force, the engagement will suffice to maintain the straight or articulated configuration of articulation section (130). It should therefore be understood that the ability to selectively lock knob (120) in a particular rotational position lock will enable an operator to selectively lock articulation section (130) in a particular deflected position relative to the longitudinal axis defined by outer sheath (32).

In some versions of instrument (10), articulation section (130) of shaft assembly (30) is operable to achieve articulation angles up to between approximately 15° and approximately 30°, both relative to the longitudinal axis of shaft assembly (30) when shaft assembly (30) is in a straight (non-articulated) configuration. Alternatively, articulation section (130) may be operable to achieve any other suitable articulation angles.

In some versions of instrument (10), narrowed section (164) of waveguide (180) has a thickness between approximately 0.01 inches and approximately 0.02 inches. Alternatively, narrowed section (164) may have any other suitable thickness. Also in some versions, narrowed section (164) has a length of between approximately 0.4 inches and approximately 0.65 inches. Alternatively, narrowed section (164) may have any other suitable length. It should also be understood that the transition regions of waveguide (180) leading into and out of narrowed section (164) may be quarter rounded, tapered, or have any other suitable configuration.

In some versions of instrument (10), flanges (136, 138) each have a length between approximately 0.1 inches and approximately 0.2 inches. Alternatively, flanges (136, 138) may have any other suitable length. It should also be understood that the length of flange (136) may differ from the length of flange (138). Also in some versions, flanges (136, 138) each have a diameter between approximately 0.175 inches and approximately 0.2 inches. Alternatively, flanges (136, 138) may have any other suitable outer diameter. It should also be understood that the outer diameter of flange (136) may differ from the outer diameter of flange (138).

While the foregoing exemplary dimensions are provided in the context of instrument (10) as described above, it should be understood that the same dimensions may be used in any of the other examples described herein. It should also be understood that the foregoing exemplary dimensions are merely optional. Any other suitable dimensions may be used.

II. Exemplary Features to Provide Rigidization of Articulation Section

In some versions of instrument (10) it may be desirable to provide features that are configured to selectively provide rigidity to articulation section (130). For instance, because of various factors such as manufacturing tolerances, design limitations, material limitations, and/or other factors, some versions of articulation section (130) may be susceptible to some "play" or other small movement of the articulation section despite being relatively fixed in a given position, such that articulation section (130) is not entirely rigid. It may be desirable to reduce or eliminate such play in articulation section (130), particularly when articulation section (130) is in a straight, non-articulated configuration. Features may thus be provided to selectively rigidize articulation section (130). Various examples of features that are configured to selectively provide rigidity to articulation section (130) and/or to limit or prevent inadvertent deflection of end effector (40) will be described in greater detail below. Other examples will be apparent to those of ordinary skill in the art according to the teachings herein. It should be understood that the examples of shaft assemblies and/or articulation sections described below may function substantially similar to shaft assembly (30) discussed above.

It should also be understood that articulation section (130) may still be at least somewhat rigid before being modified to include the features described below, such that the features described below actually just increase the rigidity of articulation section (130) rather than introducing rigidity to an otherwise non-rigid articulation section (130). For instance, an articulation section (130) in the absence of features as described below may be rigid enough to substantially maintain a straight or articulated configuration; yet may still provide "play" of about 1 mm or a fraction thereof such that the already existing rigidity of articulation section (130) may be increased. Thus, terms such as "rigidize," "provide rigidity," and "providing rigidity" shall be understood to include just increasing rigidity that is already present in some degree. The terms "rigidize," "provide rigidity," and "providing rigidity" should not be read as necessarily requiring articulation section (130) to completely lack rigidity before the rigidity is "provided."

It should also be understood that "rigidizing" articulation section (130) may be viewed as more than merely locking articulation section (130). For instance, while articulating sections in some conventional instruments may include a locking feature that selectively locks the articulation section, such instruments may still demonstrate some degree of play in the articulation section, even when the articulation section purports to be in a locked state. By further "rigidizing" the articulation section as described herein, that play would be removed from the locked articulation section. Thus, terms such as "rigidizing" and "locking" should not be read as being synonymous.

Various examples of features that are configured to selectively rigidize articulation section (130) are described in greater detail below. Various other examples will be apparent to those of ordinary skill in the art in view of to the teachings herein.

A. Articulation Section with Movable Sheath

Figure 8:
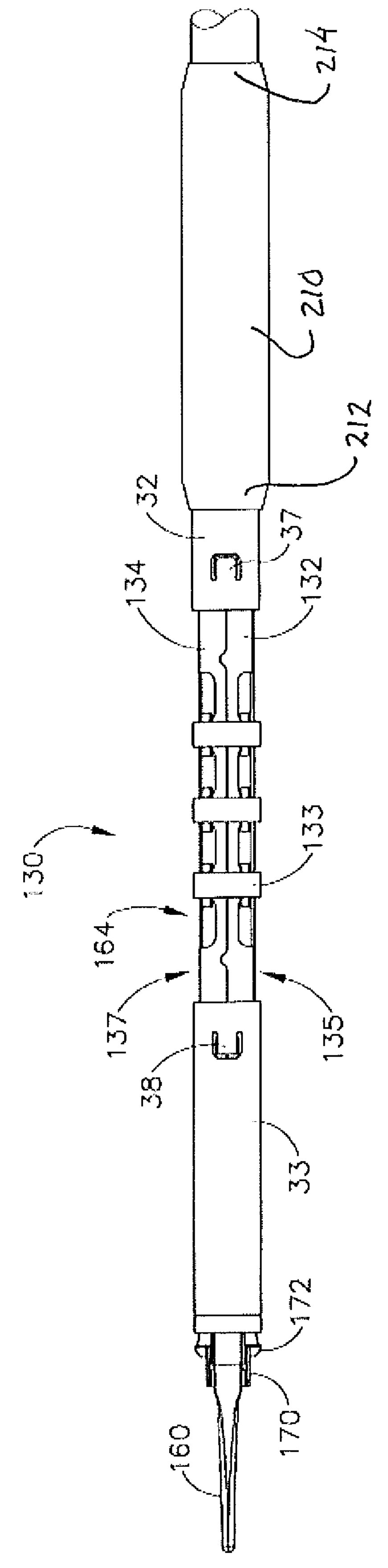
FIG. 8 depicts a top plan view of the shaft assembly and end effector of FIG. 2, including a movable sheath, with the sheath in a proximal position.
Figure 9:
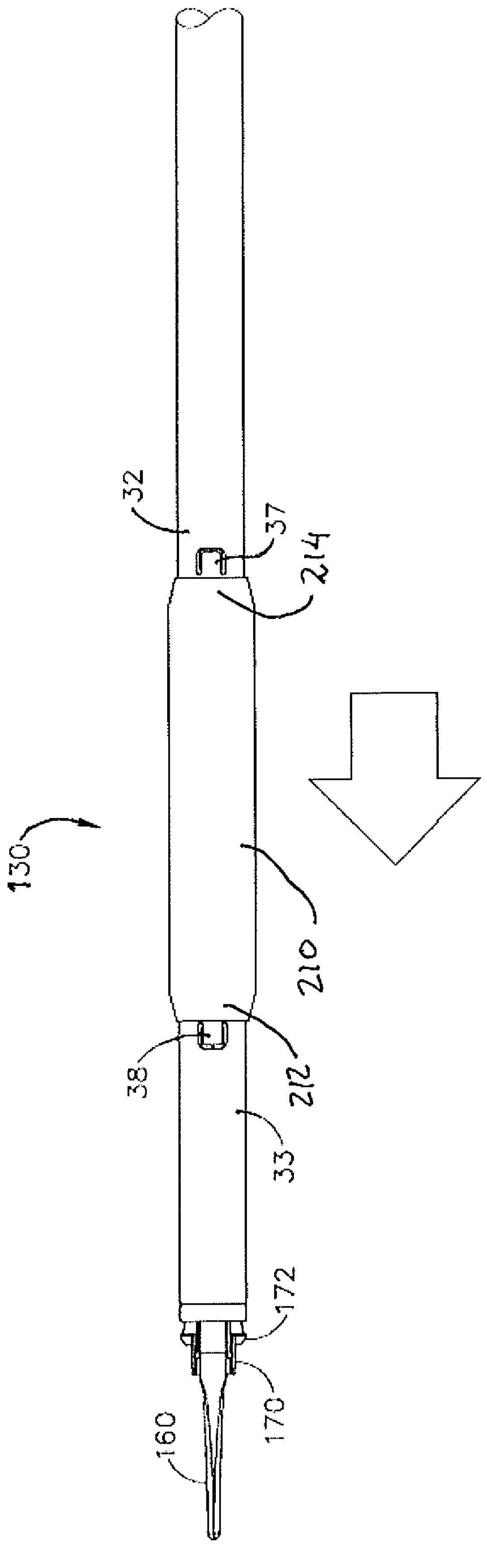
FIG. 9 depicts another top plan view of the shaft assembly and end effector of FIG. 2, with the movable sheath of FIG. 8 advanced to a distal position.

FIGS. 8 and 9 show a version of shaft assembly (30) that is modified to include a movable sheath (210), which is slidably disposed about proximal outer sheath (32). Sheath (210) is generally cylindrical in shape and is configured to fit over outer sheath (32). In particular, sheath (210) comprises a tapered open distal end (212) and a tapered open proximal end (214). Accordingly, sheath (210) is a generally hollow tube that surrounds outer sheath (32). Each end (212, 214) defines an inner diameter that is closely matched to the outer diameter of outer sheath (32). Such a relationship between the inner diameter of sheath (210) and outer sheath (32) may be desirable because such a relationship may prevent movement of articulation section (130) when sheath (210) is disposed over articulation section (130). Although the inner diameter of sheath (210) is similar to the outer diameter of outer sheath (32) it should be understood that the inner diameter of sheath (210) may still be large enough relative to the outer diameter of outer sheath (32) to permit sheath (210) to slide relative to outer sheath (32). As will be described in greater detail below, such slidability is desirable because it may permit sheath (210) to be selectively positioned over articulation section (130).

Sheath (210) is comprised of a generally rigid thin walled biocompatible material such as titanium, stainless steel, rigid plastic, and/or any other suitable material(s). Because distal and proximal ends (212, 214) of sheath (210) are tapered, the wall thickness of sheath (210) varies by length. Such a taper may prevent sheath (210) from being snagged on a trocar or other surgical port as shaft assembly (30) is inserted into and withdrawn from the trocar or other port. It should be understood that such a taper is merely optional, and in some examples sheath (210) may have a uniform thickness along the full length of sheath (210).

FIGS. 8 and 9 show an exemplary use of sheath (210). As can be seen in FIG. 8, sheath (210) may initially be disposed in a first position. In the first position, sheath (210) is disposed proximally of articulation section (130). In such a position, articulation section (130) is free to articulate as described above in response to an operator acting upon articulation control assembly (100).

When an operator desires to rigidize articulation section (130) in a fixed, straight position, an operator may do so by grasping sheath (210) and translating sheath (210) distally to the position shown in FIG. 9. The position shown in FIG. 9 corresponds to sheath (210) being in a second position. In the second position, sheath (210) is disposed over articulation section (130) with distal end (212) disposed over at least a portion of distal outer sheath (33) and proximal end (214) over at least a portion of proximal outer sheath (32). When in the second position, the inner diameter of sheath (210) engages distal outer sheath (33), articulation section (130) and proximal outer sheath (32) to prevent substantially all articulation and/or other movement of articulation section (130). In other words, sheath (210) rigidizes articulation section (130) when sheath (210) is disposed in the second position.

Although sheath (210) of the present example is described herein as being manually translatable by an operator, it should be understood that in other examples sheath (210) may be translatable by other means. For instance, in some examples sheath (210) may further comprise certain actuation components that are in communication with articulation bands (140, 142). In examples incorporating such actuation components, the actuation components are responsive to movement of articulation bands (140, 142) such that sheath (210) is automatically transitioned between the first and second positions by movement of articulation bands (140, 142) through certain predetermined positions. Additionally or in the alternative, sheath (210) may also be spring loaded to automatically transition sheath (210) from the first position to the second position. As yet another merely illustrative alternative, sheath (210) may be actuated by knob (120), some other user input feature at articulation control assembly (100), and/or some other feature of handle assembly (20). Still other suitable mechanisms for transitioning sheath (210) between the first and second positions will be apparent to those of ordinary skill in the art in view of the teachings herein.

B. Articulation Section with Movable Sheath and Sheath Securing Features

Figure 10:
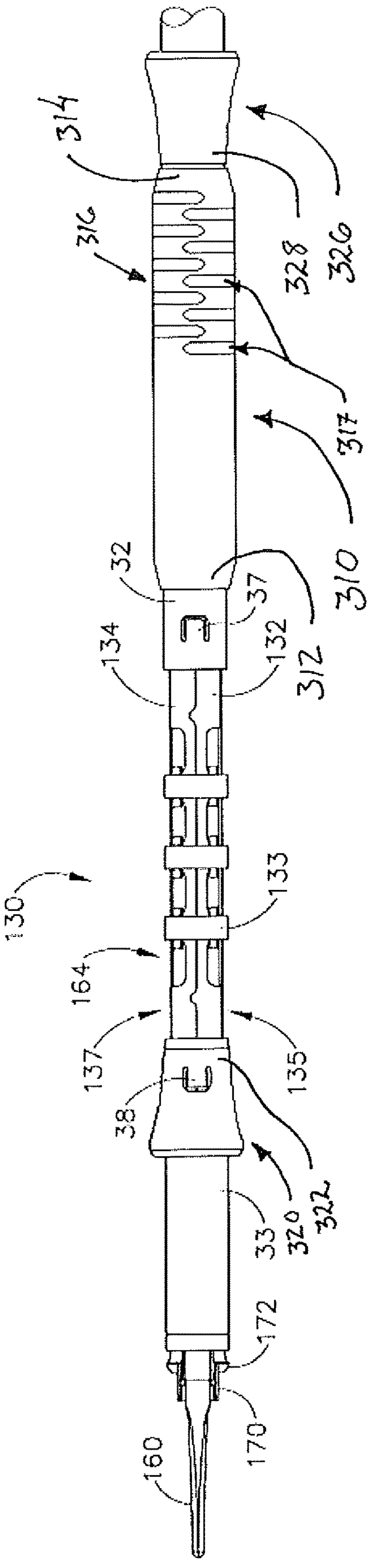
FIG. 10 depicts a top plan view of the shaft assembly and end effector of FIG. 2, including an exemplary alternative movable sheath, with the sheath in a first position.
Figure 11:
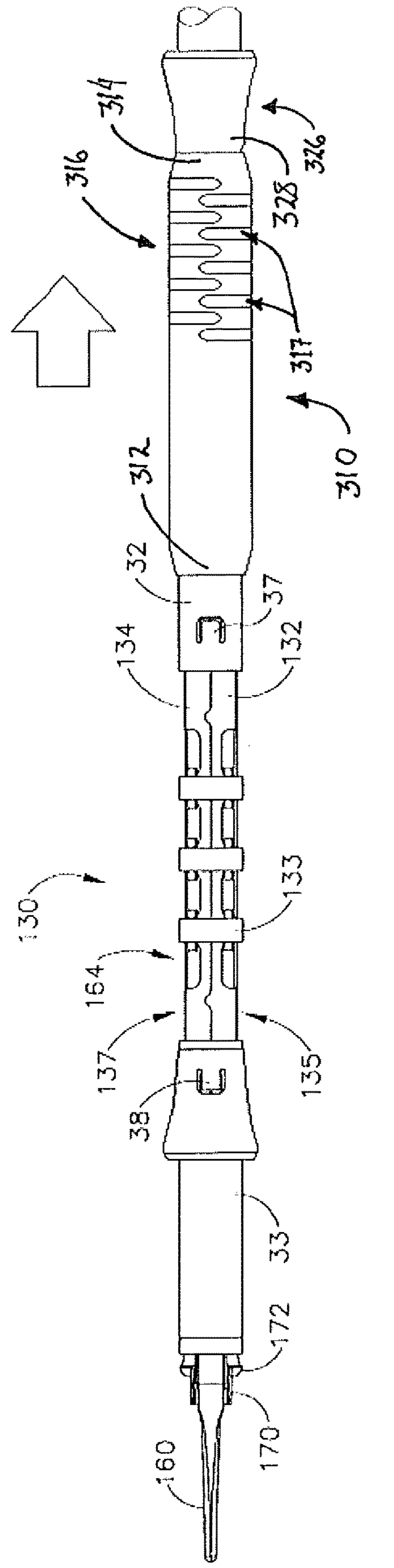
FIG. 11 depicts another top plan view of the shaft assembly and end effector of FIG. 2, with the movable sheath of FIG. 10 retracted to a second position.
Figure 12:
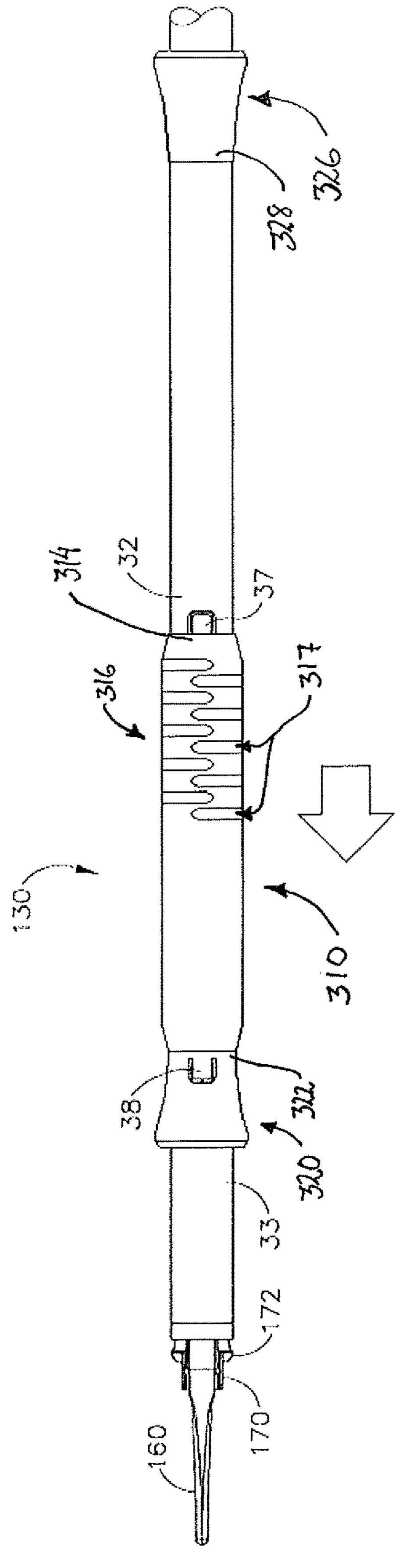
FIG. 12 depicts still another top plan view of the shaft assembly and end effector of FIG. 2, with the movable sheath of FIG. 10 advanced to a third position.

FIGS. 10-12 show a version of shaft assembly (30) that is modified to include another movable sheath (310), which is slidably disposed about proximal outer sheath (32). Sheath (310) is generally cylindrical in shape and is configured to fit over outer sheath (32). In particular, sheath (310) comprises a tapered open distal end (312), a tapered open proximal end (314), and a grip portion (316) disposed distally of proximal end (314). Accordingly, sheath (310) is a generally hollow tube that surrounds outer sheath (32). Each end (312, 314) defines an inner diameter of sheath (310) that is closely matched to the outer diameter of outer sheath (32). Such a relationship between the inner diameter of sheath (310) and outer sheath (32) may be desirable because such a relationship may prevent movement of articulation section (130) when sheath (310) is disposed over articulation section (130). Although the inner diameter of sheath (310) is similar to the outer diameter of outer sheath (32) it should be understood that the inner diameter of sheath (310) may still be large enough relative to the outer diameter of outer sheath (32) to permit sheath (310) to slide relative to outer sheath. As will be described in greater detail below, such slidability is desirable because it may permit sheath (310) to be selectively positioned over articulation section (130).

Grip portion (316) is generally configured to facilitate grasping of sheath (310) by an operator. Grip portion (316) of sheath comprises a plurality of grip features (317). Grip features (317) of the present example are shown as spaced-apart indentations in the outer diameter of sheath (310). In other examples, grip features (317) are formed by integral protrusions or separately secured protrusions. In examples utilizing protrusions, it should be understood that the protrusions protrude from sheath (310) may be fixed by the inner diameter of a trocar or other port that instrument (10) may be used in conjunction with. It should also be understood that grip portion (312) is merely optional, such that grip portion (312) is omitted in some versions.

Sheath (310) is comprised of a generally rigid thin walled biocompatible material such as titanium, stainless steel, rigid plastic, or etc. Because distal and proximal ends (312, 314) of sheath (310) are tapered, the wall thickness of sheath (310) varies by length. Such a taper may prevent sheath (310) from being snagged on a trocar or other surgical port as shaft assembly (30) is inserted into and withdrawn from the trocar or other port. It should be understood that such a taper is merely optional, and in some examples sheath (310) may have a uniform thickness along the full length of sheath (310).

Distal outer sheath (33) and proximal outer sheath (32) in the present example each include a flared stop member (320, 326). In particular, a distal stop member is positioned on distal outer sheath (33) and a proximal stop member (326) is positioned on proximal outer sheath (33). Each stop member (320, 326) is unitarily secured to the corresponding sheath (32, 33). Each stop member (320, 326) is generally frustoconical in shape, with a maximum outer diameter that is greater than the inner diameter of sheath (310) such that stop members (320, 326) are configured to engage with sheath (310) and thereby restrict longitudinal movement of sheath (310). In the present example, each stop member (320, 326) is overmolded onto each respective sheath (32, 33) and comprises a resilient material such as a soft plastic or rubber. In some other examples, each stop members (320, 326) is unitarily formed with each respective sheath (32, 33).

As will be described in greater detail below, sheath (310) is generally slidable and into engagement with either distal stop member (320) or proximal stop member (326). Thus, distal stop member (320) is positioned such that an engagement end (322) is positioned proximally, while proximal stop member (326) is positioned such that an engagement end (328) is positioned distally. Engagement end (322) is sized for snug receipt within sheath (310), such that distal stop member (320) may releasably hold sheath (310) in a distal position through friction between engagement end and the interior of sheath (310). Similarly, engagement end (328) is sized for snug receipt within sheath (310), such that proximal stop member (326) may releasably hold sheath (310) in a proximal position through friction between engagement end and the interior of sheath (310). The enlarged distal end of distal stop member (320) will restrict distal movement of sheath (310), while the enlarged proximal end of proximal stop member (326) will restrict proximal movement of sheath (310).

FIGS. 10-12 show an exemplary use of sheath (310). As can be seen in FIG. 10, sheath (310) may initially be disposed in a first position. In the first position, sheath (310) is disposed proximally of articulation section (130) yet distally of proximal stop member (326). In such a position, articulation section (130) is free to articulate as described above in response to an operator acting upon articulation control assembly (100). Further, sheath (310) is free from both stop members (320, 326) such that sheath (310) is freely movable between stop members (320, 326).

When sheath (310) is in the first position, an operator may optionally lock sheath (310) in a second position, or advance sheath (310) to a third position. FIG. 11 shows sheath (310) in the second position. As can be seen, the second position corresponds to sheath (310) being disposed over proximal outer sheath (32) and engaged with proximal stop member (326). It should be understood that the second position corresponds to the furthest proximal position of sheath (310). In particular, stop member (326) prevents further proximal movement of sheath (310). Additionally, stop member (326) resiliently locks sheath (310) in position by resiliently engaging the inner diameter of sheath (310). In other words, sheath (310) compresses engagement end (328) and thereby creates friction that releasably holds sheath (310) in place.

When an operator desires to rigidize articulation section (130) in a fixed, straight position, the operator may do so by grasping sheath (310) and translating sheath (310) distally to the position shown in FIG. 12 from either the first position or the second position. The position shown in FIG. 12 corresponds to sheath (310) being in the third position. In the third position, sheath (310) is disposed over articulation section (130) with distal end (312) disposed over at least a portion of distal outer sheath (33) and proximal end (314) over at least a portion of proximal outer sheath (32). Additionally, distal end (312) engages at least a portion of distal stop member (320). Sheath (310) compresses engagement end (322) and thereby creates friction that releasably holds sheath (310) in place. In addition, stop member (320) prevents further distal movement of sheath (310). When in the third position, the inner diameter of sheath (310) engages distal outer sheath (33), articulation section (130), and proximal outer sheath (32) to prevent substantially all articulation and/or movement of articulation section (130). In other words, sheath (310) rigidizes articulation section (130) when sheath (310) is disposed in the third position.

Like with sheath (210) described above, sheath (310) of the present example may also be translatable by other non-manual means. For instance, in some examples sheath (310) may further comprise certain actuation components that are in communication with articulation bands (140, 142). In examples incorporating such actuation components, the actuation components are responsive to movement of articulation bands (140, 142) such that sheath (310) is automatically transitioned between the first and second positions by movement of articulation bands (140, 142) through certain predetermined positions. Additionally or in alternative, sheath (310) may also be spring loaded to automatically transition sheath (310) from the first position to the second position. As yet another merely illustrative alternative, sheath (310) may be actuated by knob (120), some other user input feature at articulation control assembly (100), and/or some other feature of handle assembly (20). Still other suitable mechanisms for transitioning sheath (310) between the first and second positions will be apparent to those of ordinary skill in the art in view of the teachings herein.

C. Articulation Section with Rotatable Locking Sheath

Figure 13:
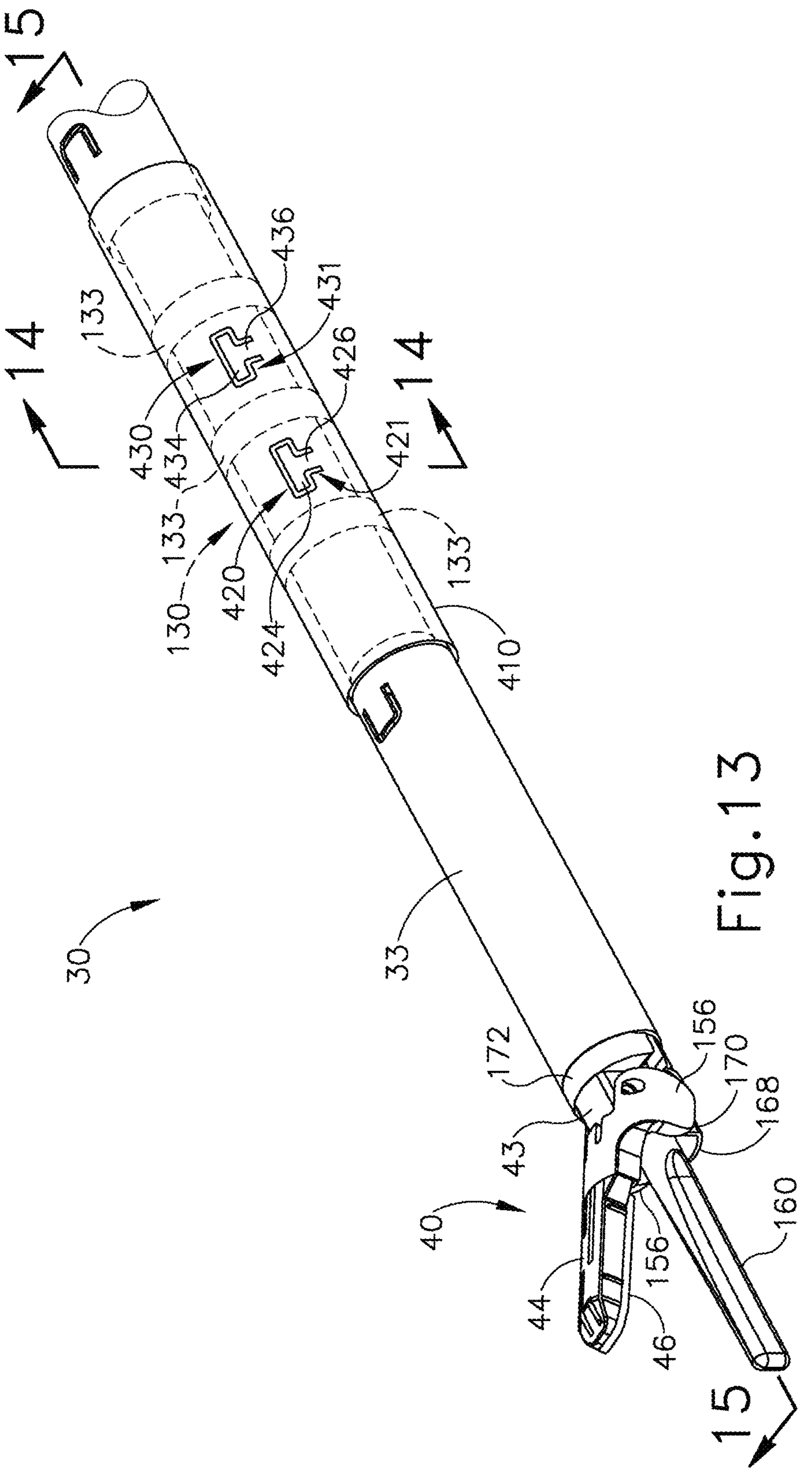
FIG. 13 depicts a perspective view of the articulation section of FIG. 2, the articulation section including a rotatable sheath, with the sheath in a first angular position.
Figure 14:
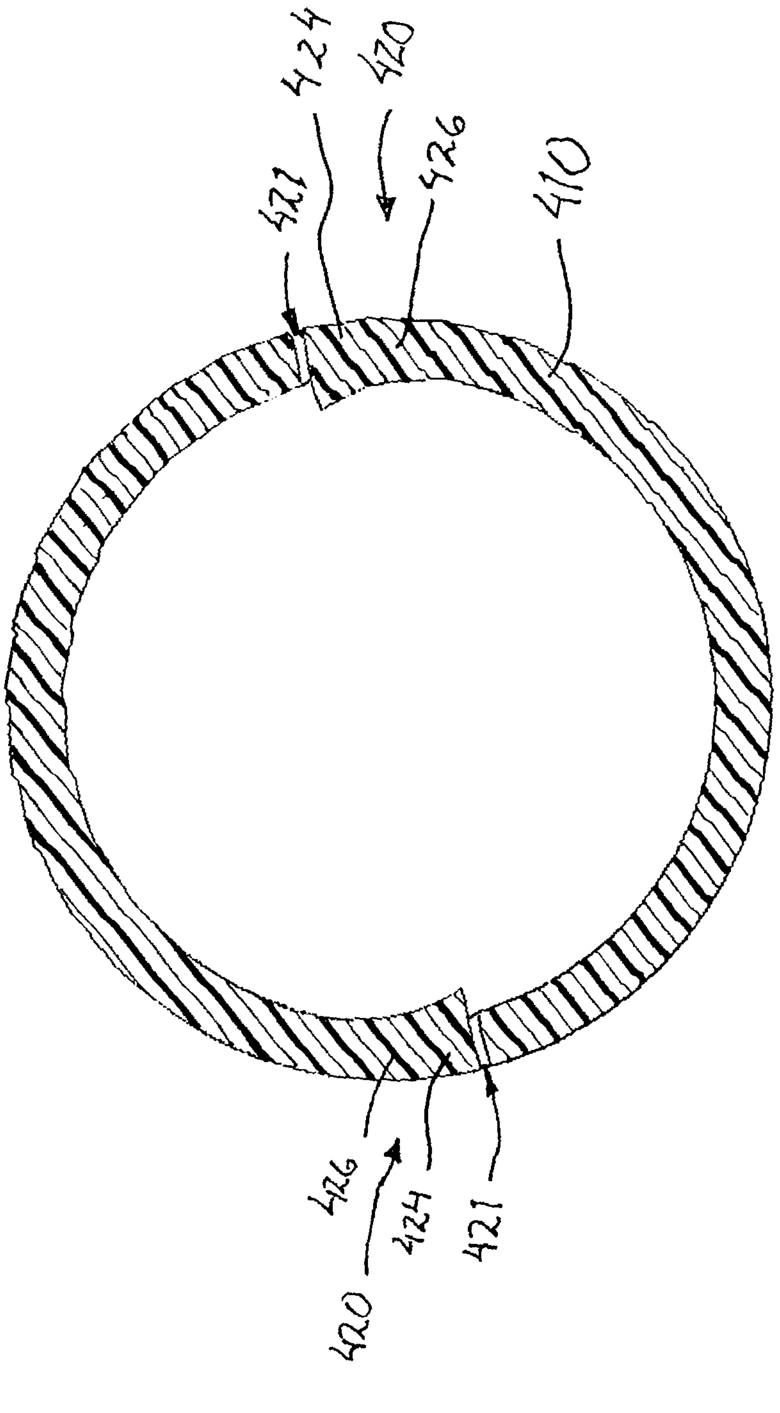
FIG. 14 depicts a front cross-sectional view of the rotatable sheath of FIG. 13, the cross-section taken along line 14-14 of FIG. 13.

FIGS. 13-17 show a version of shaft assembly (30) that is modified to include a rotatable sheath (410), which is rotatably disposed about articulation section (130). Rotatable sheath (410) is generally tubular in structure and comprises two tab members (420, 430) of unitary construction with sheath (410). Tab members (420, 430) are formed by slits (420, 430) cut (421, 431) within sheath (410) to define a longitudinal portion (424, 434) and a transverse portion (426, 436) of each tab member (420, 430), such that each tab member (420, 430) has a "T" shape. As can be seen in FIG. 14, the thickness of each tab member (420, 430) expands from transverse portion (426, 436) to longitudinal portion (424, 434) such that at least a portion of each tab member (420, 430) extends into the inner diameter of sheath (410). As will be described in greater detail below, the increased thickness of each longitudinal portion (424, 434) is configured to engage with retention collars (133) of articulation section (130) to prevent articulation of articulation section (130). In some versions, each tab member (420, 430) has a uniform thickness and tab members (420, 430) are simply resiliently biased to extend inwardly into the inner diameter of sheath (410). For instance, transverse portions (426, 436) may be bent inwardly to resiliently position longitudinal portions (424, 434) into the inner diameter of sheath (410).

Sheath (410) further comprises a generally flexible material such that sheath (410) is configured to bend as articulation section (130) is articulated. Although the material of sheath (410) is generally flexible, it should also be understood that the material of sheath (410) is somewhat rigid. As will be described in greater detail below, tab members (420, 430) are configured to engage retention collars (133) of articulation section (130) to selectively prevent articulation of articulation section (130). Accordingly, sheath (410) is comprised of a material of sufficient column strength such that tab members (420, 430) resist buckling when compressed between retention collars (133). Sheath (410) may comprise any suitable material such as biocompatible polymers and/or any other material(s) as will be apparent to those of ordinary skill in the art in view of the teachings herein.

Figure 15:
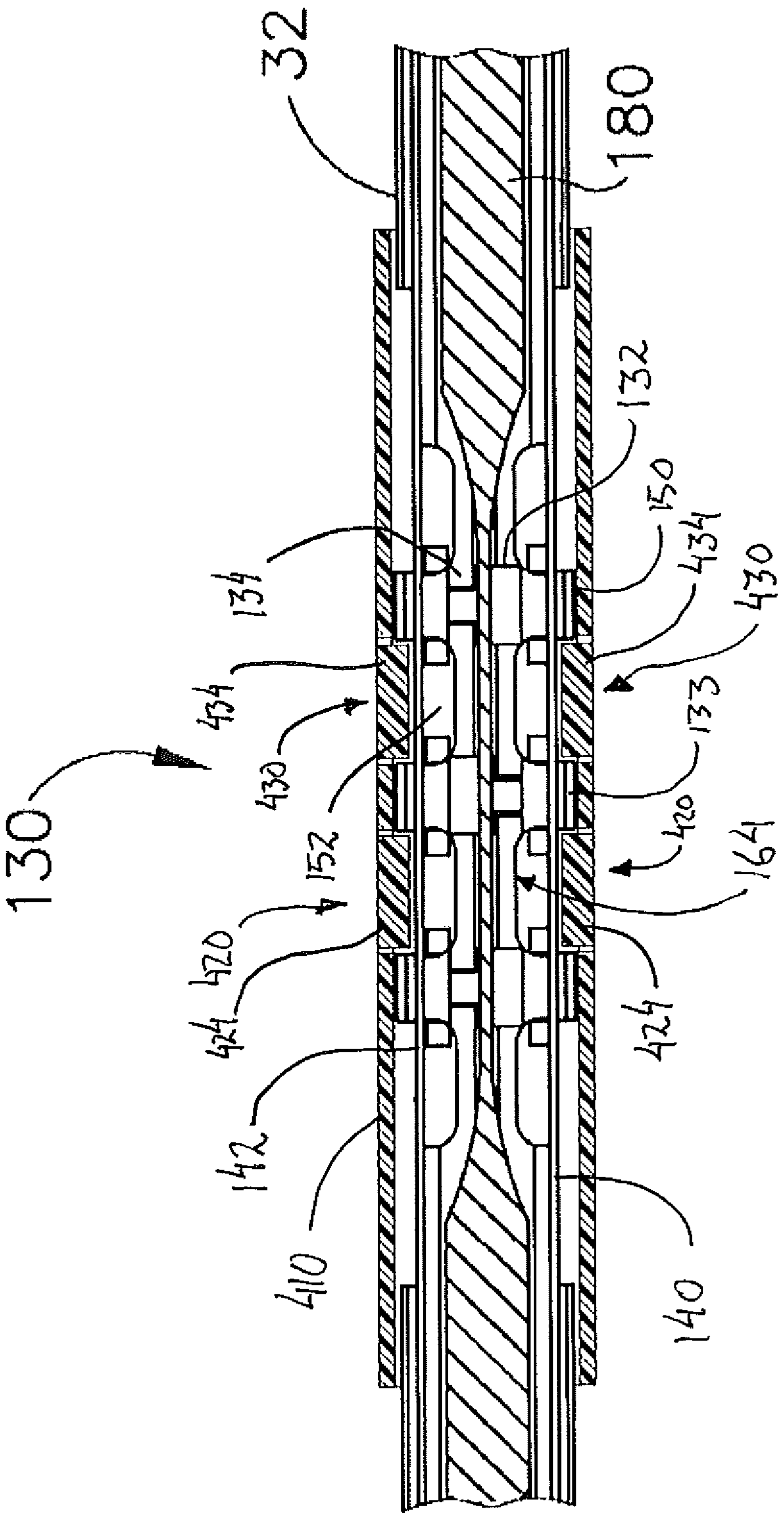
FIG. 15 depicts a top cross-sectional view of the articulation section and rotatable sheath of FIG. 13, the cross-section taken along line 15-15 of FIG. 13.

FIGS. 13, 15, and 16-17 show an exemplary use of sheath (410). In particular, as can be seen in FIGS. 13 and 15, sheath (410) is initially in a first angular position. When sheath (410) is in the first angular position, longitudinal portions (424, 434) of each tab member (420, 430) are aligned with an articulation plane through which the central longitudinal axis of shaft assembly (30) articulates. As can best be seen in FIG. 15, when sheath (410) is in the first position, longitudinal portions (424, 434) of each tab member (420, 430) are positioned between each retention collar (133) along the articulation plane. Accordingly, longitudinal portions (424, 434) are positioned to block any articulation of articulation section (130) because longitudinal portions (424, 434) prevent retention collars (133) from moving closer to one another. Therefore, sheath (410) acts as a locking member to increase the rigidity of articulation section (130) when sheath (410) is in the first angular position.

Figure 16:
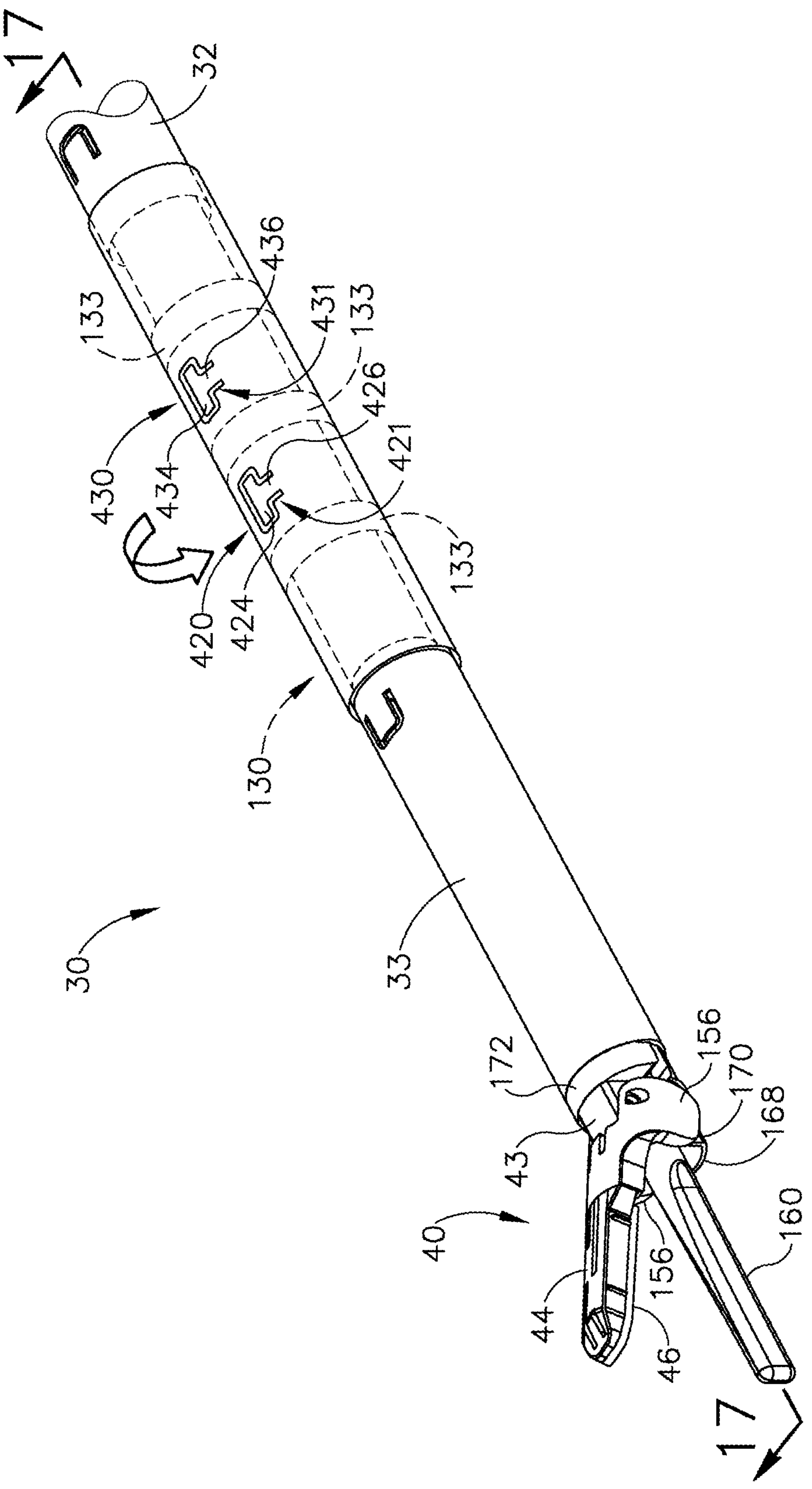
FIG. 16 depicts another perspective view of the articulation section of FIG. 2, with the rotatable sheath of FIG. 13 rotated to a second angular position.
Figure 17:
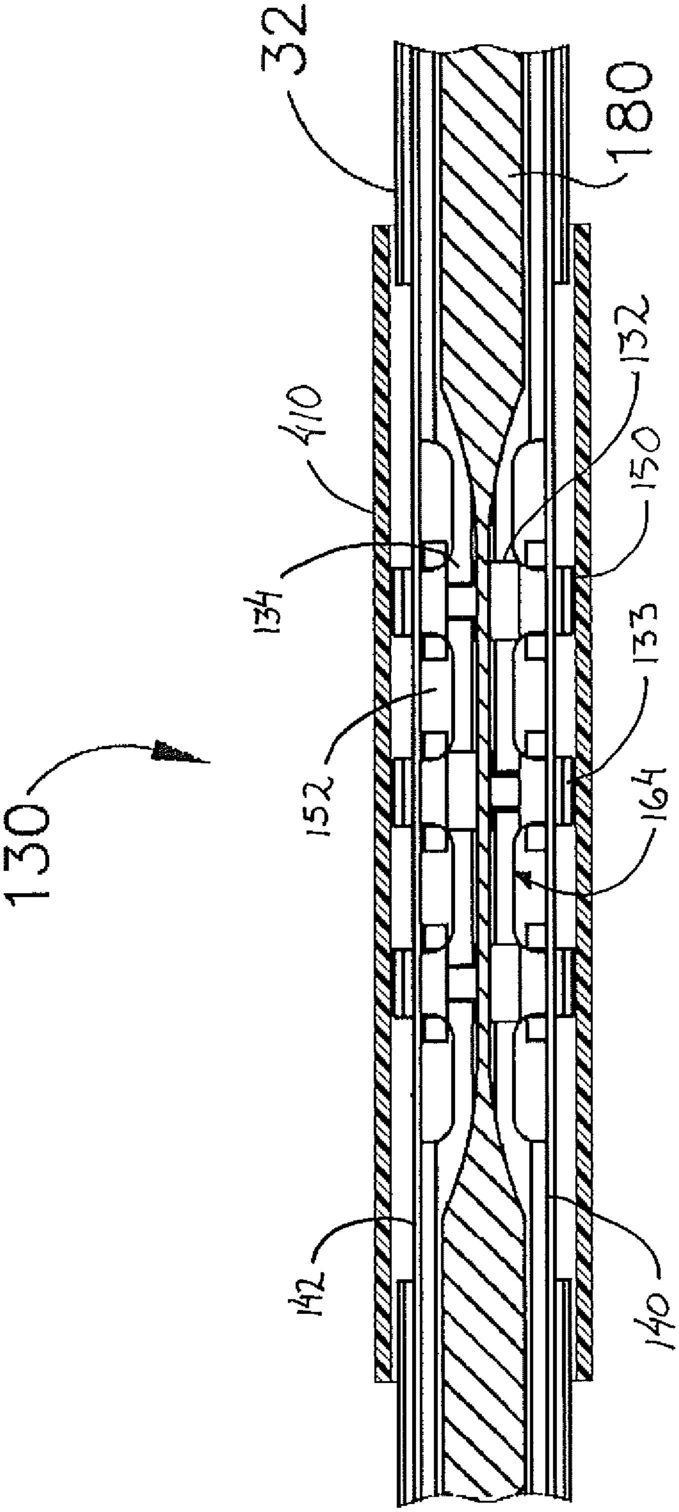
FIG. 17 depicts a top cross-sectional view of the articulation section and rotatable sheath of FIG. 13, with the cross-section taken along line 17-17 of FIG. 16 and the sheath in the second angular position.

To unlock articulation section (130) for articulation, an operator may rotate sheath (410) 90° about the longitudinal axis of shaft assembly (30), relative to the rest of shaft assembly (30), to a second angular position. As can be seen in FIGS. 16 and 17, when sheath (410) is in the second angular position, longitudinal portions (424, 434) are oriented perpendicularly from the articulation plane of articulation section (130). Thus, although longitudinal portions (424, 434) remain disposed between retention collars (133) of articulation section (130), articulation section (130) is permitted to articulate because longitudinal portions (424, 434) are not positioned to block movement of retention collars (133) along the articulation plane as articulation section (130) is articulated. Moreover, because sheath (410) is relatively flexible, sheath (410) itself does not prevent articulation of articulation section (130). Therefore, sheath (410) acts to permit articulation of articulation section (130) when sheath (410) is in the second angular position.

By way of example only, an operator may selectively transition sheath (410) between the first and second angular positions by simply grasping sheath (410) and rotating sheath (410) about the longitudinal axis of shaft assembly (30) while holding the rest of shaft assembly (30) stationary. Alternatively, sheath (410) may be actuated between the first and second angular positions via a user input feature that is incorporated into articulation control assembly (100) and/or some other feature of handle assembly (20). Various suitable ways in which sheath (410) may be actuated will be apparent to those of ordinary skill in the art in view of the teachings herein.

Figure 18:
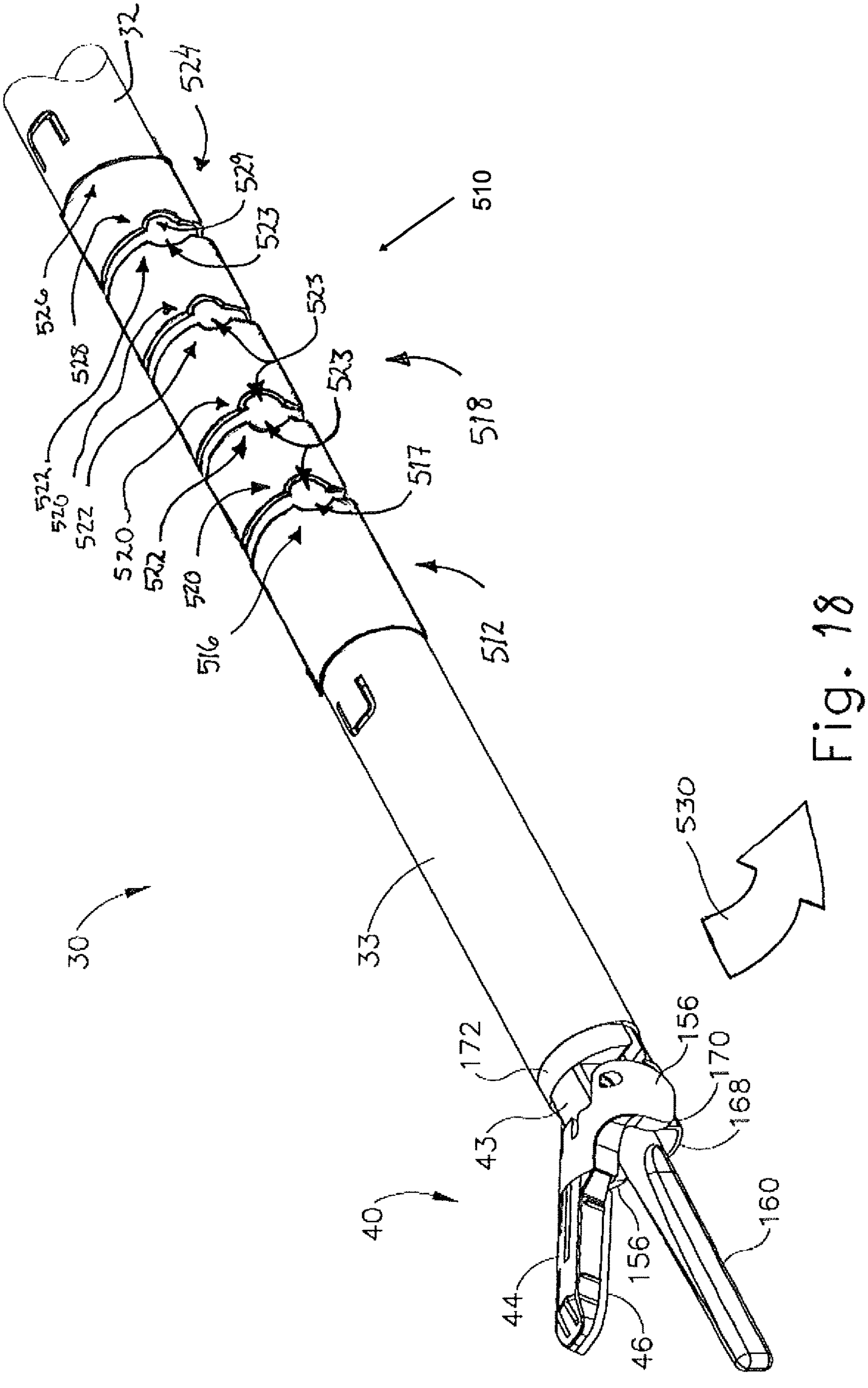
FIG. 18 depicts a perspective view of the articulation section of FIG. 2, the articulation section including an exemplary alternative rotatable sheath, with the sheath in a first angular position.

FIG. 18 shows an exemplary alternative sheath (510) that operates similarly to sheath (410) and may be readily incorporated into shaft assembly (30) of instrument (10). In the present example, sheath (510) is positioned over articulation section (130) as described above. In some versions, retention collars (133) are omitted when sheath (510) is incorporated into shaft assembly (30). As can be seen, sheath (510) is comprised of a plurality of segments (512, 518, 524) that are disposed over articulation section (130). In particular, segments (512, 518, 524) form a generally tubular structure that is configured to bend in a single lateral direction as indicated by arrow (530), but resist bending in other directions that are generally oblique or perpendicular to arrow (530).

Segments (512, 518, 524) of the present example comprise two end segments (512, 524) and three intermediate segments (518). Each end segment (512, 524) includes an end portion (514, 526) and a connecting portion (516, 528). End portions (514, 526) are generally circular in cross-section and are configured to receive distal outer sheath (33) and proximal outer sheath (32), respectively. Connecting portions (516, 528) are configured to abut a corresponding intermediate segment (518). Each connecting portion (516, 528) defines an indentation (517, 529) therein. As will be described in greater detail below, each indentation (517, 529) is generally configured to cooperate with corresponding indentation (523) of an adjacent intermediate segment (518) to thereby permit articulation of sheath (510) along the lateral direction indicated by arrow (530).

Each intermediate segment (518) of the present example is substantially the same. Although the present example is shown as comprising three intermediate segments (518), it should be understood that any suitable number of intermediate segments (518) may be used. Further, in some examples intermediate segments (518) may be omitted and end segments (512, 524) may simply be adjacent to each other. Each intermediate segment (518) is generally symmetrical with a distal portion (520) and a proximal portion (522). Each portion (520, 522) defines an indentation (523) and abuts a corresponding adjacent segment (512, 518, 524). Each indentation (523) is aligned with either an adjacent indentation (523) of another intermediate segment (518) or an adjacent indentation (517, 529) of end segments (512, 524).

Segments (512, 518, 524) are connected to each other sequentially to form the tubular structure of sheath (510). Segments (512, 518, 524) are connected to each other such that each segment (512, 518, 524) is movable relative to an adjacent segment (512, 518, 524). For instance, suitable connections may include wire connections, thin walled flexible integral members, hinge members, or any other suitable structures as will be apparent to those of ordinary skill in the art in view of the teachings herein. Regardless of the particular connection used, each segment (512, 518, 524) is aligned with an adjacent segment (512, 518, 524) such that all indentations (517, 523, 529) are aligned with each other along a linear path that is generally parallel to the longitudinal axis of shaft assembly (30). It should be understood that the alignment of indentations (517, 523, 529) may permit flexibility of sheath (510) along the linear path of alignment because each indentation (517, 523, 529) provides space for each segment to pivot relative to the other. In contrast, where each segment (512, 518, 524) abuts another without the presence of indentation (517, 523, 529), flexibility of sheath (510) is blocked because each segment (512, 518, 524) has little to no space to move relative to other segments (512, 518, 524).

Figure 19:
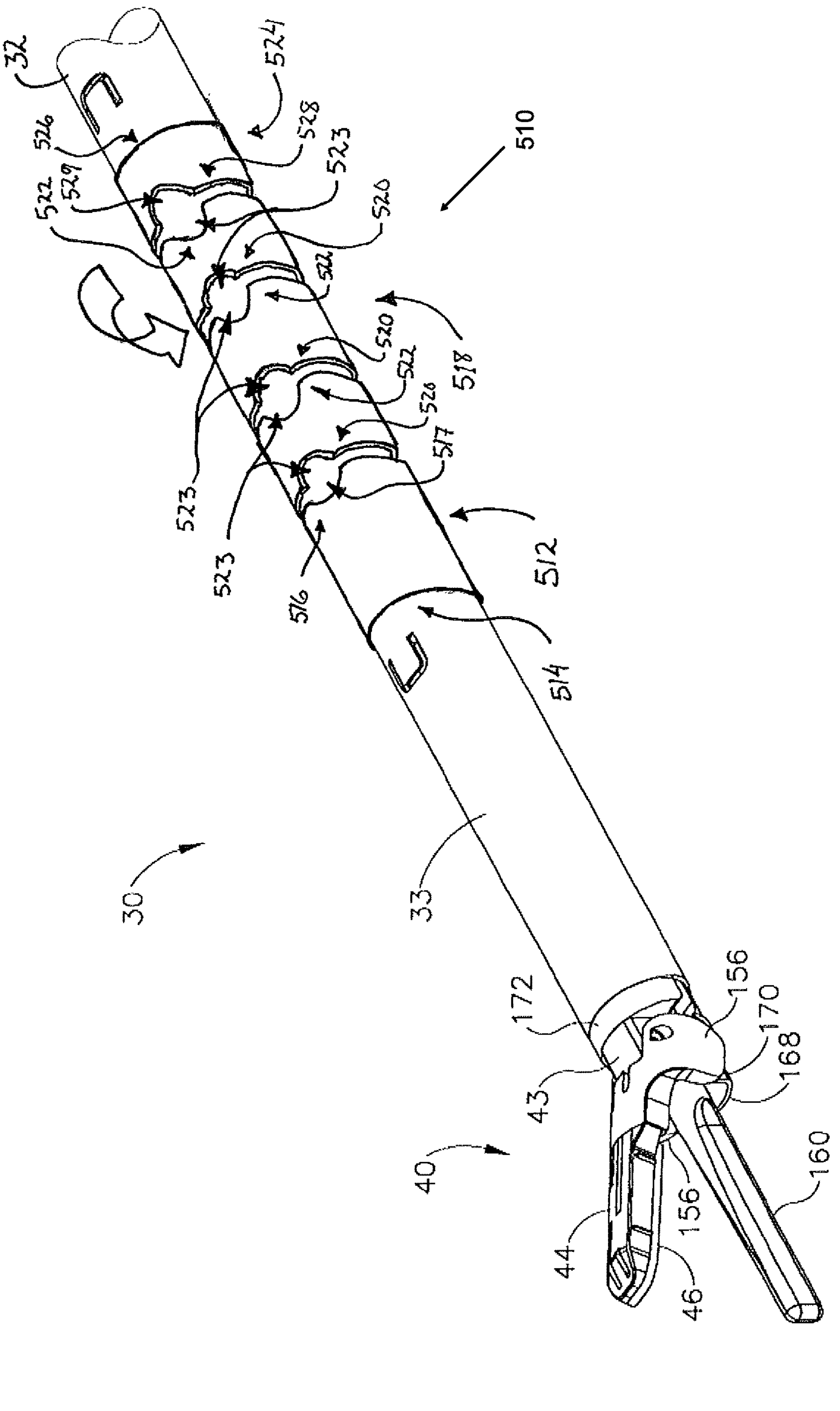
FIG. 19 depicts another perspective view of the articulation section and rotatable sheath of FIG. 18, with the sheath rotated to a second angular position.

FIGS. 18 and 19 show an exemplary use of sheath (510). In particular, FIG. 18 shows sheath (510) in a first angular position. In the first angular position, indentations (517, 523, 529) of each segment (512, 518, 524) of sheath (510) are aligned along the articulation plane of shaft assembly (30) as indicated by arrow (530). Thus, when sheath (510) is in the first position, sheath (510) permits articulation of articulation section (130). To articulate articulation section (130), an operator may actuate articulation control assembly (100) as described above.

Once an operator desires to lock articulation section (130) in a straight position, the operator may first transition articulation section (130) to the straight configuration using articulation control assembly (100) as described above. Once articulation section (130) is in the straight configuration, the operator may rotate sheath (510) 90° about the longitudinal axis of shaft assembly (30), relative to the rest of shaft assembly (30), to a second angular position as shown in FIG. 19. As can be seen, when sheath (510) is rotated to the second angular position, indentations (517, 523, 529) of each segment (512, 518, 524) of sheath (510) are aligned in a position that is normal to the articulation plane of shaft assembly (30). As described above, sheath (510) is only bendable in the direction of indentations (517, 523, 529). Accordingly, when indentations (517, 523, 529) are positioned normal to the articulation plane of shaft assembly (30), sheath (510) prevents articulation of articulation section (130) because segments (512, 518, 524) are incapable of moving relative to each other along the articulation plane of articulation section (130) when sheath (510) is in the second angular position. Therefore, when sheath (510) is positioned in the second angular position, articulation section (130) is locked from articulation and/or increased in rigidity due to the angular positioning of sheath (510).

By way of example only, an operator may selectively transition sheath (510) between the first and second angular positions by simply grasping sheath (510) and rotating sheath (510) about the longitudinal axis of shaft assembly (30) while holding the rest of shaft assembly (30) stationary. Alternatively, sheath (510) may be actuated between the first and second angular positions via a user input feature that is incorporated into articulation control assembly (100) and/or some other feature of handle assembly (20). Various suitable ways in which sheath (510) may be actuated will be apparent to those of ordinary skill in the art in view of the teachings herein.

D. Articulation Section with Complementary Locking Shafts

Figure 20:
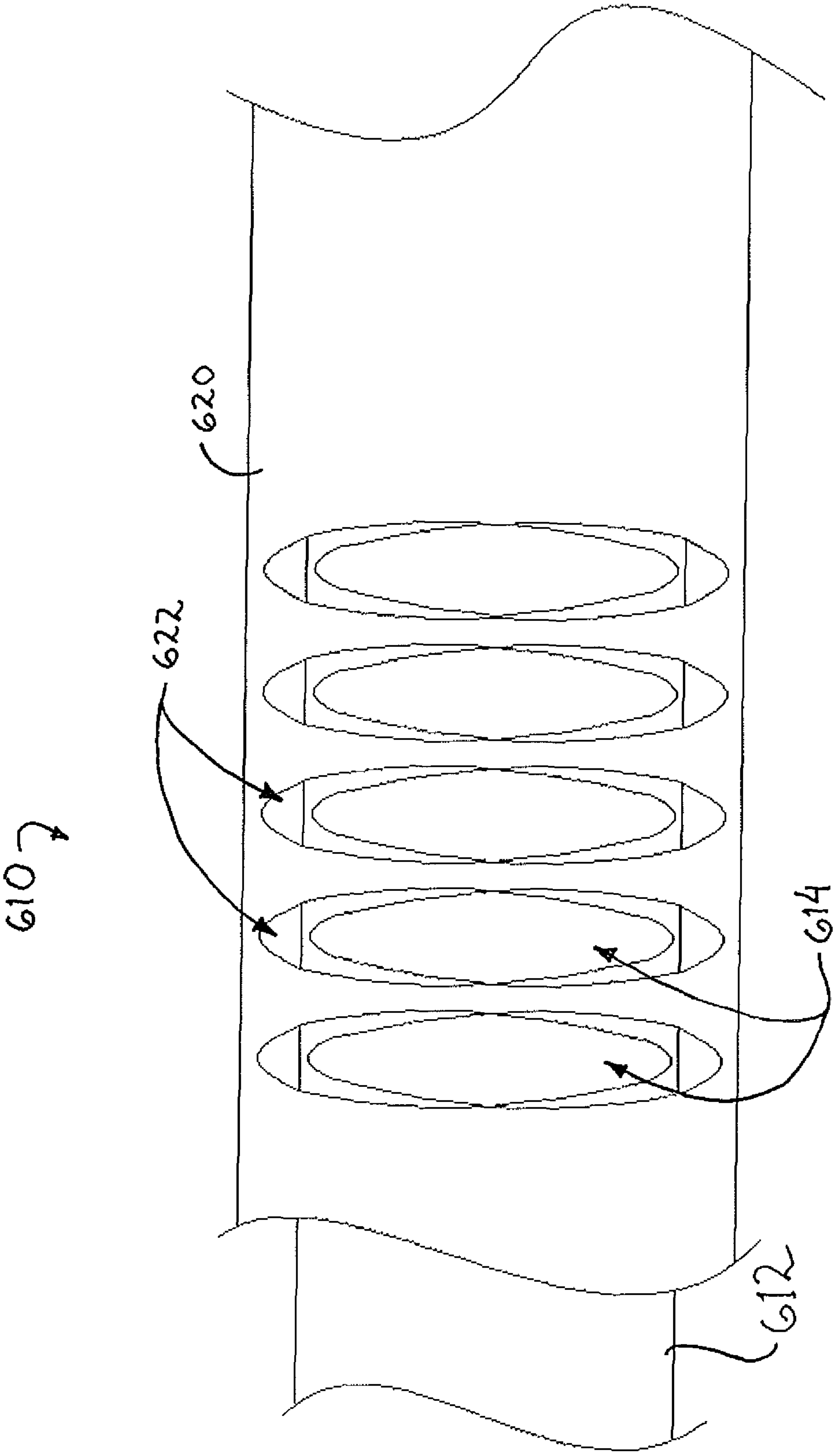
FIG. 20 depicts a side elevational view of an exemplary alternative sheath assembly that may be incorporated into the instrument of FIG. 1, with an outer sheath in a first angular position.
Figure 21:
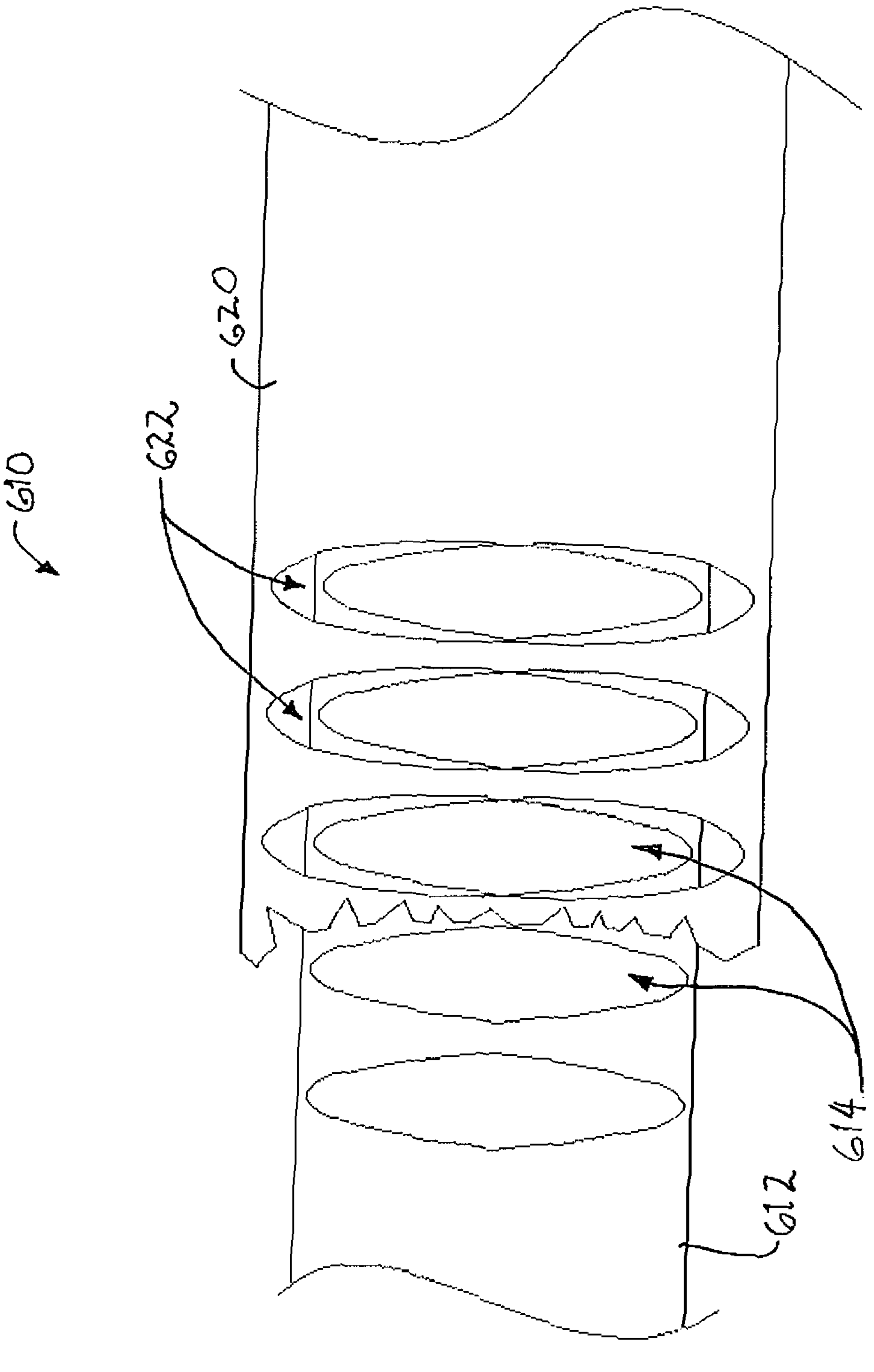
FIG. 21 depicts a side cut-away view of the sheath assembly of FIG. 20.
Figure 22:
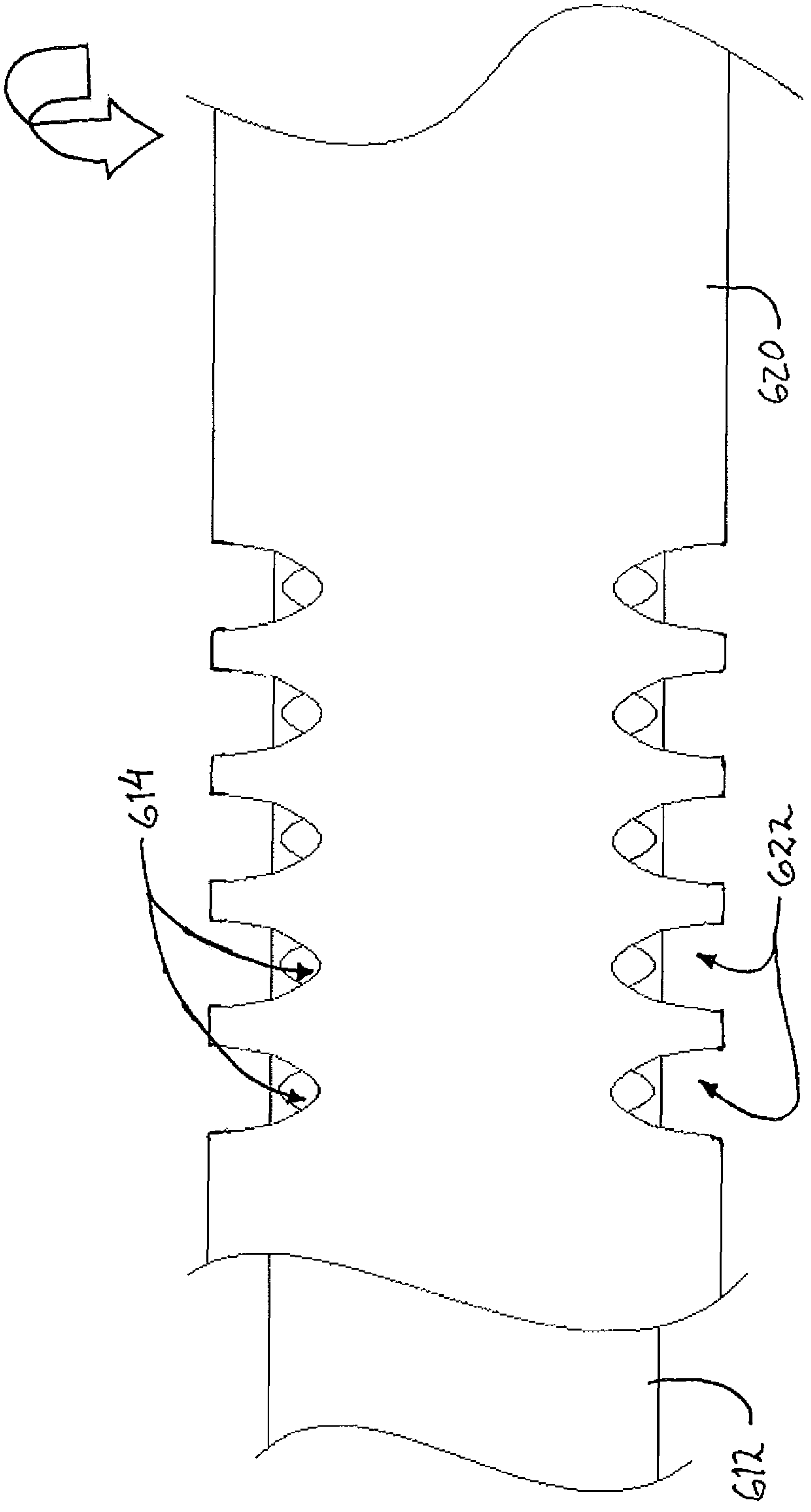
FIG. 22 depicts another side elevational view of the sheath assembly of FIG. 20, with the outer sheath rotated to a second angular position.

FIGS. 20-22 show an exemplary alternative sheath assembly (610) that may be readily incorporated into shaft assembly (30) described above. In examples where sheath assembly (610) is incorporated into shaft assembly (30), sheath assembly (610) may be disposed around articulation section (130) to thereby selectively rigidize articulation section (130). Sheath assembly (610) is longitudinally fixed about articulation section (130). Sheath assembly (610) comprises an inner sheath (612) disposed coaxially within an outer sheath (620). As will be described in greater detail below, sheaths (612, 620) are configured to cooperate to selectively rigidize articulation section (130). In the present example sheaths (612, 620) are each about 0.0075" thick, although any suitable thickness may be used. For instance, in some examples sheaths (612, 620) range from about 0.005" to about 0.010" in wall thickness.

As can be seen in FIG. 20 outer sheath (620) comprises a plurality of openings (622) on the exterior of outer sheath (620). In particular, openings (622) are all substantially the same and have an elongate ovular or elliptical shape. As will be described in greater detail below, openings (622) are generally configured to locally increase the flexibility of outer sheath (620) in the region of outer sheath (620) where openings (622) are positioned. Although not shown, it should be understood that openings (622) extend laterally though outer sheath (620) and thus are also disposed on the opposite outer wall of outer sheath (620). Such a feature is configured to increase the local flexibility of outer sheath (620) because openings (622) on one side may expand while openings (622) on another side may contract as outer sheath (620) bends along an articulation plane. It should be understood that openings (620) are configured to allow outer sheath (620) to bend along just one plane.

As best seen in FIG. 21, inner sheath (612) also comprises a plurality of openings (614) on the exterior of inner sheath (612). Openings (614) are similar to openings (622) described above. For instance, openings (614) have a generally elongate ovular or elliptical shape. Furthermore, openings (614) are likewise configured to locally increase the flexibility of inner sheath (612) in the region of inner sheath (612) where openings (614) are positioned. However, in contrast to openings (622), openings (614) are smaller in scale proportionally to the smaller diameter of inner sheath (612). Although smaller in scale, openings (614) are positioned to align with openings (622) of outer sheath (620). Although the present example is shown as including five sets of openings (614, 622), it should be understood that in other examples any suitable number of openings (614, 622) may be used. Openings (614) are configured to allow inner sheath (612) to bend along a single plane, with openings (614) on one side of inner sheath (612) expanding while openings (614) on the other side of inner sheath (612) contracting as inner sheath (612) bends along the plane. In the present example, inner sheath (612) is fixedly secured about articulation section (130) such that inner sheath (612) does not rotate about articulation section (130). However, outer sheath (620) is rotatable about inner sheath (612) and thus about articulation section (130).

FIGS. 20 and 22 show an exemplary use of sheath assembly (610). Initially, sheath assembly (610) may be in a first configuration as shown in FIG. 20. As can be seen, when sheath assembly (610) is in the first configuration, inner and outer sheaths (612, 620) are angularly aligned such that openings (614) of inner sheath (612) are aligned with openings (622) of outer sheath (620). When openings (614, 622) are aligned, the respective bending planes of inner and outer sheaths (612, 620) are aligned such that inner and outer sheaths (612, 620) are together bendable along their common bending plane. Thus, in the first position sheath assembly (610) permits articulation of articulation section (130) when incorporated into shaft assembly (30) described above.

If an operator desires to make sheath assembly (610) rigid, such as when sheath assembly (610) is incorporated into shaft assembly (30) described above, the operator may rotate outer sheath (620) relative to inner sheath (612) 90° about the longitudinal axis of sheath assembly (610) to a second angular position shown in FIG. 22. As can be seen, in the second position, outer sheath (620) has been rotated approximately 90° such that openings (622) of outer sheath (620) are angularly offset from openings (614) of outer sheath (612). When openings (614, 622) are angularly offset by 90°, any flexibility achieved by use of openings (614, 622) is lost because solid portions of sheath (612) block flexibility of openings (622) and solid portions of sheath (620) block flexibility of openings (614). Therefore, when outer sheath (620) is in the second angular position, sheath assembly (610) is used to lock and/or increase the rigidity of articulation section (130).

Although the second position is shown in FIG. 22 as outer sheath (620) being rotated approximately 90° from the position of outer sheath (620) in the first position, it should be understood that outer sheath (620) may be rotated to other positions to achieve the same outcome of stiffening sheath assembly (610). For instance, in some examples outer sheath (620) may be rotated as little as 15° before causing stiffening of sheath assembly (610). Of course, in other examples outer sheath (620) may be rotated even further than 90°. Additionally, although outer sheath (620) is described herein as being rotated, in other examples inner sheath (612) may be rotated instead, or both sheaths (612, 620) may be rotated simultaneously at different rates to achieve the same result. In still other examples, sheaths (612, 620) may not be rotated at all. Instead, one sheaths (612, 620) may be translated longitudinally relative to the other sheaths (612, 620) in order to position openings (622) of outer sheath (620) at longitudinal positions that are offset from the longitudinal positions of openings (614) of outer sheath (612), such that sheaths (612, 620) are out of phase with each other.

Although sheath assembly (610) of the present example is described herein as being manually actuated by an operator, it should be understood that in other examples sheath assembly (610) may be actuated by other means. For instance, in some examples sheath assembly (610) may further comprise certain actuation components that are in communication with articulation bands (140, 142). In examples incorporating such actuation components, the actuation components are responsive to movement of articulation bands (140, 142) such that outer sheath (620) is automatically transitioned between the first and second angular positions by movement of articulation bands (140, 142) through certain predetermined positions. Additionally or in the alternative, sheath assembly (610) may also be spring loaded to automatically transition outer sheath (620) from the first position to the second position. As yet another merely illustrative alternative, sheath assembly (610) may be actuated by knob (120), some other user input feature at articulation control assembly (100), and/or some other feature of handle assembly (20). Still other suitable mechanisms for transitioning outer sheath (620) between the first and second angular positions will be apparent to those of ordinary skill in the art in view of the teachings herein.

E. Articulation Section with Interlocking Coil Sheath

Figure 23:
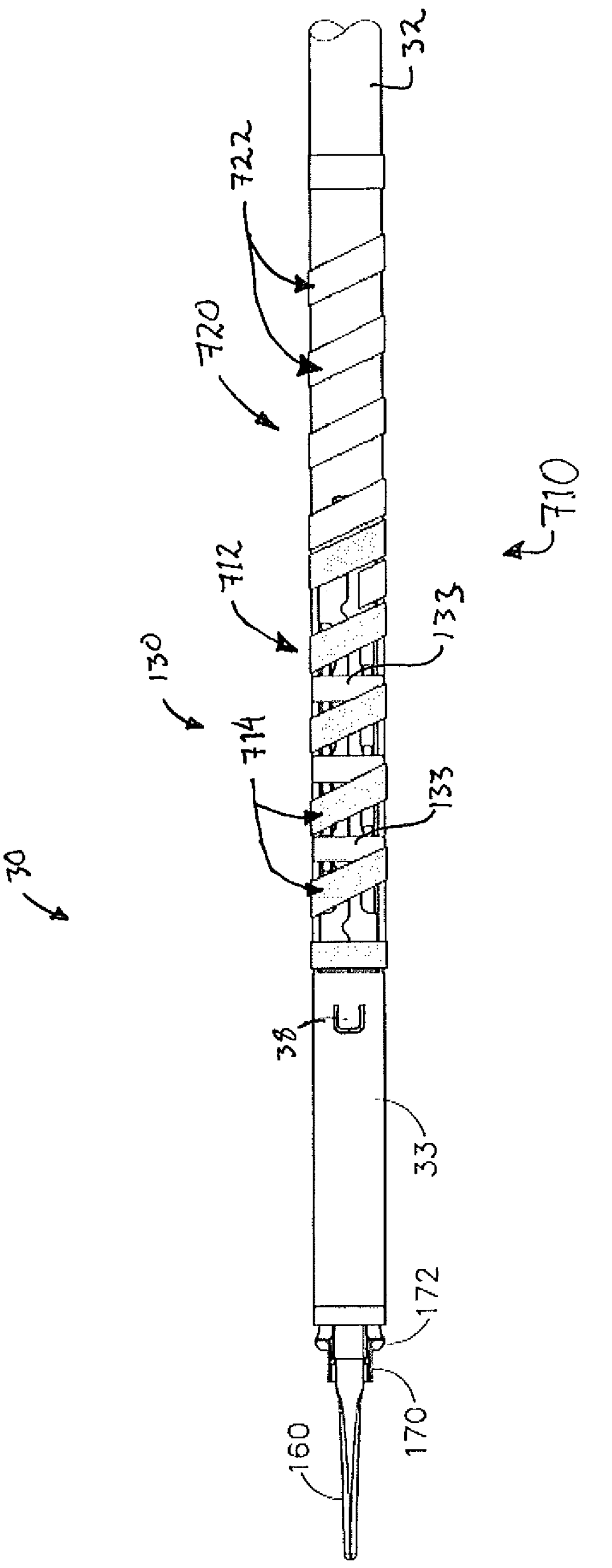
FIG. 23 depicts a top plan view of the shaft assembly and end effector of FIG. 2, including a coil sheath assembly, with the coil sheath assembly in a first position.
Figure 24:
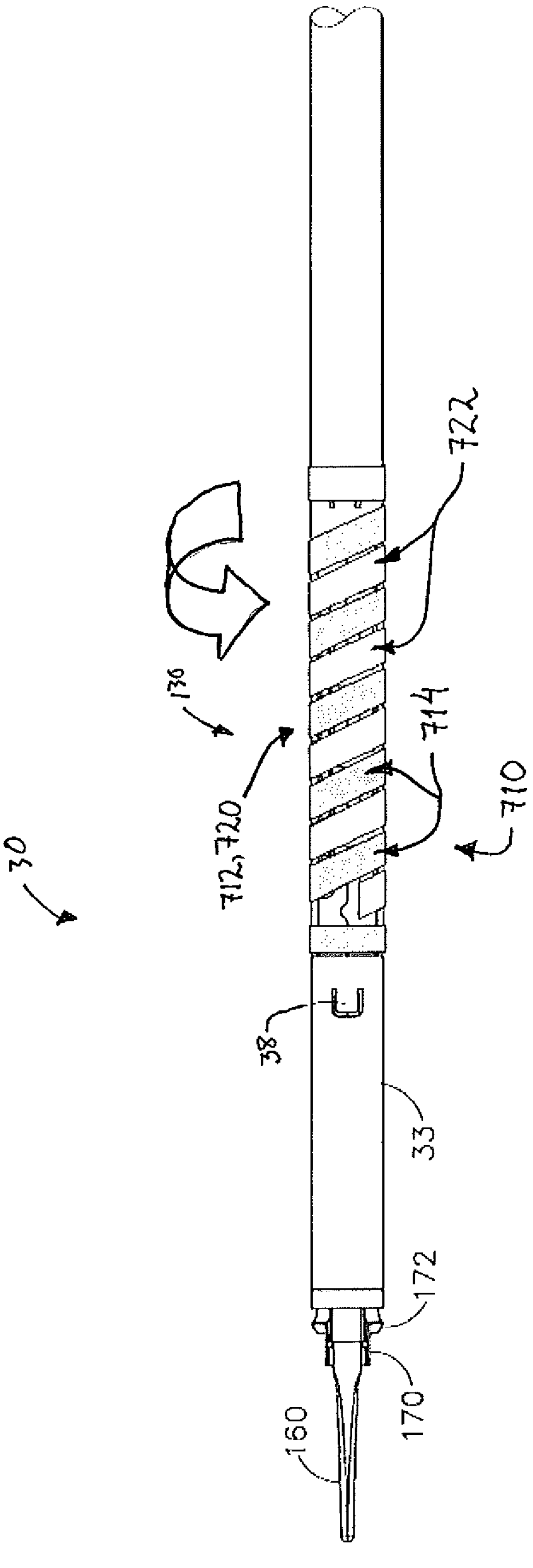
FIG. 24 depicts another top plan view of the shaft assembly and end effector of FIG. 2, with the coil sheath assembly in a second position.

FIGS. 23 and 24 show a version of shaft assembly (30) that is modified to include a sheath assembly (710), which is generally configured to selectively rigidize articulation section (130). In the present example, at least a portion of sheath assembly (710) is disposed around articulation section (130) to thereby permit sheath assembly (710) to selectively rigidize articulation section (130). Sheath assembly (710) comprises a first coil member (712) with a second coil member (720) interlockingly engaged with first coil member (712). As will be described in greater detail below, coil members (712, 720) are configured to cooperatively rigidize articulation section (130).

As can be seen in FIG. 23 first coil member (712) comprises a first helical band (714) that is wrapped around the exterior of articulation section (130). First helical band (714) has a constant helix angle and a constant diameter along the length of articulation section (130). While first helical band (714) is fixedly secured about articulation section (130), first helical band (714) is configured to flex with articulation section (130) as articulation section (130) articulates. When articulation section (130) articulates, first helical band (714) flexes such that the helix contracts on one side of the helix axis while the helix expands on the other side of the helix axis.

Second coil member (720) is configured substantially similarly to comprises first coil member (712). For instance, second coil member (720) comprises a second helical band (722) that is wrapped around the exterior of at least a portion of articulation section (130) and at least a portion of proximal outer shaft (32). Second helical band (722) has a constant helix angle and a constant diameter along a length corresponding to the length of articulation section (130). The helix angle and diameter of second helical band (722) is the same as the helix angle and diameter of first helical band (714). Moreover, the longitudinal thickness of second helical band (722) is approximately the same as the longitudinal spacing between helix segments of first helical band (714). Likewise, the longitudinal thickness of first helical band (714) is approximately the same as the longitudinal spacing between helix segments of second helical band (722). It should therefore be understood that the complementary configuration of helical bands (714, 722) permits second helical band (722) to nest with first helical band (714). In particular, Therefore, coil members (712, 720) are configured such that one coil member (712, 720) is rotatable relative to the other coil member (712, 720) to interlock coils (714, 722) to thereby form a generally tubular structure.

Coil members (712, 720) comprise a material that is generally rigid when coil members (712, 720) are interlocked; but is generally bendable when coil members (712, 720) are separate. By way of example only, suitable materials may include stainless steel, aluminum, or certain polymers such as PTFE, polyethylene terephthalate (PET), high-density polyethylene (HDPE), etc. Of course, any other suitable material(s) may be used as will be apparent to those of ordinary skill in the art in view of the teachings herein.

FIGS. 23 and 24 show an exemplary use of sheath assembly (710). Initially, sheath assembly (710) may be in a first configuration as shown in FIG. 23. As can be seen, when sheath assembly (710) is in the first configuration, coil members (712, 720) are longitudinally positioned such that there is little to no interlocking between each coil member (712, 720). When coil members (712, 720) are in this arrangement, coil members (712, 720) permit free articulation of articulation section (130). First coil member (712) will flex with articulation section (130) as articulation section (130) articulates. Second coil member (720) is positioned proximal to articulation section (130) in this state, such that second coil member (720) is unaffected by articulation of articulation section (130); and second coil member (720) does not impede articulation of articulation section (130).

If an operator wishes to rigidize actuation section (130), the operator may transition sheath assembly (710) to a second configuration shown in FIG. 24. To transition sheath assembly (710) to the second configuration, the operator may grasp either second coil member (720) and rotate second coil member (720) to advance second coil member (720) distally into engagement with first coil member (712). As second coil member (720) is rotated, coils (714, 722) become interlocked with each other such that coils (714, 722) are placed in an alternating relationship. As can be seen in FIG. 24, once the second configuration is reached, coil members (712, 720) are fully interlocked such that coils (714, 722) alternatingly combine to form a rigid tubular structure. With the rigid tubular structure formed, the spacing between each coil (714, 722) is eliminated. With the spacing eliminated, the movement of each coil (714, 722) is correspondingly limited such that sheath assembly (710) forms a rigid structure that encompasses articulation section (130). Because articulation section (130) is encompassed by the rigid structure of sheath assembly (710), articulation of articulation section (130) is correspondingly limited. Thus, it should be understood that when sheath assembly (710) is in the second position, articulation section (130) is generally locked and/or rigid.

Although sheath assembly (710) of the present example is described herein as being manually actuated by an operator, it should be understood that in other examples sheath assembly (710) may be actuated by other means. For instance, in some examples sheath assembly (710) may further comprise certain actuation components that are in communication with articulation bands (140, 142). In examples incorporating such actuation components, the actuation components are responsive to movement of articulation bands (140, 142) second coil member (720) is automatically transitioned between the first and second configurations by movement of articulation bands (140, 142) through certain predetermined positions. Additionally or in the alternative, sheath assembly (710) may also be spring loaded to automatically transition second coil member (720) from the first configuration to the second configuration. As yet another merely illustrative alternative, sheath assembly (710) may be actuated by knob (120), some other user input feature at articulation control assembly (100), and/or some other feature of handle assembly (20). Still other suitable mechanisms for actuating sheath assembly (710) will be apparent to those of ordinary skill in the art in view of the teachings herein.

F. Exemplary Alternative Articulation Section with Rigidizing Linkage

Figure 25:
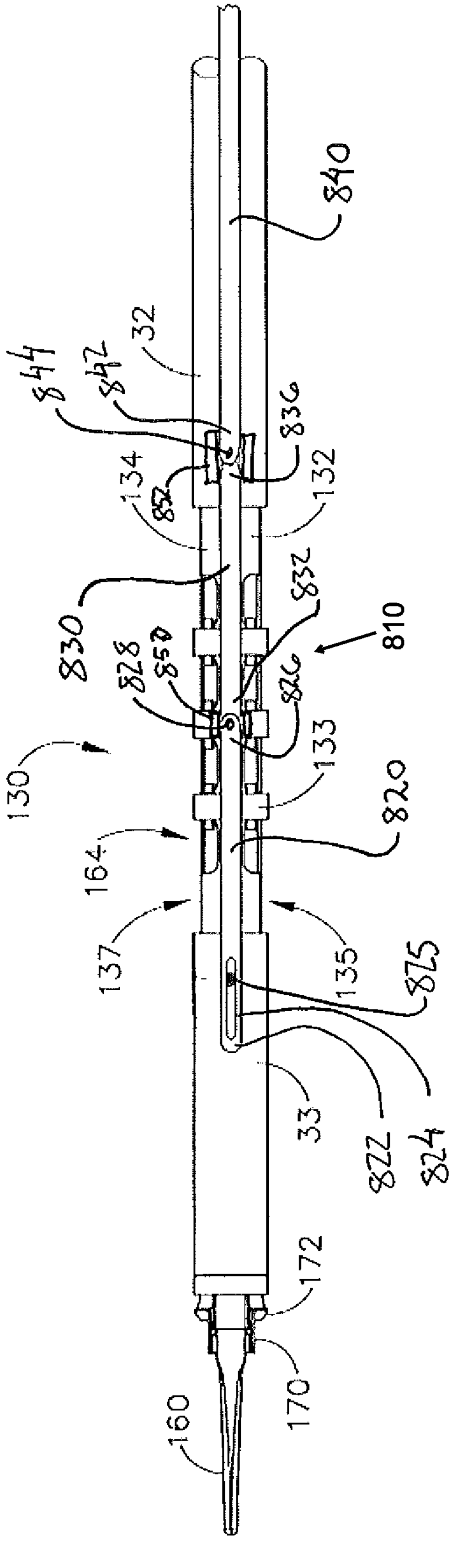
FIG. 25 depicts a top plan view of the shaft assembly and end effector of FIG. 2, including a linkage assembly, with the linkage assembly in a first configuration.
Figure 26:
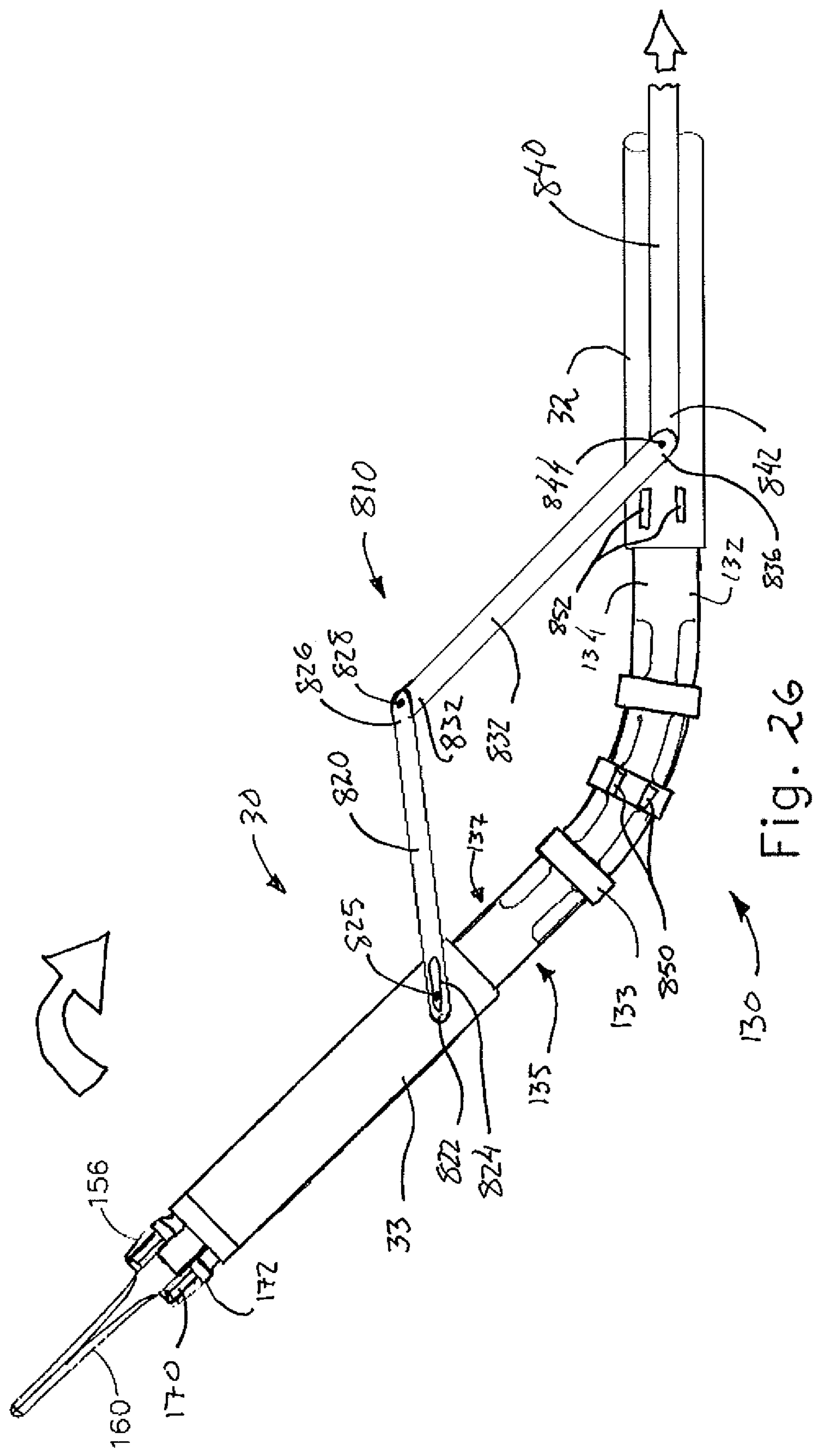
FIG. 26 depicts another top plan view of the shaft assembly and end effector of FIG. 2, with the linkage assembly in a second configuration.

FIGS. 25 and 26 show a modified version of shaft assembly (30) having a linkage assembly (810) incorporated therein. Linkage assembly (810) is generally configured to engage with a portion of articulation section (130) to thereby rigidize articulation section (130). Linkage assembly (810) comprises a first bar (820), a second bar (830), and a third bar (840). As can be seen in FIG. 25 first bar (820) has a distal end (822) and a proximal end (826). Distal end (822) defines a slot (824) that is configured to slidably receive a pin (825). Pin (825) is fixedly secured to distal outer sheath (33). Pin (825) connects first bar (820) to distal outer sheath (33) such that first bar (820) is operable to slide a predetermined distance and pivot relative to distal outer sheath (33). As will be described in greater detail below, slot (824) permits linkage assembly (810) to slide relative to shaft assembly (30) to lock and unlock articulation section (130). Proximal end (826) of first bar (820) comprises a connector (828), which pivotably connects first bar (820) to second bar (830) as will be described in greater detail below.

Second bar (830) comprises a distal end (832) and proximal end (836). As noted above, second bar (830) is pivotably secured to first bar (820) via connector (828). In particular, connector (828) connects proximal end (826) of first bar (820) to distal end (832) of second bar (830) such that second bar (830) is operable to pivot relative to first bar (820). Proximal end (836) of second bar (830) is pivotably secured to third bar (840), as will be described in greater detail below.

Third bar (840) has a distal end (842) and a proximal end (not shown). Distal end (842) of third bar (840) comprises a connector (844). Connector (844) is configured to pivotably connect proximal end (836) of second bar (830) to distal end of third bar (840). Accordingly second bar (830) is configured to pivot relative to third bar (840). Although not shown, it should be understood that the proximal end of third bar (840) may be connected to an actuator, handle, or other device to provide longitudinal translation of third bar (840) relative to shaft assembly (30). As will be described in greater detail below, such an actuation device permits linkage assembly (810) to be translated longitudinally relative to shaft assembly (30) to selectively rigidize articulation section (130).

Linkage assembly (810) further comprises a first pair of ridges (850) and a second pair of ridges (852). Each set of ridges (850, 852) extends upwardly (i.e., out of the page in the views shown in FIGS. 25-26) and longitudinally. First ridges (850) are fixed to at least one retention collar (133) (e.g., the middle retention collar (133) in the present example) and are configured to rigidly engage proximal end (826) of first bar (820) and distal end (842) of second bar (830). In particular, first ridges (850) receive proximal end (826) of first bar (820) and distal end (842) of second bar (830) in a gap laterally defined between first ridges (850). Second ridges (852) are fixed on at least a portion of proximal outer sheath (32). Second ridges (852) are configured to rigidly engage proximal end (836) of second bar (830) and distal end (842) of third bar (840). In particular, second ridges (852) receive proximal end (836) of second bar (830) and distal end (842) of third bar (840) in a gap laterally defined between second ridges (852). Generally, ridges (850, 852) are configured to selectively maintain linkage assembly (810) in a rigid configuration, as will be described in greater detail below.

FIGS. 25 and 26 show an exemplary use of linkage assembly (810). Initially, linkage assembly (810) is in a first position as shown in FIG. 25. As can be seen, when linkage assembly (810) is in the first position, bars (820, 830, 840) are positioned such that proximal end (826) of first bar (820) and distal end (832) of second bar (830) are positioned in the gap laterally defined between first ridges (850). Additionally, proximal end (836) of second bar (830) and distal end (842) of third bar (840) are positioned in the gap laterally defined between second ridges (852). Because of this positioning, ridges (850, 852) maintain linkage assembly (810) in a rigid position. Additionally, because first ridges (850) are secured to at least one retention collar (133), articulation section (130) is also maintained in a rigid configuration. Therefore, when linkage assembly (810) is in the first position, linkage assembly (810) rigidizes articulation section (130).

If an operator desires to articulate articulation section (130), the operator may transition linkage assembly (810) to a second position shown in FIG. 26. To transition linkage assembly (810) to the second position, an operator may actuate third bar (840) proximally to longitudinally translate linkage assembly (810) proximally. Alternatively, if instrument (10) is so equipped, an operator may actuate articulation control assembly (100) or other device described above that may be connected to the proximal end of third bar (840). Regardless of how linkage assembly (810) is longitudinally translated proximally, it should be understood that such translation will lead to bars (820, 830, 840) becoming disengaged from ridges (850, 852). In particular, as linkage assembly (810) is translated proximally, bars (820, 830, 840) may deflect upwardly (i.e., out of the page in the views shown in FIGS. 25-26) to exit the gaps laterally defined between ridges (850, 852) such that bars (820, 830, 840) become free to move transversely relative to ridges (850, 852). With bars (820, 830, 840) free from ridges (850, 852), bars (820, 830, 840) are now operable to pivot about pin (825) and connectors (828, 844). Thus, linkage assembly (810) is no longer in a rigid state. Because linkage assembly (810) is not in a rigid state and because linkage assembly is no longer engaged with slot (850), linkage assembly (810) no longer rigidizes articulation section (130).

Figure 27:
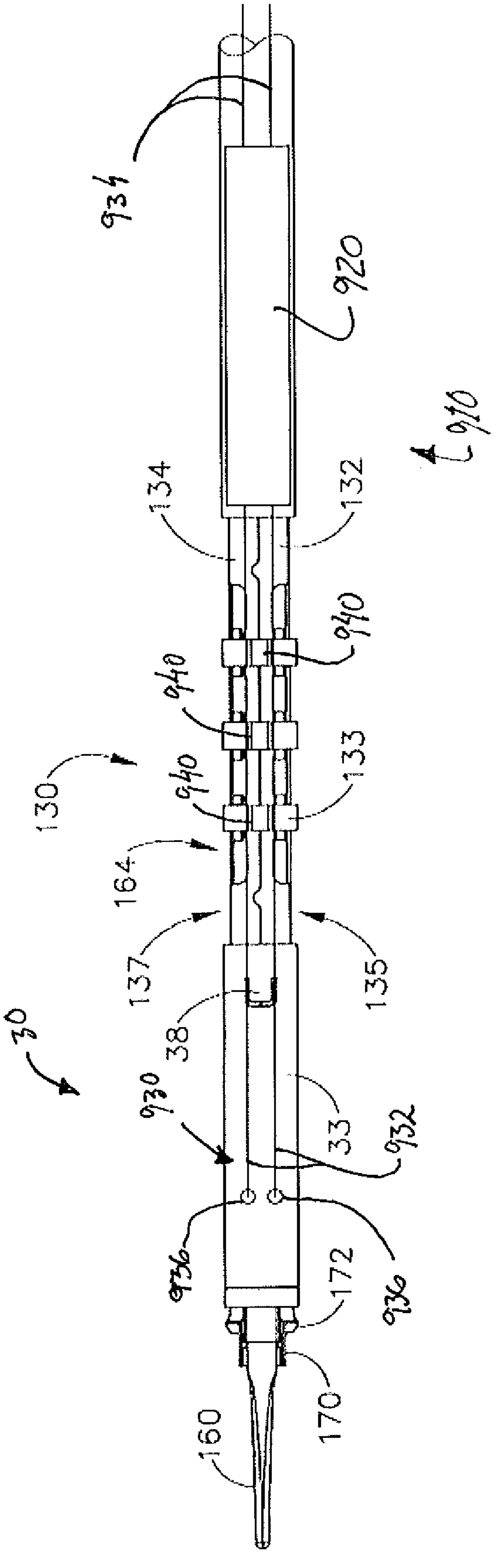
FIG. 27 depicts a top plan view of the shaft assembly and end effector of FIG. 2, including a rigidizing plate assembly, with the rigidizing plate assembly in a proximal position.
Figure 28:
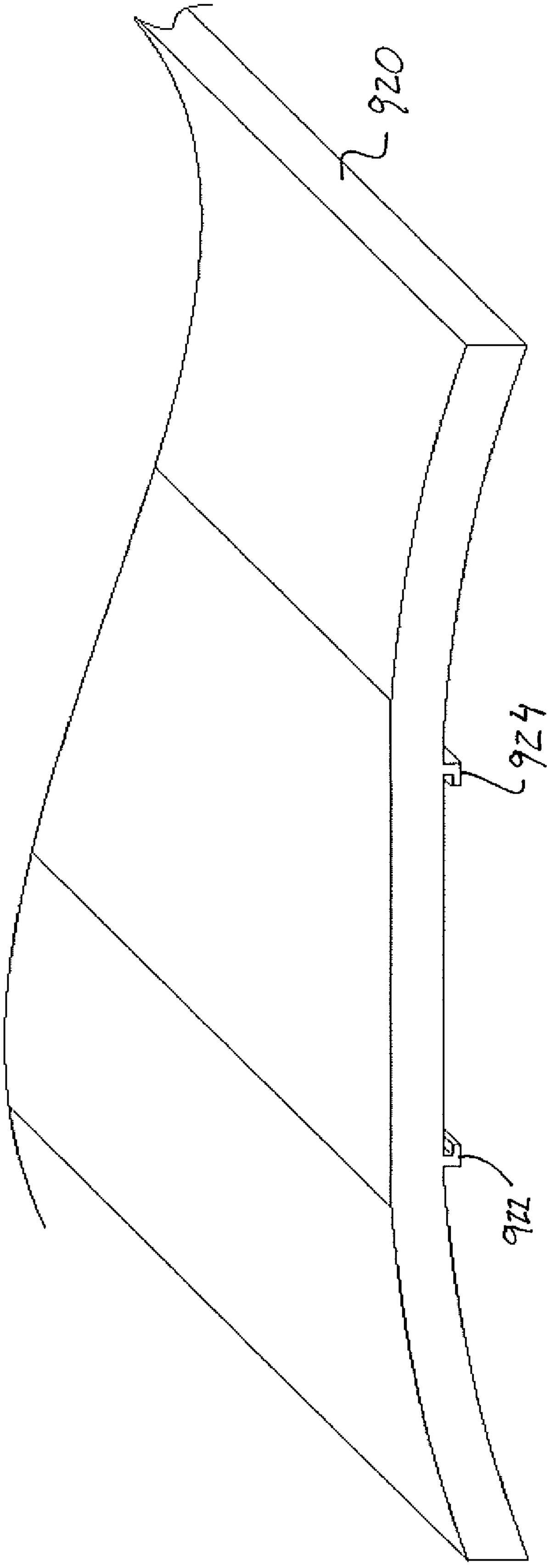
FIG. 28 depicts a perspective view of the rigidizing member of the rigidizing plate assembly of FIG. 27.
Figure 29:
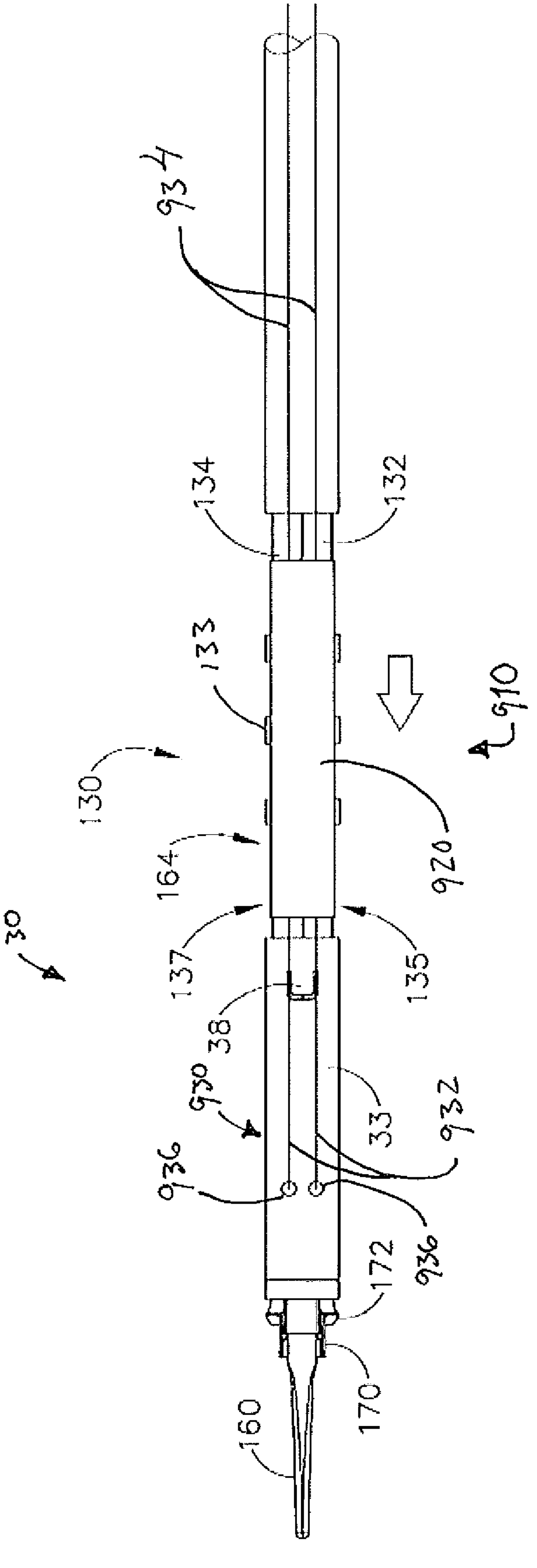
FIG. 29 depicts another top plan view of the shaft assembly and end effector of FIG. 2, with the rigidizing plate assembly is a distal position.

G. Exemplary Alternative Articulation Section with Translatable Rigidizing Member FIGS. 27-29 show a modified version of shaft assembly (30) equipped with a rigidizing plate assembly (910). Plate assembly (910) comprises a rigidizing member (920), an actuation assembly (930), and a pair of plate tracks (940) secured to each retention collar (133) of articulation section (130). Rigidizing member (920) is generally configured to translate longitudinally across the upper portion of proximal outer sheath (32) and articulation section (130) to selectively rigidize articulation section (130). As can be seen in FIG. 28, rigidizing member (920) is has a generally rectangular shape that is contoured to correspond to the outer radius of proximal outer sheath (32). Rigidizing member (920) further comprises two L-shaped engagement members (922, 924). Rigidizing member (920) is formed of a rigid material such as plastic, metal, and/or any other suitable rigid material(s). As will be described in greater detail below, engagement members (922, 924) are generally configured to engage and slide along plate tracks (940) rigidize articulation section (130).

Actuation assembly (930) further comprises a pair of distal wires (932) and a pair of proximal wires (934). Each pair of wires (932, 934) is secured to rigidizing member (920) such that wires (932, 934) are configured to pull rigidizing member (920) distally or proximally. Distal wires (932) extend distally and are received in a pair of openings (936) in distal outer sheath (33). Openings (936) may be connected to a pair of passages extending through shaft assembly (30) to thereby permit distal wires (932) to return to handle assembly (20) described above. Similarly, proximal wires (934) extend proximally down the length of shaft assembly (30) until proximal wires (934) may be received by handle assembly (20). Although not shown, it should be understood that actuation assembly (930) may include features disposed in handle assembly (20) for actuating wires. By way of example only, such features may include a rotatable wheel, which may drive wires (932, 934) to thereby translate rigidizing member (920) proximally or distally. Of course, any other suitable features for driving wires (932, 934) may be incorporated into instrument (10) as will be apparent to those of ordinary skill in the art in view of the teachings herein. Similarly, wires (932, 934) are just one merely illustrative example of how rigidizing member (920) may be driven between a proximal position and a distal position. Other suitable features that may be used to drive rigidizing member (920) between a proximal position and a distal position will be apparent to those of ordinary skill in the art in view of the teachings herein.

Tracks (940) are fixedly secured to each retention collar (133). Tracks (940) are generally shaped to slidably receive the L-shape of engagement members (922, 924). In other words, tracks (940) are configured such that engagement members (922, 924) are permitted to slide longitudinally within tracks (940), while limiting any lateral movement of engagement members (922, 924). Although tracks (940) are described herein as being secured to each retention collar (133), it should be understood that in other examples, tracks (940) may be unitarily formed features of retention collars (133).

An exemplary use of plate assembly (910) can be seen in FIGS. 27 and 29. As can be seen in FIG. 27, plate assembly (910) is initially in a first longitudinal position. In the first position, rigidizing member (920) is disposed proximally of articulation section (130). Because rigidizing member (920) is disposed proximally of articulation section (130), rigidizing member (920) is not acting upon actuation section (130) and articulation section (130) is thus free to articulate. Therefore, when plate assembly (910) is in the first position, articulation section (130) is unlocked and/or otherwise free to articulate via articulation control assembly (100) described above.

If an operator desires to rigidize articulation section (130), the operator may transition plate assembly (910) to a second longitudinal position shown in FIG. 29. In the second position, rigidizing member (920) is in a distal position such that rigidizing member (920) is in engagement with articulation section (130). To transition rigidizing member (920) to the second position, the operator may actuate wires (932, 934) of actuation assembly (930) to pull rigidizing member (920) distally using any of the above described mechanisms. As rigidizing member (920) moves distally, engagement members (922, 924) of rigidizing member (920) will be slidably received by tracks (930) until rigidizing member (920) is disposed at the distal position. In the distal position, engagement members (922, 924) of rigidizing member (920) remain disposed within tracks (940). Because engagement members (922, 924) are integral to rigidizing member (920), the rigidity of rigidizing member (920) is imparted onto engagement members (922, 924). Because engagement members (922, 924) engage tracks (940) that are fixedly secured to retention collars (133), the rigidity of rigidizing member (920) is imparted to retention collars (133) and articulation section (130). Therefore, plate assembly (910) rigidizes articulation section (130) when plate assembly (910) is in the second position. If the operator wishes to articulate articulation section (130), the operator may simply retract rigidizing member (920) proximally back to the first position shown in FIG. 27, thereby de-rigidizing articulation section (130) and enabling articulation section (130) to flex in response to actuation of articulation control assembly (100).

H. Exemplary Alternative Instrument with Translatable Outer Sheath

Figure 30:
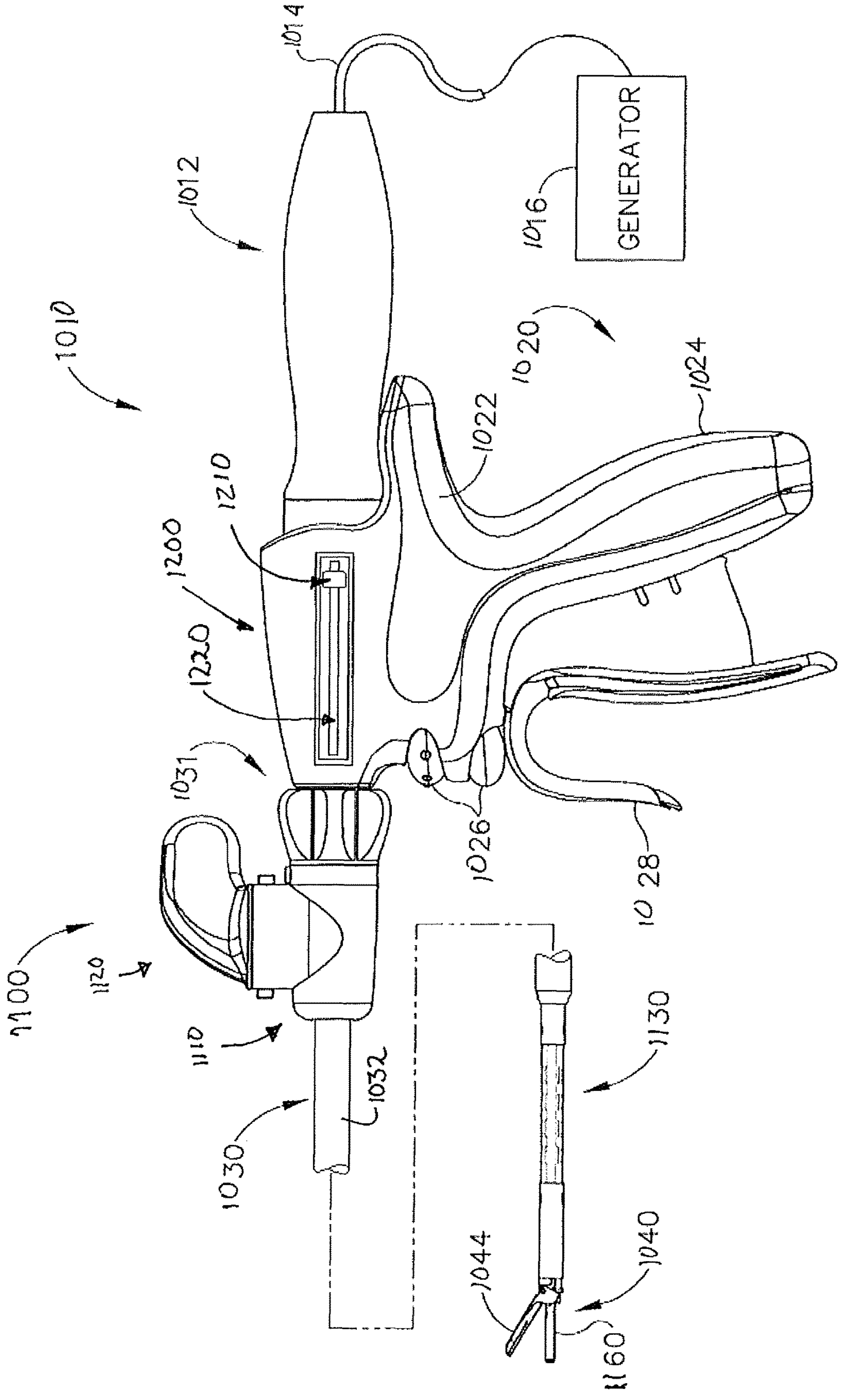
FIG. 30 depicts a side elevational view of an exemplary alternative surgical instrument, with an outer sheath and actuation driver in a proximal position.

FIG. 30 shows an exemplary alternative instrument (1010). Instrument (1010) of the present example is substantially the same as instrument (10) described above, except as otherwise noted herein. For instance, instrument (1010) of the present example comprises a handle assembly (1020), a shaft assembly (1030), and an end effector (1040). Handle assembly (1020) comprises a body (1022) including a pistol grip (1024) and a pair of buttons (1026). Handle assembly (1020) also includes a trigger (1028) that is pivotable toward and away from pistol grip (1024). It should be understood, however, that various other suitable configurations may be used, including but not limited to a scissor grip configuration. End effector (1040) includes an ultrasonic blade (1160) and a pivoting clamp arm (1044). Clamp arm (1044) is coupled with trigger (1028) such that clamp arm (1044) is pivotable toward ultrasonic blade (1160) in response to pivoting of trigger (1028) toward pistol grip (1024); and such that clamp arm (1044) is pivotable away from ultrasonic blade (1160) in response to pivoting of trigger (1028) away from pistol grip (1024). Various suitable ways in which clamp arm (1044) may be coupled with trigger (1028) will be apparent to those of ordinary skill in the art in view of the teachings herein. In some versions, one or more resilient members are used to bias clamp arm (1044) and/or trigger (1028) to the open position shown in FIG. 30.

An ultrasonic transducer assembly (1012) extends proximally from body (1022) of handle assembly (1020). Transducer assembly (1012) is coupled with a generator (1016) via a cable (1014), such that transducer assembly (1012) receives electrical power from generator (1016). Piezoelectric elements in transducer assembly (1012) convert that electrical power into ultrasonic vibrations. Generator (1016) may include a power source and control module that is configured to provide a power profile to transducer assembly (1012) that is particularly suited for the generation of ultrasonic vibrations through transducer assembly (1012).

Blade (1160) of the present example is operable to vibrate at ultrasonic frequencies in order to effectively cut through and seal tissue. Blade (1160) is positioned at the distal end of an acoustic drivetrain. This acoustic drivetrain includes transducer assembly (1012) and an acoustic waveguide (not shown). The acoustic waveguide comprises a flexible portion (not shown) similar to flexible portion (166) described above with respect to instrument (10). Transducer assembly (1012) includes a set of piezoelectric discs (not shown) located proximal to a horn (not shown) of the waveguide. The piezoelectric discs are operable to convert electrical power into ultrasonic vibrations, which are then transmitted along the waveguide to blade (1160) in accordance with known configurations and techniques. By way of example only, this portion of the acoustic drivetrain may be configured in accordance with various teachings of various references that are cited herein.

Shaft assembly (1030) of the present example extends distally from handle assembly (1020). Unless otherwise noted herein, shaft assembly (1030) is substantially the same as shaft assembly (30) described above with respect to instrument (10). For instance, shaft assembly (1030) includes an articulation section (1130), which is located at a distal portion of shaft assembly (1030), with end effector (1040) being located distal to articulation section (1130). As shown in FIG. 30, a knob (1031) is secured to a proximal portion of shaft assembly (1030). Knob (1031) is rotatable relative to body (1022), such that shaft assembly (1030) is rotatable about the longitudinal axis defined by shaft assembly (1030), relative to handle assembly (1020). Such rotation may provide rotation of end effector (1040), articulation section (1130), and shaft assembly (1030) unitarily. Of course, rotatable features may simply be omitted if desired.

Articulation section (1130) is substantially the same as articulation section (130) described above with respect to instrument (10), unless otherwise note herein. For instance, articulation section (1130) is operable to selectively position end effector (1040) at various lateral deflection angles relative to a longitudinal axis defined by shaft assembly (1030). Like with articulation section (130), articulation section (1130) is driven by a pair of articulation bands (not shown) disposed within articulation section (1130) and extending through shaft assembly (1030). When the articulation bands translate longitudinally in an opposing fashion, this will cause articulation section (1130) to bend, thereby laterally deflecting end effector (1040) away from the longitudinal axis of shaft assembly (1030) from a straight configuration to an articulated configuration. In particular, end effector (1040) will be articulated toward the articulation band that is being pulled proximally. During such articulation, the other articulation band may be pulled distally.

Instrument (1100) further includes an articulation control assembly (1100) that is secured to a proximal portion of shaft assembly (1030). Articulation control assembly (1100) comprises a housing (1110) and a rotatable knob (1120). Like with articulation control assembly (100) described above, rotatable knob (1120) is configured to rotate relative to housing (1110) to drive the articulation bands in opposing directions.

Unlike instrument (10) described above, instrument (1010) of the present example further includes a sheath drive assembly (1200). Sheath drive assembly (1200) is generally operable to translate a proximal outer sheath (1032) of shaft assembly (1030) to lock and/or increase the rigidity of articulation section (1130). Sheath drive assembly (1200) comprises an actuation driver (1210) extending through a slot (1220) disposed on the exterior of handle assembly (1020).

Figure 31:
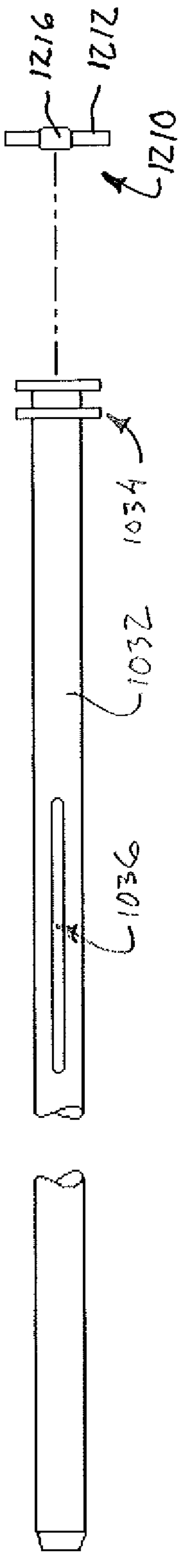
FIG. 31 depicts an exploded side view of the outer sheath and actuation driver of FIG. 30.

FIG. 31 shows an exploded view of outer sheath (1032) and actuation driver (1210). As can be seen, outer sheath (1032) comprises a pair of flanges (1034) and a slot (1036). Flange pair (1034) is disposed at the proximal end of outer sheath (1032) and is configured to receive a corresponding portion of actuation driver (1210), as will be described in greater detail below. Slot (1036) is disposed in outer sheath (1032) proximally of the distal end of outer sheath (1032). Slot (1036) is configured to permit components associated with rotatable knob (1031) to extend through outer sheath (1032) such that outer sheath (1032) and other components of shaft assembly (1030) may be rotated by rotatable knob (1031).

Figure 32:
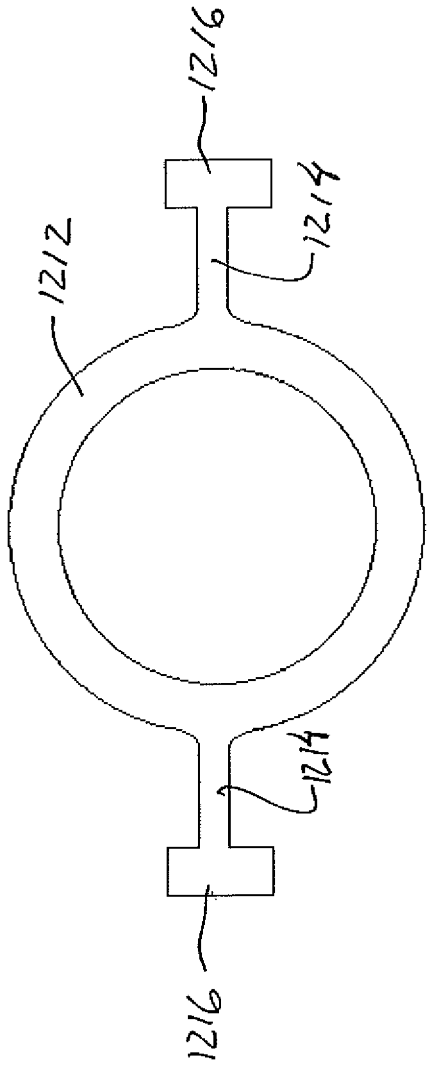
FIG. 32 depicts a front end view of the actuation driver of FIG. 30.

Actuation driver (1210) is shown in FIG. 32. As can be seen, actuation driver (1210) comprises an annular member (1212), two armatures (1214), and two tabs (1216). Annular member (1212) is configured to be rotatably received by flange pair (1034) of outer sheath (1032). When annular member (1212) is disposed between flanges (1034), outer sheath (1032) can freely rotate relative to annular member (1212). This feature may be desirable because free rotation of outer sheath (1032) relative to annular member (1212) may permit outer sheath (1032) to rotate while actuation driver (1210) may remain fixed. This feature may be further desirable because flange pair (1034) may still permit actuation driver (1210) to drive translation of outer sheath (1032) despite rotation of outer sheath (1032).

Armatures (1214) extend outwardly from annular member (1212). Armatures (1214) are configured to extend through corresponding slots (1220) in handle assembly (1020), with each tab (1216) disposed on the exterior of handle assembly (1020). Thus, armatures (1214) connect tabs (1216), which are disposed on the outside of handle assembly (1020), to annular member (1212), which is disposed on the inside of handle assembly (1020).

Figure 33:
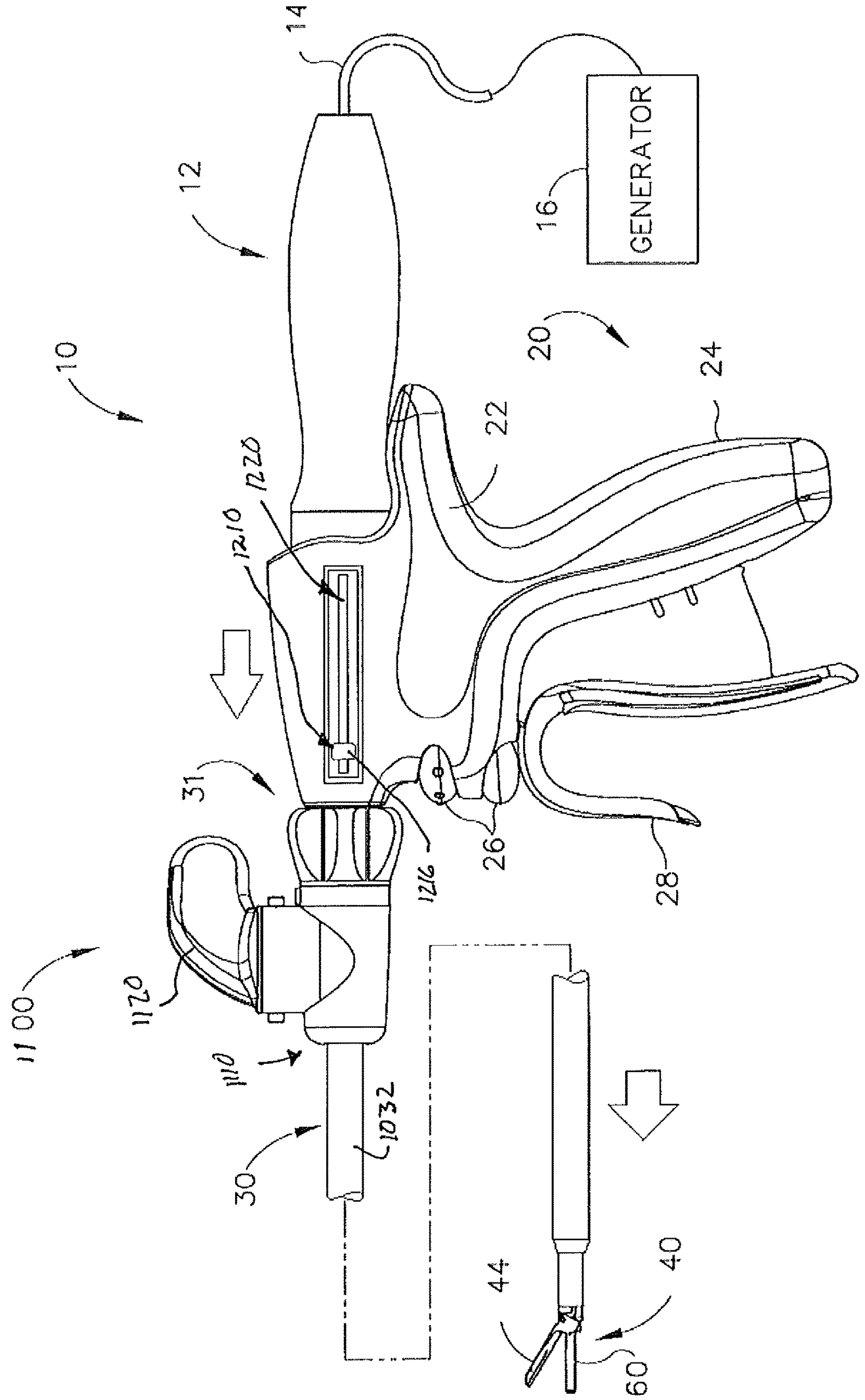
FIG. 33 depicts another side elevational view of the instrument of FIG. 30 with the outer sheath and actuation driver in a distal position.

FIGS. 30 and 33 show an exemplary use of sheath drive assembly (1200). As can be seen in FIG. 30, sheath drive assembly (1200) is initially in a first longitudinal position. In the first position, outer sheath (1032) is disposed in a proximal position such that outer sheath (1032) is proximal of articulation section (1130). Correspondingly, actuation driver (1210) is in a proximal position relative to slot (1220). Thus, in the first position, articulation section (1130) is free to articulate via articulation control assembly (1100) as described above.

If an operator desires to rigidize articulation section (1130), the operator may actuate sheath drive assembly (1200) to a second longitudinal position shown in FIG. 33. In the second position, outer sheath (1032) is driven distally over articulation section (1130). To drive outer sheath (1032) distally to the distal position shown in FIG. 33, the operator may apply a force distally to tab (1216) of actuation driver (1210) thereby driving actuation driver (1210) distally. Actuation driver (1210) will then act on flange (1034) of outer sheath (1032) via annular member (1212) to drive outer sheath (1032) distally. Once outer sheath (1032) is disposed over articulation section (1130), the rigidity of outer sheath (1032) will rigidize articulation section (1130). Therefore, it should be understood that when sheath drive assembly (1200) is in the second position, articulation section (1130) is rigidized.

In some versions, one or more features in communication with actuation driver (1210) will also lock out rotatable knob (1120) such that knob (1120) cannot be rotated when actuation driver (1210) is in the distal position. In addition or in the alternative, one or more features in communication with knob (1120) may lock out actuation driver (1210) such that actuation driver (1210) cannot be slid from the proximal position to the distal position unless knob (1120) is at the neutral rotational position that is associated with articulation section (1130) being in a straight, non-articulated configuration. Various suitable ways in which such lockout features may be configured will be apparent to those of ordinary skill in the art in view of the teachings herein.

As yet another merely illustrative example, one or more features in communication with actuation driver (1210) may be configured to automatically de-articulate an otherwise articulated articulation section (1130) in response to distal movement of actuation driver (1210) from the proximal position toward the distal position. Various suitable ways in which such features may be configured will be apparent to those of ordinary skill in the art in view of the teachings herein.

I. Exemplary Alternative Instrument with Translatable Rigidizing Members

Figure 34:
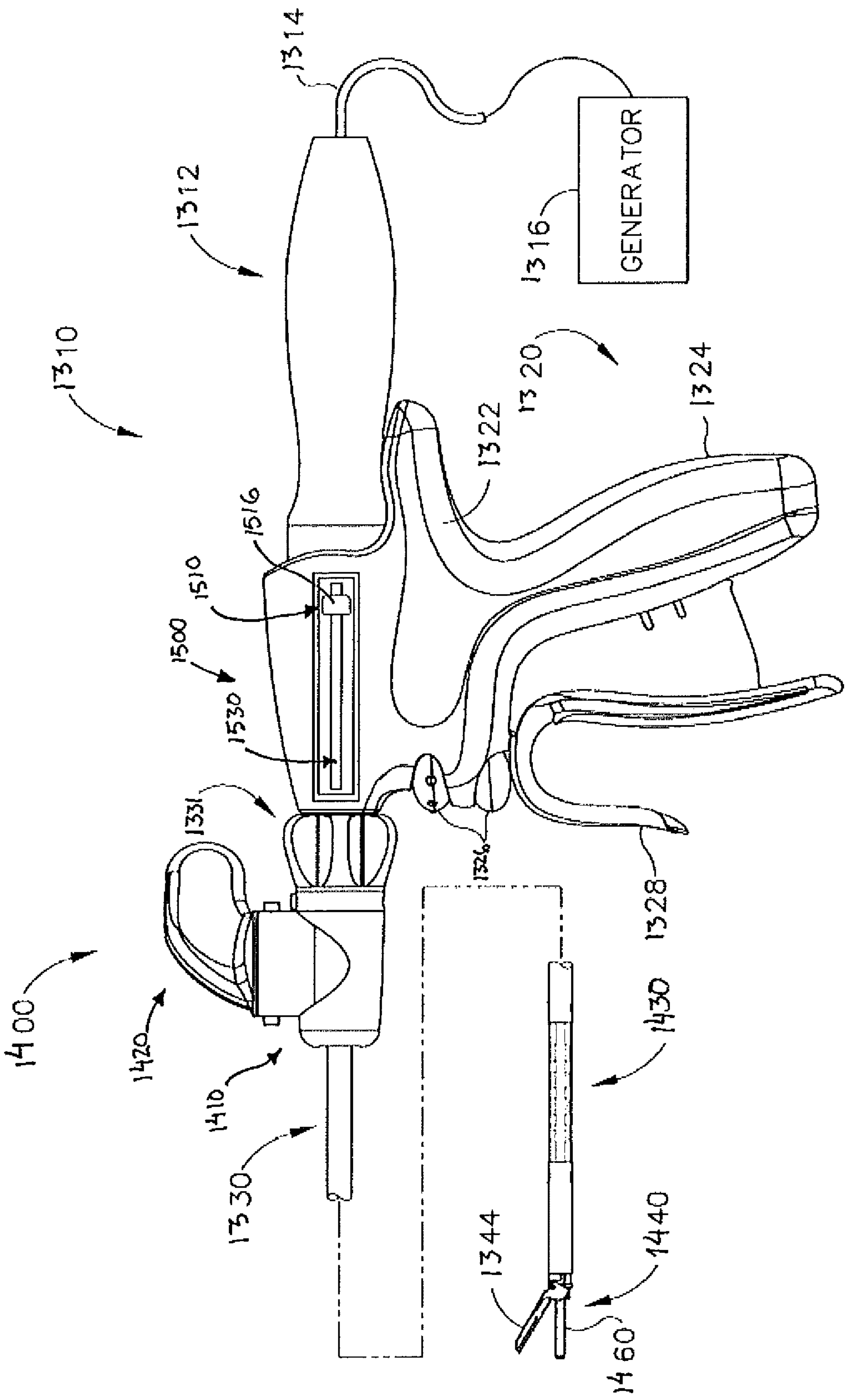
FIG. 34 depicts a side elevational view of another exemplary alternative surgical instrument, with a rigidizing member and a drive member in a proximal position.

FIG. 34 shows an exemplary alternative instrument (1310). Instrument (1310) of the present example is substantially the same as instrument (10) described above, except as otherwise noted herein. For instance, instrument (1310) of the present example comprises a handle assembly (1320), a shaft assembly (1330), and an end effector (1340). Handle assembly (1320) comprises a body (1322) including a pistol grip (1324) and a pair of buttons (1326). Handle assembly (1320) also includes a trigger (1328) that is pivotable toward and away from pistol grip (1324). It should be understood, however, that various other suitable configurations may be used, including but not limited to a scissor grip configuration. End effector (1340) includes an ultrasonic blade (1460) and a pivoting clamp arm (1344). Clamp arm (1344) is coupled with trigger (1328) such that clamp arm (1344) is pivotable toward ultrasonic blade (1460) in response to pivoting of trigger (1328) toward pistol grip (1324); and such that clamp arm (1344) is pivotable away from ultrasonic blade (1460) in response to pivoting of trigger (1328) away from pistol grip (1324). Various suitable ways in which clamp arm (1344) may be coupled with trigger (1328) will be apparent to those of ordinary skill in the art in view of the teachings herein. In some versions, one or more resilient members are used to bias clamp arm (1344) and/or trigger (1328) to the open position shown in FIG. 34.

An ultrasonic transducer assembly (1312) extends proximally from body (1322) of handle assembly (1320). Transducer assembly (1312) is coupled with a generator (1316) via a cable (1314), such that transducer assembly (1312) receives electrical power from generator (1316). Piezoelectric elements in transducer assembly (1312) convert that electrical power into ultrasonic vibrations. Generator (1316) may include a power source and control module that is configured to provide a power profile to transducer assembly (1312) that is particularly suited for the generation of ultrasonic vibrations through transducer assembly (1312).

Figure 37:
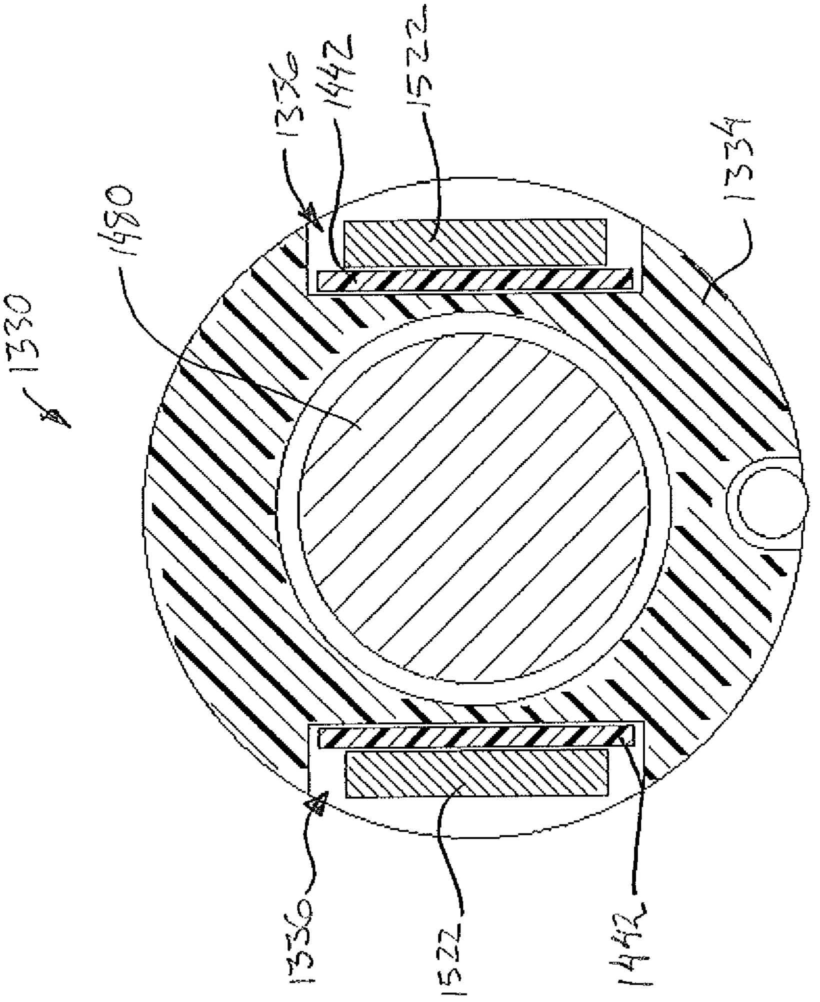
FIG. 37 depicts a front cross-sectional view of a shaft assembly of the instrument of FIG. 34.

Blade (1460) of the present example is operable to vibrate at ultrasonic frequencies in order to effectively cut through and seal tissue. Blade (1460) is positioned at the distal end of an acoustic drivetrain. This acoustic drivetrain includes transducer assembly (1312) and an acoustic waveguide (1480) (as can be seen in FIG. 37). The acoustic waveguide (1480) comprises a flexible portion (not shown) similar to flexible portion (166) described above with respect to instrument (10). Transducer assembly (1312) includes a set of piezoelectric discs (not shown) located proximal to a horn (not shown) of waveguide (1480). The piezoelectric discs are operable to convert electrical power into ultrasonic vibrations, which are then transmitted along waveguide (1480) to blade (1460) in accordance with known configurations and techniques. By way of example only, this portion of the acoustic drivetrain may be configured in accordance with various teachings of various references that are cited herein.

Shaft assembly (1330) of the present example extends distally from handle assembly (1320). Unless otherwise noted herein, shaft assembly (1330) is substantially the same as shaft assembly (30) described above with respect to instrument (10). For instance, shaft assembly (1330) includes an articulation section (1430), which is located at a distal portion of shaft assembly (1330), with end effector (1340) being located distal to articulation section (1430). As shown in FIG. 34, a knob (1331) is secured to a proximal portion of shaft assembly (1330). Knob (1331) is rotatable relative to body (1322), such that shaft assembly (1330) is rotatable about the longitudinal axis defined by shaft assembly (1330), relative to handle assembly (1320). Such rotation may provide rotation of end effector (1340), articulation section (1430), and shaft assembly (1330) unitarily. Of course, rotatable features may simply be omitted if desired.

Articulation section (1430) is substantially the same as articulation section (130) described above with respect to instrument (10), unless otherwise note herein. For instance, articulation section (1430) is operable to selectively position end effector (1340) at various lateral deflection angles relative to a longitudinal axis defined by shaft assembly (1430). Like with articulation section (130), articulation section (1430) is driven by a pair of articulation bands (1440, 1442) (as shown in FIG. 37) disposed within articulation section (1430) and extending through shaft assembly (1330). When articulation bands (1440, 1442) translate longitudinally in an opposing fashion, this will cause articulation section (1430) to bend, thereby laterally deflecting end effector (1340) away from the longitudinal axis of shaft assembly (1330) from a straight configuration to an articulated configuration. In particular, end effector (1340) will be articulated toward the articulation band (1440, 1442) that is being pulled proximally. During such articulation, the other articulation band (1440, 1442) may be pulled distally Instrument (1400) further includes an articulation control assembly (1400) that is secured to a proximal portion of shaft assembly (1330). Articulation control assembly (1400) comprises a housing (1410) and a rotatable knob (1420). Like with articulation control assembly (100) described above, rotatable knob (1420) is configured to rotate relative to housing (1410) to drive articulation bands (1440, 1442) in opposing directions. For instance, rotation of knob (1420) in a first direction causes distal longitudinal translation of articulation band (1440), and proximal longitudinal translation of articulation band (1442); and rotation of knob (1420) in a second direction causes proximal longitudinal translation of articulation band (1440), and distal longitudinal translation of articulation band (1442). Thus, it should be understood that rotation of rotation knob (1420) causes articulation of articulation section (1430).

Unlike instrument (10) described above, instrument (1310) of the present example further includes a rigidizing member drive assembly (1500). Drive assembly (1500) is generally operable to advance a rigidizing member (1520) within shaft assembly (1330) selectively rigidize articulation section (1430). Drive assembly (1500) comprises drive member (1510) and a rigidizing member (1520). Drive member (1510) extends through a slot (1530) in handle assembly (1320) and is rotatably attachable to rigidizing member (1520) to drive rigidizing member (1520) while permitting rotation of rigidizing member (1520) with shaft assembly (1330).

Figure 35:
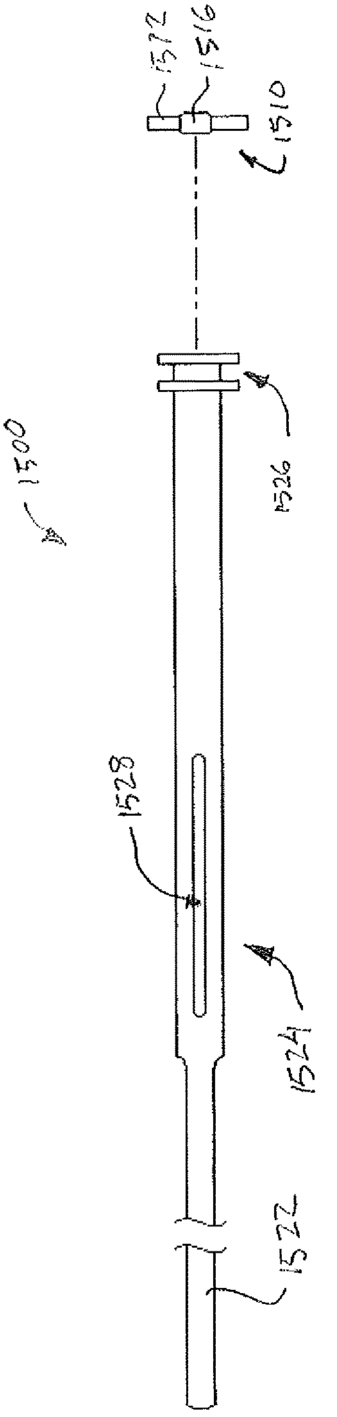
FIG. 35 depicts a side exploded view of the rigidizing member and drive member of FIG. 34.

As can be seen in FIG. 35, rigidizing member (1520) comprises two longitudinally extending posts (1522) and a generally tubular body (1524). As will be described in greater detail below, posts (1522) extend through shaft assembly (1330) and engage with articulation section (1430) to selectively ridigize articulation section (1430). Body (1524) comprises a flange pair (1526) and a slot (1528). Flange pair (1526) is disposed on the proximal end of body (1524) and is configured to receive drive member (1510), as will be described in greater detail below. Slot (1528) is disposed distally of flange pair (1526). Slot (1528) is configured to receive at least a portion of rotatable knob (1331) such that rotatable knob (1331) may engage with rigidizing member (1520) and various components of shaft assembly (1330) to rotate rigidizing member (1520) along with shaft assembly (1330).

Figure 36:
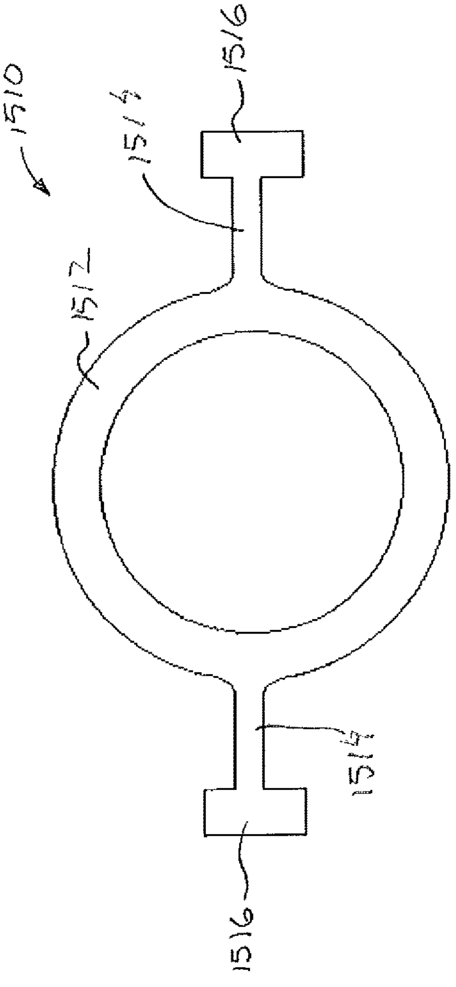
FIG. 36 depicts a front end view of the drive member of FIG. 34.

Drive member (1510) is shown in FIG. 36. As can be seen, drive member (1510) comprises an annular member (1512), two armatures (1514), and two tabs (1516). Annular member (1512) is configured to be rotatably received by flanged portion (1526) of rigidizing member (1520). When annular member (1512) is between flanges (1526), rigidizing member (1520) can freely rotate relative to annular member (1512). This feature may be desirable because free rotation of rigidizing member (1520) relative to annular member (1512) may permit rigidizing member (1520) to rotate while drive member (1510) may remain fixed. This feature may be further desirable because flange pair (1526) may still permit drive member (1510) to drive translation of rigidizing member (1520) despite rotation of rigidizing member (1520).

Armatures (1514) extend outwardly from annular member (1512). Armatures (1514) are configured to extend through corresponding slots (1530) in handle assembly (1320), with each tab (1516) disposed on the exterior of handle assembly (1320). Thus, armatures (1514) connect tabs (1516), which are disposed on the outside of handle assembly (1320), to annular member (1512), which is disposed on the inside of handle assembly (1320).

FIG. 37 shows rigidizing member (1520) disposed within shaft assembly (1330). As can be seen, a body (1334) of shaft assembly (1330) includes channels (1336) that are configured to receive both articulation bands (1440, 1442) and posts (1522) of rigidizing member (1520) adjacent to articulation bands (1440, 1442). Although shaft assembly (1330) of the present example is shown as having a common channels (1336) for both articulation bands (1440, 1442) and posts (1522), it should be understood that in other examples, shaft assembly (1330) includes separate channels for articulation bands (1440, 1442) and posts (1522).

Figure 38:
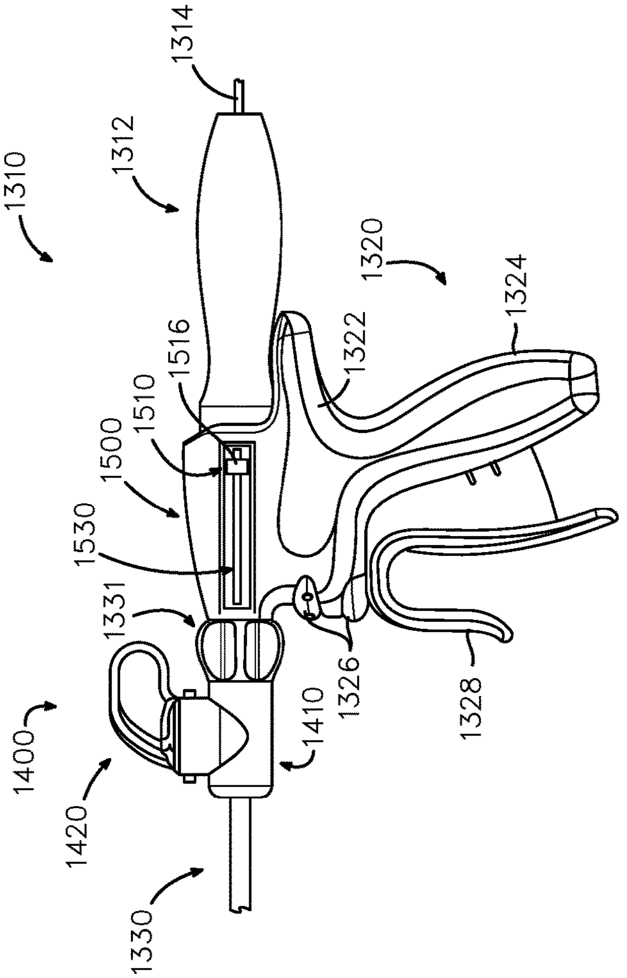
FIG. 38 depicts partial side elevational view of the instrument of FIG. 34, with the drive member in the proximal position.
Figure 39:
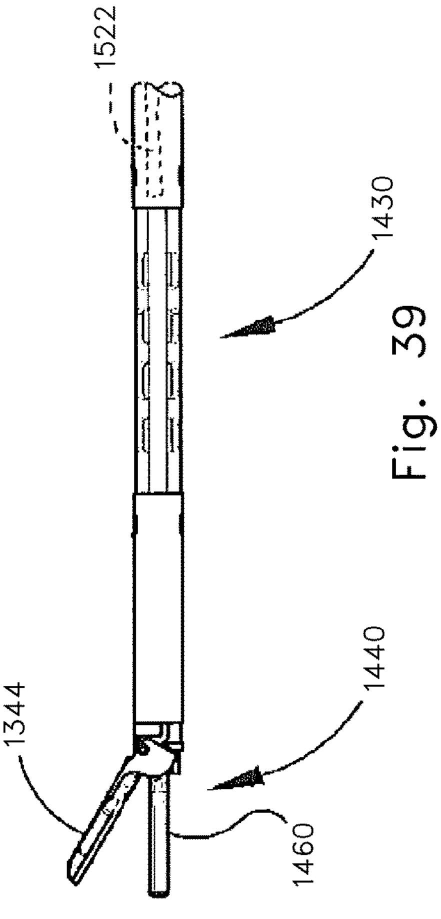
FIG. 39 depicts a detailed side elevational view of a shaft assembly and end effector of the instrument of FIG. 34, with the rigidizing member in the proximal position.

FIGS. 38-43 show an exemplary mode of operation for drive assembly (1500). As can be seen in FIGS. 38 and 39, drive assembly (1500) is initially in a first longitudinal position. In the first position, drive member (1510) is positioned in a proximal position relative to handle assembly (1320) such that rigidizing member (1520) is correspondingly in a proximal position relative to articulation section (1430). As can best be seen in FIG. 39, when rigidizing member (1520) is in the proximal position, posts (1522) of rigidizing member (1520) are disposed proximally of articulation section (1430). With posts (1522) of rigidizing member (1520) disposed proximally of articulation section (1430), articulation section (1430) is free to articulate via articulation control assembly (1400) as described above. Thus, when drive assembly (1500) is in the first position, articulation section (1430) is in an unlocked and/or non-rigid configuration.

Figure 40:
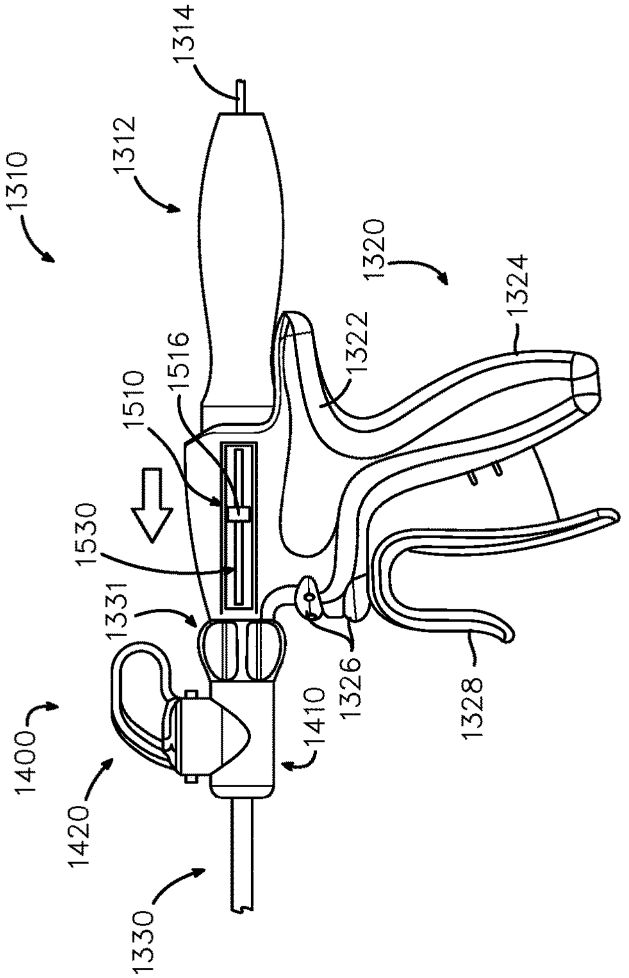
FIG. 40 depicts another partial side elevational view of the instrument of FIG. 34, with the drive member in an intermediate position.
Figure 41:
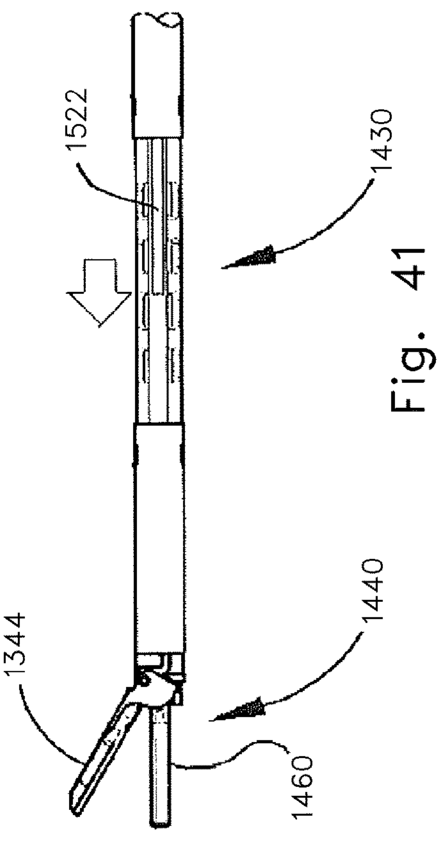
FIG. 41 depicts another detailed side elevational view of the shaft assembly and the end effector of the instrument of FIG. 34, with the rigidizing member in an intermediate position.
Figure 42:
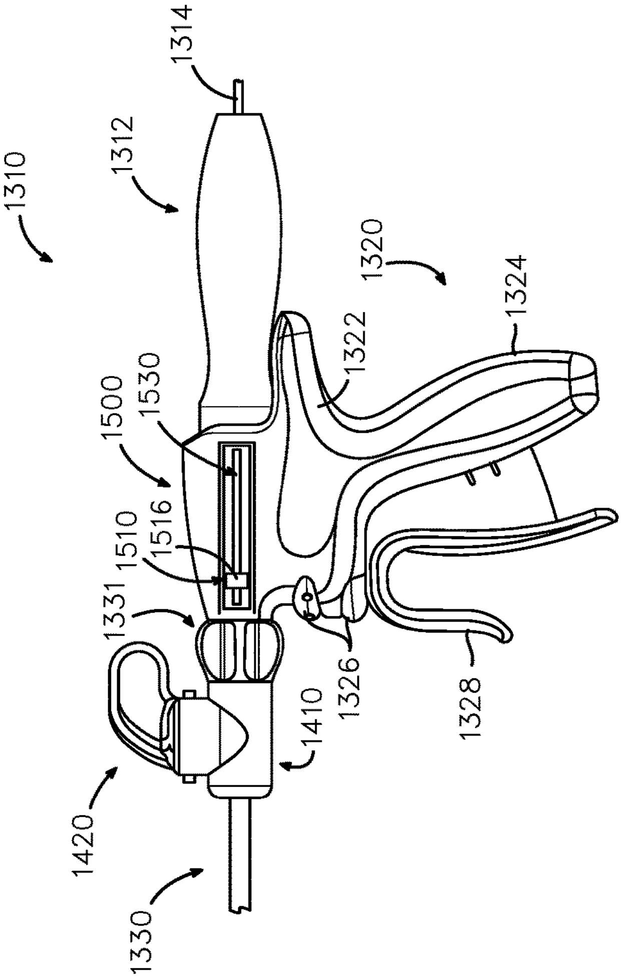
FIG. 42 depicts still another partial side elevational view of the instrument of FIG. 34, with the drive member in a distal position.
Figure 43:
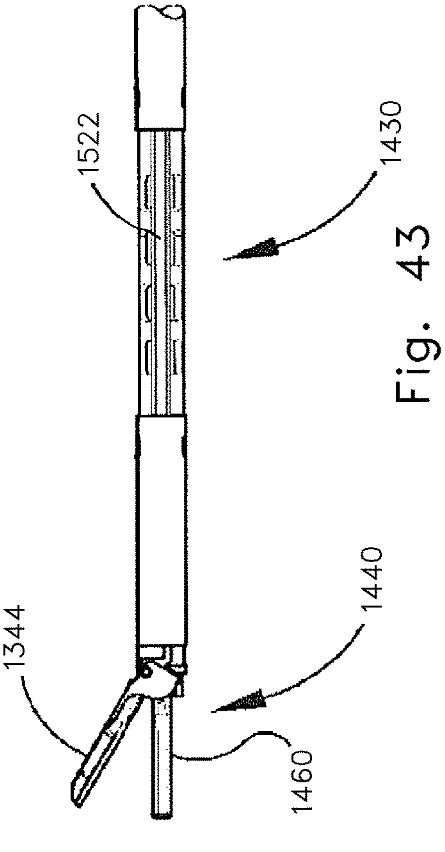
FIG. 43 depicts still another detailed side elevational view of the shaft assembly and the end effector of the instrument of FIG. 34, with the rigidizing member in a distal position.

If an operator desires to rigidize articulation section (1430), the operator may do so by advancing drive assembly (1500) to a second longitudinal position (as shown in FIGS. 42 and 43). To advance drive assembly (1500) to the second position, the operator will advance tabs (1516) of drive member (1510) distally as shown in FIG. 40. Distal advancement of drive member (1510) will cause corresponding advancement of posts (1522) of rigidizing member (1520) within shaft assembly (1330) as shown in FIG. 41. As posts (1522) are advanced distally, posts (1522) begin to engage articulation section (1430). FIGS. 42 and 43 show drive assembly (1500) fully advanced to the second position. As can be seen, in the second position, tabs (1516) of drive member (1510) are advanced to a fully distal position relative to handle assembly (1320). Correspondingly, posts (1522) of rigidizing member (1520) are advanced to a fully distal position. When posts (1522) are in the fully distal position, posts (1522) fully engage articulation section (1430) to rigidize articulation section (1430). In this state, the distal ends of posts (1522) are positioned distal to articulation section (1430), such that posts (1522) span along the full length of articulation section (1430) and are grounded relative to the distal portion of shaft assembly (1330).

Figure 44:
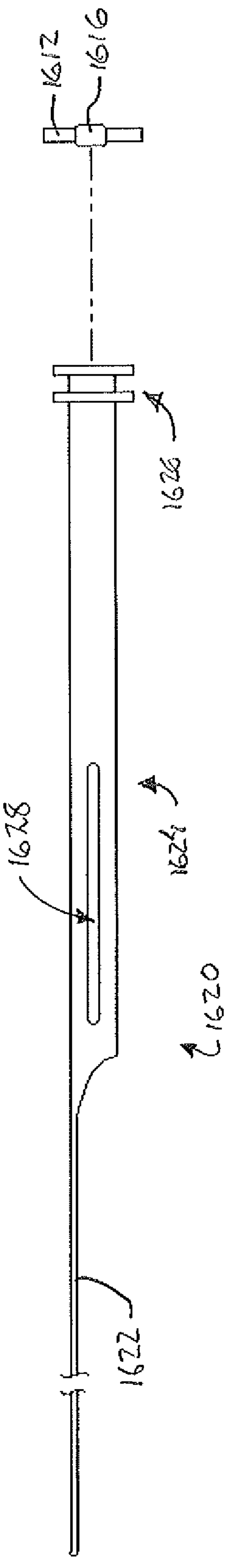
FIG. 44 depicts an exploded view of an exemplary alternative rigidizing member and drive member that may be incorporated into the instrument of FIG. 34.
Figure 45:
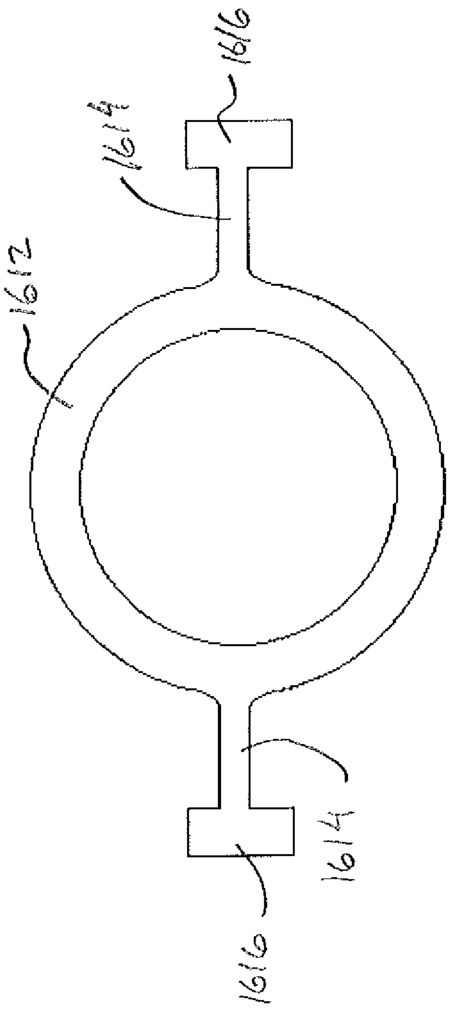
FIG. 45 depicts an front end view of the drive member of FIG. 44.
Figure 46:
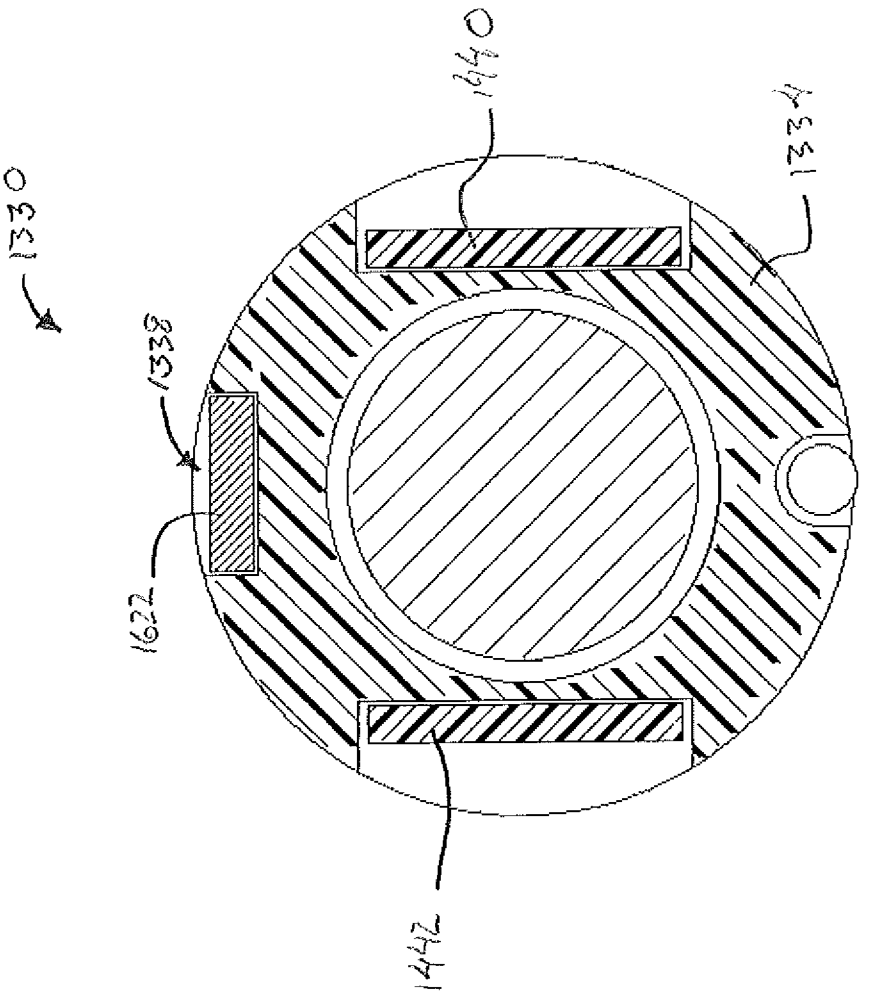
FIG. 46 depicts a cross-sectional view of the shaft assembly of the instrument of FIG. 34 incorporating the rigidizing member of FIG. 44.

In some examples, instrument (1300) described above may include a rigidizing member drive assembly similar to drive assembly (1600) described above having a rigidizing member (1620) with a single post (1622). Such a configuration may be desirable to improve the overall operation of instrument (1300), to improve the ease of use, or to improve the amount of rigidity provided by rigidizing member (1520). For instance, FIGS. 44-46 show an exemplary alternative rigidizing member drive assembly (1600). It should be understood that drive assembly (1600) is substantially the same as drive assembly (1500) described above, unless otherwise noted herein. Drive assembly (1600) of the present example is generally operable to advance a rigidizing member (1620) within shaft assembly (1330) to selectively rigidize articulation section (1430). Drive assembly (1600) comprises drive member (1610) and rigidizing member (1620). Drive member (1610) extends through a slot (1630) in handle assembly (1320) and is rotatably attached to rigidizing member (1620) to drive rigidizing member (1620) while permitting rotation of rigidizing member (1620) with shaft assembly (1330).

As can be seen in FIG. 44, rigidizing member (1620) comprises a single longitudinally extending post (1622) and a generally tubular body (1624). As will be described in greater detail below, post (1622) extends through shaft assembly (1330) and engages with articulation section (1430) to selectively rigidize articulation section (1430). Body (1624) comprises a flange pair (1626) and a slot (1628). Flange pair (1626) is disposed on the proximal end of body (1624) and is configured to receive drive member (1610), as will be described in greater detail below. Slot (1628) is disposed distally of flanged portion (1626). Slot (1628) is configured to receive at least a portion of rotatable knob (1331) such that rotatable knob (1331) may engage with rigidizing member (1620) and various components of shaft assembly (1330) to rotate rigidizing member (1620) along with shaft assembly (1330).

Drive member (1610) is shown in FIG. 45. As can be seen, drive member (1610) comprises a annular member (1612), two armatures (1614), and two tabs (1616). Annular member (1612) is configured to be rotatably received between flanges (1626) of rigidizing member (1620). When annular member (1612) is disposed between flanges (1626), rigidizing member (1620) can freely rotate relative to annular member (1612). This feature may be desirable because free rotation of rigidizing member (1620) relative to annular member (1612) may permit rigidizing member (1620) to rotate while drive member (1610) may remain fixed. This feature may be further desirable because flange pair (1626) may still permit drive member (1610) to drive translation of rigidizing member (1620) despite rotation of rigidizing member (1620).

Armatures (1614) extend outwardly from annular member (1612). Armatures (1614) are configured to extend through slot (1630) in handle assembly (1320) with each tab (1616) disposed on the exterior of handle assembly (1320). Thus, armatures (1614) connect tabs (1616), which are disposed on the outside of handle assembly (1320), to annular member (1612), which is disposed on the inside of handle assembly (1320).

FIG. 46 shows rigidizing member (1620) disposed within shaft assembly (1330). As can be seen, a body (1334) of shaft assembly includes channels (1336) that are configured to receive articulation bands (1440, 1442). Additionally body (1334) includes an additional channel (1338) to receive post (1622) of rigidizing member (1620).

Figure 47:
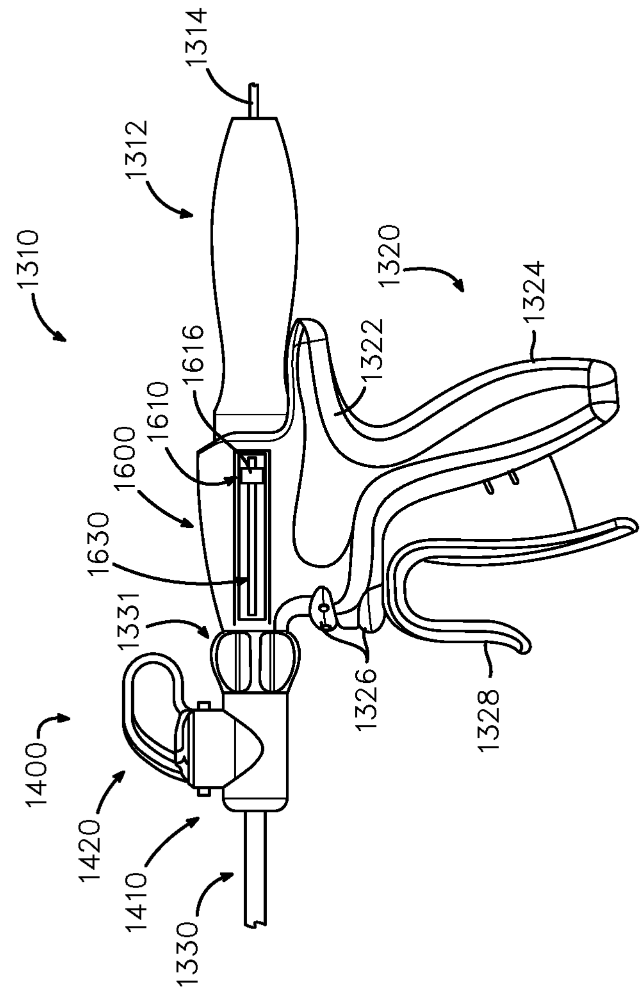
FIG. 47 depicts a partial side elevational view of the instrument of FIG. 34 incorporating the rigidizing member and drive member of FIG. 44, with the drive member in a proximal position.
Figure 48:
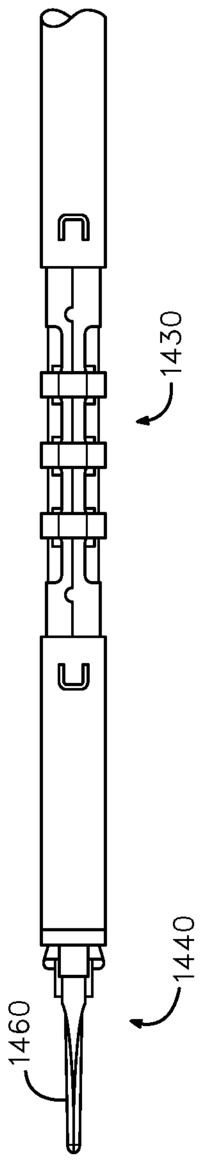
FIG. 48 depicts a detailed top plan view of a shaft assembly and end effector of the instrument of FIG. 34 incorporating the rigidizing member and drive member of FIG. 44, with the rigidizing member in a proximal position.

FIGS. 47-52 show an exemplary mode of operation for drive assembly (1600). As can be seen in FIGS. 47 and 48, drive assembly (1600) is initially in a first longitudinal position. In the first position, drive member (1610) is positioned in a proximal position relative to handle assembly (1320) such that rigidizing member (1620) is correspondingly in a proximal position. As can best be seen in FIG. 48, when rigidizing member (1620) is in the proximal position, post (1622) of rigidizing member (1620) is disposed proximally of articulation section (1430). With post (1622) of rigidizing member (1620) disposed proximally of articulation section (1430), articulation section (1430) is free to articulate via articulation control assembly (1400) as described above. Thus, when drive assembly (1600) is in the first position, articulation section (1430) is in an unlocked and/or non-rigid configuration.

Figure 49:
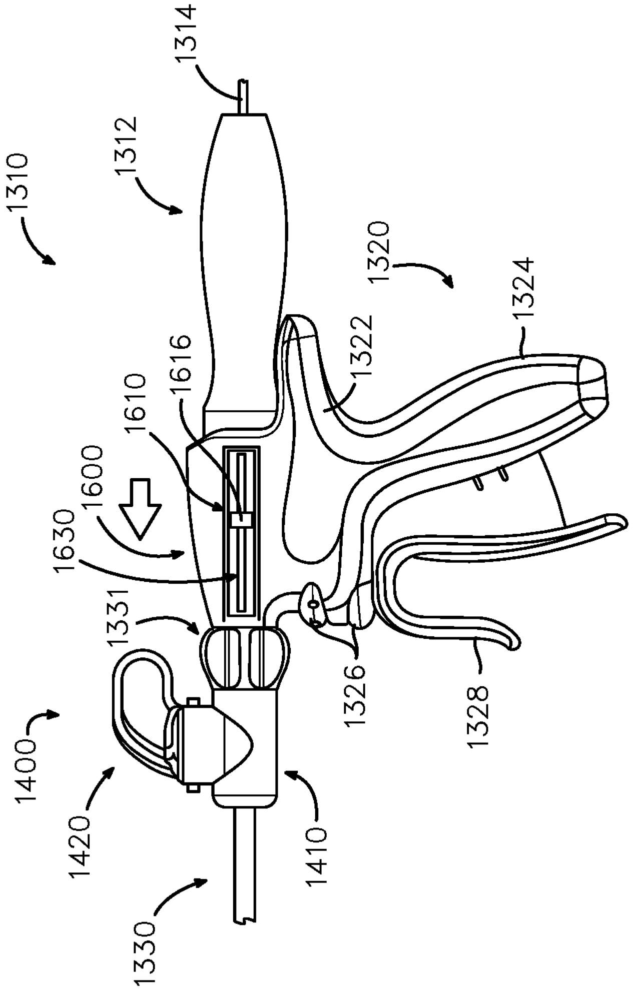
FIG. 49 depicts another partial side elevational view of the instrument of FIG. 34 incorporating the rigidizing member and drive member of FIG. 44, with the drive member in an intermediate position.
Figure 50:
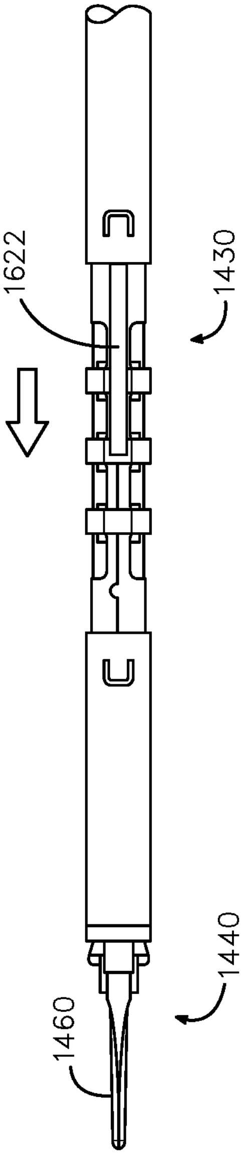
FIG. 50 depicts another detailed top plan view of the shaft assembly and the end effector of the instrument of FIG. 34, with the rigidizing member in an intermediate position.
Figure 51:
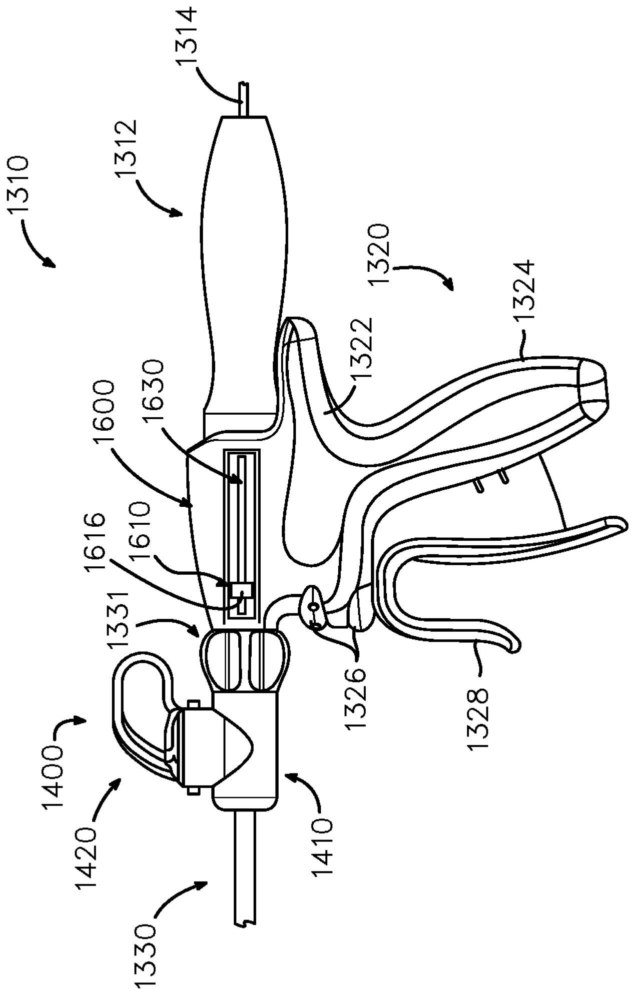
FIG. 51 depicts still another partial side elevational view of the instrument of FIG. 34 incorporating the rigidizing member and drive member of FIG. 44, with the drive member in a distal position.
Figure 52:
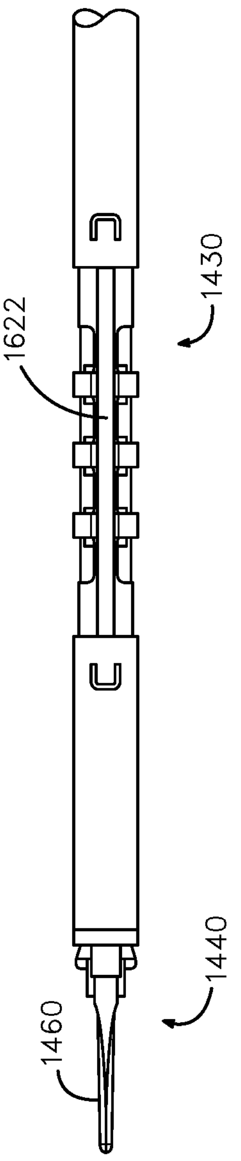
FIG. 52 depicts still another detailed top plan view of the shaft assembly and the end effector of the instrument of FIG. 34, with the rigidizing member in a distal position.

If an operator desires to rigidize articulation section (1430), the operator may do so by advancing drive assembly (1600) to a second longitudinal position (as shown in FIGS. 51 and 52). To advance drive assembly (1600) to the second position, the operator will advance tabs (1616) of drive member (1610) distally as shown in FIG. 49. Distal advancement of drive member (1610) will cause corresponding advancement of post (1622) of rigidizing member (1620) within shaft assembly (1330) as shown in FIG. 50. As post (1622) is advanced distally, post (1622) begins to engage articulation section (1430).

FIGS. 51 and 52 show drive assembly (1600) fully advanced to the second position. As can be seen, in the second position, tabs (1616) of drive member (1610) are advanced to a fully distal position relative to handle assembly (1320). Correspondingly, post (1622) of rigidizing member (1520) is advanced to a fully distal position. When post (1622) is in the fully distal position, post (1622) fully engages articulation section (1430) to rigidize articulation section (1430). In this state, the distal ends of post (1622) is positioned distal to articulation section (1430), such that post (1622) spans along the full length of articulation section (1430) and is grounded relative to the distal portion of shaft assembly (1330). In the present example, post (1622) extends along a path that is offset from the articulation plane of articulation section (1430). In particular, post (1622) is located above the articulation plane of articulation section (1430). This positioning of post (1622) may enhance the rigidization effect provided by post (1622) when post (1622) is in the distal position shown in FIG. 52. In some other versions, post (1622) is located in the articulation plane of articulation section (1430) (e.g., similar to the positioning of one of posts (1522)), on one side of articulation section (1430).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus for operating on tissue, the apparatus comprising: (a) a body assembly; (b) a shaft extending distally from the body assembly, wherein the shaft defines a longitudinal axis; (c) an acoustic waveguide, wherein the waveguide comprises a flexible portion; (d) an articulation section coupled with the shaft, wherein a portion of the articulation section encompasses the flexible portion of the waveguide, wherein the articulation section further comprises: (i) a first member, and (ii) a second member, wherein the second member is longitudinally translatable relative to the first member; (e) an end effector comprising an ultrasonic blade in acoustic communication with the waveguide; and (f) a rigidizing member, wherein the rigidizing member is configured to selectively engage at least a portion of the articulation section to thereby selectively provide rigidity to the articulation section.

Example 2

The apparatus of Example 1 or any of the following examples, wherein the rigidizing member is movable relative to the shaft to selectively engage at least a portion of the articulation section.

Example 3

The apparatus of Example 2, wherein the rigidizing member is disposed about at least a portion of the shaft.

Example 4

The apparatus of Example 3, wherein the rigidizing member comprises an elongate tubular member, wherein the elongate tubular member is translatable relative to the shaft to cover at least a portion of the articulation section thereby provide rigidity to the articulation section.

Example 5

The apparatus of Example 4, wherein the shaft includes a distal stop member and a proximal stop member, wherein the distal stop member is configured to secure the elongate tubular member in a first longitudinal position, wherein the proximal stop member is configured to secure the elongate tubular member in a second longitudinal position, wherein the first longitudinal position of the elongate tubular member corresponds to the elongate tubular member covering at least a portion of the articulation section.

Example 6

The apparatus of Example 4, wherein at least a portion of the elongate tubular member extends into the body assembly, wherein the body assembly includes an rigidizing member actuation assembly, wherein the rigidizing member actuation assembly is configured to transition the elongate tubular member between a first longitudinal position and a second longitudinal position.

Example 7

The apparatus of Example 6, wherein the elongate tubular member is configured to provide rigidity to the articulation section when the elongate tubular member is in the second longitudinal position.

Example 8

The apparatus of Example 3, wherein the rigidizing member is roatatable about the shaft between a first angular position and a second angular position, wherein the rigidizing member is configured to provide rigidity to the articulation section when the rigidizing member is in the second angular position, wherein the rigidizing member is configured to permit the articulation section to flex when the rigidizing member is in the first angular position.

Example 9

The apparatus of Example 8, wherein the rigidizing member comprises a plurality of links, wherein each link includes at least one bending feature and at least one rigidizing feature.

Example 10

The apparatus of Example 9, wherein each link of the plurality of links is coupled to another link of the plurality of links, wherein each bending feature of each link is aligned along a first plane, wherein each rigidizing feature is aligned along a second plane, wherein the rigidizing member is configured to bend about the first plane, wherein the rigidizing member is configured to be rigid about the second plane.

Example 11

The apparatus of Example 10, wherein the first plane of the rigidizing member is aligned with an articulation plane of the articulation section when the rigidizing member is in the first position, wherein the second plane of the rigidizing member is aligned with the articulation plane of the articulation section when the rigidizing member is in the second position.

Example 12

The apparatus of Example 8, wherein the rigidizing member includes at least one integral tab, wherein the integral tab is configured to engage with the articulation section to prevent movement of the articulation section with the rigidizing member is in the second position.

Example 13

The apparatus of any of the preceding or following Examples, wherein the rigidizing member includes a first interlocking coil and a second interlocking coil, wherein the second interlocking coil is configured to transition between a first position and a second position, wherein the second interlocking coil is at least partially separated from the first interlocking coil when the second interlocking coil is in the first position, wherein the first interlocking coil is fully interlocked with the first interlocking coil when the second interlocking coil is in the second position, wherein the rigidizing member is configured to prevent movement of the articulation section when the second interlocking coil is in the second position, wherein the rigidizing member is configured to permit the articulation section to flex when the second interlocking coil is in the first position.

Example 14

The apparatus of any of the preceding or following Examples, wherein at least a portion of the rigidizing member is disposed within at least a portion of the shaft.

Example 15

The apparatus of Example 14, wherein the rigidizing member is translatable within the shaft between a first longitudinal position and a second longitudinal position, wherein the rigidizing member is configured to engage with the articulation section when the rigidizing member is in the second longitudinal position, wherein the rigidizing member is configured to prevent movement of the articulation section when the rigidizing member is in the second longitudinal position.

Example 16

The apparatus of Example 15, wherein the body assembly includes a rigidizing member actuation assembly, wherein the rigidizing member actuation assembly is configured to transition the rigidizing member between the first longitudinal position and the second longitudinal position.

Example 17

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section, wherein the end effector comprises a working element configured to engage tissue; (e) an articulation drive assembly operable to drive articulation of the articulation section to thereby deflect the end effector from the longitudinal axis; and (f) an rigidizing assembly, wherein the rigidizing assembly comprises at least one stiffener, wherein the stiffener is movable between a first position and a second position, wherein the stiffener is operable to rigidize the articulation section when the stiffener is in the second position, wherein the stiffener is operable to permit flexing of the articulation section when the stiffener is in the first position.

Example 18

The apparatus Example 17, wherein the stiffener is disposed on an exterior of the shaft, wherein the stiffener is configured to translate along at least a portion of the shaft to transition the stiffener between the first position and the second position.

Example 19

The apparatus of Example 17, wherein the stiffener is disposed within at least a portion of the shaft, wherein the stiffener is configured to translate within at least a portion of the shaft to transition between the first position and the second position, wherein the stiffener is configured to engage at least a portion of the articulation section when the stiffener is in the second position.

Example 20

An apparatus for operating on tissue, the apparatus comprising: (a) a body assembly; (b) a shaft extending distally from the body assembly, wherein the shaft defines a longitudinal axis; (c) an articulation section coupled with the shaft; (d) an end effector coupled with the articulation section; (e) a first pair of translating members, wherein the first pair of translating members is operable to actuate the articulation section to thereby deflect the end effector from the longitudinal axis; (f) a drive assembly in communication with the first pair of translating members, wherein the drive assembly is configured to translate the first pair of translating members to actuate the articulation section; and (g) a rigidizing member, wherein the rigidizing member is associated with the shaft, wherein the rigidizing member is movable relative to the shaft to engage the articulation section, wherein the rigidizing member is configured to ridigize the articulation section when the rigidizing member is engaged with the articulation section.

IV. Miscellaneous

It should be understood that any of the versions of instruments described herein may include various other features in addition to or in lieu of those described above. By way of example only, any of the instruments described herein may also include one or more of the various features disclosed in any of the various references that are incorporated by reference herein. It should also be understood that the teachings herein may be readily applied to any of the instruments described in any of the other references cited herein, such that the teachings herein may be readily combined with the teachings of any of the references cited herein in numerous ways. Moreover, those of ordinary skill in the art will recognize that various teachings herein may be readily applied to electrosurgical instruments, stapling instruments, and other kinds of surgical instruments. Other types of instruments into which the teachings herein may be incorporated will be apparent to those of ordinary skill in the art.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of U.S. Pat. No. 6,783,524, entitled "Robotic Surgical Tool with Ultrasound Cauterizing and Cutting Instrument," published Aug. 31, 2004, the disclosure of which is incorporated by reference herein.

Versions described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. An ultrasonic surgical instrument, comprising:

(a) an end effector including an ultrasonic blade;

(b) a shaft proximally extending from the end effector and having a distal shaft portion and a proximal shaft portion, wherein the proximal shaft portion defines a longitudinal axis;

(c) an acoustic waveguide having a flexible portion;

(d) an articulation section coupled with the shaft between the distal and proximal shaft portions, wherein at least a portion of the articulation section encompasses the flexible portion of the acoustic waveguide; and (e) a rigidizing member configured to selectively move from a first position toward a second position, wherein the rigidizing member in the first position extends from the proximal shaft portion to the distal shaft portion in a rigid state to selectively lock rigidity to the articulation section, wherein the rigidizing member in the second position extends from the proximal shaft portion to the distal shaft portion in an articulatable state to selectively unlock rigidity of the articulation section such that the end effector is configured to deflect relative to the longitudinal axis, wherein the rigidizing member includes a plurality of bars wherein the plurality of bars are pivotally connected.

2. The ultrasonic surgical instrument of claim 1, further comprising a first fixed portion fixed to the articulation section, wherein the rigidizing member in the first position is selectively engaged with the first fixed portion to thereby selectively lock rigidity of the articulation section.

3. The ultrasonic surgical instrument of claim 2, wherein the rigidizing member in the second position is selectively disengaged with the first fixed portion to thereby selectively unlock rigidity of the articulation section.

4. The ultrasonic surgical instrument of claim 3, wherein the first fixed portion includes a first ridge extending from the articulation section.

5. The ultrasonic surgical instrument of claim 3, further comprising a second fixed portion fixed to the proximal shaft portion, wherein the rigidizing member in the first position is selectively engaged with the second fixed portion to thereby further selectively lock rigidity of the articulation section.

6. The ultrasonic surgical instrument of claim 3, wherein the rigidizing member is configured to proximally translate to thereby deflect the rigidizing member toward the second position for selective disengagement from the first fixed portion.

7. The ultrasonic surgical instrument of claim 6, wherein the rigidizing member is configured to proximally translate to thereby transversely deflect the rigidizing member toward the second position for selective disengagement from the first fixed portion.

8. The ultrasonic surgical instrument of claim 1, wherein the plurality of bars includes a first bar and a second bar, wherein the first and second bars are pivotally connected at a connector.

9. The ultrasonic surgical instrument of claim 8, wherein the first bar is pivotally connected to the distal shaft portion, and wherein the first bar is translatably connected to the distal shaft portion.

10. The ultrasonic surgical instrument of claim 8, further comprising a first fixed portion fixed to the articulation section, wherein the connector in the first position is selectively engaged with the first fixed portion to thereby selectively lock rigidity of the articulation section.

11. The ultrasonic surgical instrument of claim 10, wherein the first fixed portion includes a first ridge extending from the articulation section.

12. The ultrasonic surgical instrument of claim 11, wherein the first fixed portion includes a second ridge extending from the articulation section, wherein the first and second ridges define a gap therebetween, and wherein the connector is received within the gap in the first position.

13. The ultrasonic surgical instrument of claim 8, wherein the plurality of bars includes a third bar, wherein the third bar is pivotally connected to the second bar.

14. An ultrasonic surgical instrument, comprising:
(a) an end effector including an ultrasonic blade;
(b) a shaft proximally extending from the end effector and having a distal shaft portion and a proximal shaft portion, wherein the proximal shaft portion defines a longitudinal axis;
(c) an acoustic waveguide having a flexible portion;
(d) an articulation section coupled with the shaft between the distal and proximal shaft portions and configured to articulate from a straight configuration to an articulated configuration, wherein at least a portion of the articulation section encompasses the flexible portion of the acoustic waveguide; and
(e) a plurality of bars configured to selectively move from a first position toward a second position, wherein the plurality of bars in the first position extends from the proximal shaft portion to the distal shaft portion in a rigid state to selectively lock rigidity to the articulation section, wherein the plurality of bars in the second position extends from the proximal shaft portion to the distal shaft portion in an articulatable state to selectively unlock rigidity of the articulation section such that the end effector is configured to deflect relative to the longitudinal axis along an articulation plane,
wherein the plurality of bars in the rigid state extends in a rigid plane, wherein the rigid plane is perpendicular to the articulation plane, and
wherein at least one of the plurality of bars is configured to move perpendicular to the rigid plane upon articulation of the articulation section from the straight configuration toward the articulated configuration.

15. The ultrasonic surgical instrument of claim 14, further comprising a first fixed portion fixed to the articulation section, wherein the plurality of bars includes a first bar and a second bar, wherein the first and second bars are pivotally connected, and wherein at least a portion of the first bar is selectively engaged with the first fixed portion to thereby selectively lock rigidity of the articulation section.

16. An ultrasonic surgical instrument, comprising:
(a) an end effector including an ultrasonic blade;
(b) a shaft proximally extending from the end effector and having a distal shaft portion and a proximal shaft portion, wherein the proximal shaft portion defines a longitudinal axis;
(c) an acoustic waveguide having a flexible portion;
(d) an articulation section coupled with the shaft between the distal and proximal shaft portions, wherein at least a portion of the articulation section encompasses the flexible portion of the acoustic waveguide;
(e) a first fixed portion operatively connected to the articulation section; and
(f) a rigidizing member configured to selectively move from a first position toward a second position, wherein the rigidizing member in the first position extends from the proximal shaft portion to the distal shaft portion in a rigid state to selectively lock rigidity to the articulation section, wherein the rigidizing member in the second position extends from the proximal shaft portion to the distal shaft portion in an articulatable state to selectively unlock rigidity of the articulation section such that the end effector is configured to deflect relative to the longitudinal axis, wherein the rigidizing member is configured to proximally translate to thereby deflect the rigidizing member toward the second position for selective disengagement from the first fixed portion.

17. The ultrasonic surgical instrument of claim 16, wherein the first fixed portion is fixed to the articulation section.

18. The ultrasonic surgical instrument of claim 17, wherein the rigidizing member in the first position is selectively engaged with the first fixed portion to thereby selectively lock rigidity of the articulation section.

19. The ultrasonic surgical instrument of claim 18, wherein the rigidizing member in the second position is selectively disengaged with the first fixed portion to thereby selectively unlock rigidity of the articulation section.

* * * * *